United States Patent
Ansell et al.

(10) Patent No.: US 9,463,247 B2
(45) Date of Patent: Oct. 11, 2016

(54) BRANCHED ALKYL AND CYCLOALKYL TERMINATED BIODEGRADABLE LIPIDS FOR THE DELIVERY OF ACTIVE AGENTS

(71) Applicant: ALNYLAM PHARMACEUTICALS, INC., Cambridge, MA (US)

(72) Inventors: Steven M. Ansell, Vancouver (CA); Xinyao Du, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/362,864

(22) PCT Filed: Dec. 7, 2012

(86) PCT No.: PCT/US2012/068450
§ 371 (c)(1),
(2) Date: Jun. 4, 2014

(87) PCT Pub. No.: WO2013/086322
PCT Pub. Date: Jun. 13, 2013

(65) Prior Publication Data
US 2015/0005363 A1    Jan. 1, 2015

Related U.S. Application Data

(60) Provisional application No. 61/568,121, filed on Dec. 7, 2011.

(51) Int. Cl.
| | | |
|---|---|---|
| A61K 47/14 | (2006.01) | |
| C12N 15/113 | (2010.01) | |
| C07C 229/12 | (2006.01) | |
| C07C 217/08 | (2006.01) | |

(52) U.S. Cl.
CPC .............. *A61K 47/14* (2013.01); *C07C 217/08* (2013.01); *C07C 229/12* (2013.01); *C12N 15/113* (2013.01); *C07C 2101/08* (2013.01); *C07C 2101/14* (2013.01); *C07C 2102/28* (2013.01); *C12N 2320/32* (2013.01)

(58) Field of Classification Search
None
See application file for complete search history.

(56) References Cited

U.S. PATENT DOCUMENTS

2010/0324120 A1* 12/2010 Chen .................... A61K 9/1272
514/44 A

FOREIGN PATENT DOCUMENTS

| JP | 9278726 | 10/1997 |
|---|---|---|
| WO | WO-2010054401 A1 | 5/2010 |
| WO | WO-2011153493 A2 | 12/2011 |

OTHER PUBLICATIONS

LV, et al., Toxicity of Cationic Lipids and Cationic Polymers in Gene Delivery, Journal of Controlled Release, 2006, 114:1:100-109.
International Search Report issued in PCT/US2012/068450 on Apr. 4, 2013.

* cited by examiner

*Primary Examiner* — Brian J Davis
(74) *Attorney, Agent, or Firm* — Blank Rome LLP

(57) ABSTRACT

The present invention relates to a cationic lipid of formula (I) having one or more biodegradable groups located in a lipidic moiety (e.g., a hydrophobic chain) of the cationic lipid. These cationic lipids may be incorporated into a lipid particle for delivering an active agent, such as a nucleic acid. The invention also relates to lipid particles comprising a neutral lipid, a lipid capable of reducing aggregation, a cationic lipid of the present invention, and optionally, a sterol. The lipid particle may further include a therapeutic agent such as a nucleic acid.

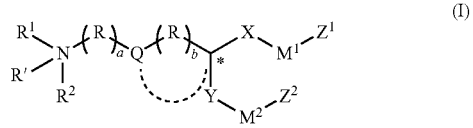

29 Claims, No Drawings

```
                          SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (3)..(4)
<223> OTHER INFORMATION: 2'F modified nucleobase
<220> FEATURE:
<221> NAME/KEY: modified_base
<222> LOCATION: (6)..(9)
<223> OTHER INFORMATION: 2'F modified nucleobase
<220> FEATURE:
<221> NAME/KEY: modified_base
<222> LOCATION: (13)..(16)
<223> OTHER INFORMATION: 2'F modified nucleobase
<220> FEATURE:
<221> NAME/KEY: modified_base
<222> LOCATION: (18)..(18)
<223> OTHER INFORMATION: 2'F modified nucleobase
<220> FEATURE:
<221> NAME/KEY: misc_feature
<222> LOCATION: (20)..(21)
<223> OTHER INFORMATION: Phosphothioate linkage

<400> SEQUENCE: 1
ggaucaucuc aagucuuact t                                             21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(1)
<223> OTHER INFORMATION: 2'F modified nucleobase
<220> FEATURE:
<221> NAME/KEY: modified_base
<222> LOCATION: (6)..(8)
<223> OTHER INFORMATION: 2'F modified nucleobase
<220> FEATURE:
<221> NAME/KEY: modified_base
<222> LOCATION: (13)..(13)
<223> OTHER INFORMATION: 2'F modified nucleobase
<220> FEATURE:
<221> NAME/KEY: modified_base
<222> LOCATION: (16)..(18)
<223> OTHER INFORMATION: 2'F modified nucleobase
<220> FEATURE:
<221> NAME/KEY: misc_feature
<222> LOCATION: (20)..(21)
<223> OTHER INFORMATION: Phosphothioate linkage
```

```
<400> SEQUENCE: 2
guaagacuug agaugaucct t                                    21
```

BRANCHED ALKYL AND CYCLOALKYL TERMINATED BIODEGRADABLE LIPIDS FOR THE DELIVERY OF ACTIVE AGENTS

This application is the U.S. national phase of International Patent Application No. PCT/US12/68450, filed Dec. 7, 2012, which claims the benefit of U.S. Provisional Application No. 61/568,121, filed Dec. 7, 2011, which is hereby incorporated by reference.

TECHNICAL FIELD

The present invention relates to biodegradable lipids and to their use for the delivery of active agents such as nucleic acids.

BACKGROUND

Therapeutic nucleic acids include, e.g., small interfering RNA (siRNA), micro RNA (miRNA), antisense oligonucleotides, ribozymes, plasmids, immune stimulating nucleic acids, antisense, antagomir, antimir, microRNA mimic, supermir, U1 adaptor, and aptamer. In the case of siRNA or miRNA, these nucleic acids can down-regulate intracellular levels of specific proteins through a process termed RNA interference (RNAi). The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind the protein RISC when administered systemically as the free siRNA or miRNA. Lipid nanoparticles formed from cationic lipids with other lipid components, such as cholesterol and PEG lipids, and oligonucleotides (such as siRNA and miRNA) have been used to facilitate the cellular uptake of the oligonucleotides.

There remains a need for improved cationic lipids and lipid nanoparticles for the delivery of oligonucleotides. Preferably, these lipid nanoparticles would provide high drug:lipid ratios, protect the nucleic acid from degradation and clearance in serum, be suitable for systemic delivery, and provide intracellular delivery of the nucleic acid. In addition, these lipid-nucleic acid particles should be well-tolerated and provide an adequate therapeutic index, such that patient treatment at an effective dose of the nucleic acid is not associated with significant toxicity and/or risk to the patient.

SUMMARY

The present invention relates to a cationic lipid suitable for forming nucleic acid-lipid particles. Each of the cationic lipids of the present invention includes one or more biodegradable groups. The biodegradable groups are located in a lipidic moiety (e.g., a hydrophobic chain) of the cationic lipid. These cationic lipids may be incorporated into a lipid particle for delivering an active agent, such as a nucleic acid (e.g., an siRNA). The incorporation of the biodegradable group(s) into the cationic lipid results in faster metabolism and removal of the cationic lipid from the body following delivery of the active agent to a target area. As a result, these cationic lipids have lower toxicity than similar cationic lipids without the biodegradable groups.

In one embodiment, the cationic lipid is a compound of the formula:

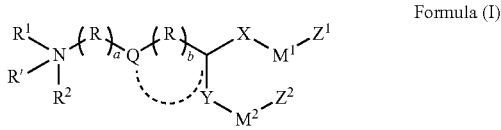

Formula (I)

or a salt thereof (e.g., a pharmaceutically acceptable salt thereof), wherein
R' is absent, hydrogen, or alkyl (e.g., $C_1$-$C_4$ alkyl);
with respect to $R^1$ and $R^2$,
(i) $R^1$ and $R^2$ are each, independently, optionally substituted alkyl, alkenyl, alkynyl, cycloalkyl, cycloalkylalkyl, heterocycle, or $R^{10}$;
(ii) $R^1$ and $R^2$, together with the nitrogen atom to which they are attached, form an optionally substituted heterocylic ring; or
(iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the (R)$_a$ group adjacent to the nitrogen atom;
each occurrence of R is, independently, —(CR³R⁴)—;
each occurrence of $R^3$ and $R^4$ are, independently hydrogen, OH, alkyl, alkoxy, —NH₂, $R^{10}$, alkylamino, or dialkylamino (in one preferred embodiment, each occurrence of $R^3$ and $R^4$ are, independently hydrogen or $C_1$-$C_4$ alkyl);
each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups (preferably at most one $R^{10}$ group);
the dashed line to Q is absent or a bond;
when the dashed line to Q is absent then Q is absent or is —O—, —NH—, —S—, —C(O)—, —C(O)O—, —OC(O)—, —C(O)N(R⁴)—, —N(R⁵)C(O)—, —S—S—, —OC(O)O—, —O—N═C(R⁵)—, —C(R⁵)═N—O—, —OC(O)N(R⁵)—, —N(R⁵)C(O)N(R⁵)—, —N(R⁵)C(O)O—, —C(O)S—, —C(S)O— or —C(R⁵)═N—O—C(O)—; or
when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);
each occurrence of $R^5$ is, independently, hydrogen or alkyl;
X and Y are each, independently, —(CR⁶R⁷)$_c$—;
each occurrence of $R^6$ and $R^7$ are, independently hydrogen, OH, alkyl, alkoxy, —NH₂, alkylamino, or dialkylamino (in one preferred embodiment, each occurrence of $R^6$ and $R^7$ are, independently H or $C_1$-$C_4$ alkyl);
$M^1$ and $M^2$ are each, independently, a biodegradable group (e.g., —OC(O)—, —C(O)O—, —SC(O)—, —C(O)S—, —OC(S)—, —C(S)O—, —S—S—, —C(R⁵)═N—, —N═C(R⁵)—, —C(R⁵)═N—O—, —O—N═C(R⁵)—, —C(O)(NR⁵)—, —N(R⁵)C(O)—, —C(S)(NR⁵)—, —N(R⁵)C(O)—, —N(R⁵)C(O)N(R⁵)—, —OC(O)O—, —OSi(R⁵)₂O—, —C(O)(CR³R⁴)C(O)O—, or —OC(O)(CR³R⁴)C(O)—);
a is 1, 2, 3, 4, 5 or 6;
b is 0, 1, 2, or 3;

each occurrence of c is, independently, 2-10 (i.e., 2, 3, 4, 5, 6, 7, 8, 9, or 10); and $Z^1$ and $Z^2$ are each, independently (i) $C_3$-$C_{10}$ cycloalkyl, (ii) $C_3$-$C_{10}$ cycloalkyl($C_1$-$C_6$ alkyl), or (iii)

where each of $R^8$ and $R^9$ is, independently, a $C_2$-$C_8$ alkyl (e.g., $C_2$-alkyl, —$CH_2CH(CH_3)_2$, n-$C_4$ alkyl).

In one embodiment, (i) $R^1$ and $R^2$ are each, independently, optionally substituted alkyl, alkenyl, alkynyl, cycloalkyl, cycloalkylalkyl, or heterocycle; or (ii) $R^1$ and $R^2$, together with the nitrogen atom to which they are attached, form an optionally substituted heterocylic ring.

In one embodiment, $R^1$ and $R^2$ are both alkyl (e.g., methyl).

In a further embodiment, a is 3. In another embodiment, b is 0.

In a further embodiment, a is 3, b is 0 and R is —$CH_2$—. In yet a further embodiment, a is 3, b is 0, R is —$CH_2$— and Q is —C(O)O—. In another embodiment, $R^1$ and $R^2$ are methyl, a is 3, b is 0, R is —$CH_2$— and Q is —C(O)O—.

In another embodiment, X and Y are each, independently —$(CH_2)_c$—. The variable c can be, for example, 4 to 10 or 6 to 10. For example, X and Y are independently, —$(CH_2)_8$— or —$(CH_2)_9$—. In one embodiment, X and Y are —$(CH_2)_8$—. In another embodiment, X and Y are —$(CH_2)_9$—.

In further embodiments, $M^1$ and $M^2$ are each, independently, —OC(O)— or —C(O)O—. For example, in one embodiment, $M^1$ and $M^2$ are each —C(O)O—.

In yet additional embodiments, $Z^1$ and $Z^2$ are each, independently, $C_3$-$C_{10}$ cycloalkyl. For example, in one embodiment, $Z^1$ and $Z^2$ are each cyclohexyl. In another embodiment, $Z^1$ and $Z^2$ are each decahydronaphthalenyl (e.g., 2-decahydronaphthalenyl).

In further embodiments, $Z^1$ and $Z^2$ are each, independently, branched alkyl, wherein each branch of the branched alkyl contains 2 or more carbon atoms (e.g., 4 or more carbon atoms) and the alkyl group is branched at the carbon atom alpha to the biodegradable group.

For example, in certain embodiments, $Z^1$ and $Z^2$ are each, independently, represented by Formula (II):

Formula (II)

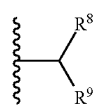

wherein $R^8$ and $R^9$ are each, independently $C_3$-$C_8$ alkyl (e.g., $C_4$ alkyl, such as n-butyl).

In one embodiment, the compound of Formula I is of subformula (III):

Formula (III)

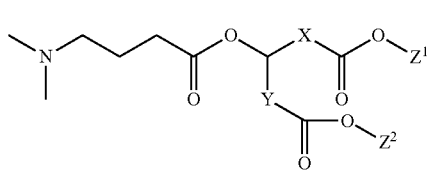

wherein X, Y, $Z^1$ and $Z^2$ are as defined above with respect to Formula I.

In another embodiment, a carbon atom in group X or Y that is alpha or beta to a biodegradable group (e.g., —C(O)O—) in formula (I) may be substituted with one or two alkyl groups (e.g., one $C_1$-$C_4$ alkyl group, such as a —$CH_3$ substituent, or two $C_1$-$C_4$ alkyl groups, such as two —$CH_3$ substituents) or have a spirocyclic group (e.g., a $C_3$-$C_5$ cycloalkyl such as a $C_3$ cycloalkyl). For example, a carbon atom in group X or Y alpha or beta to a biodegradable group can be independently selected from

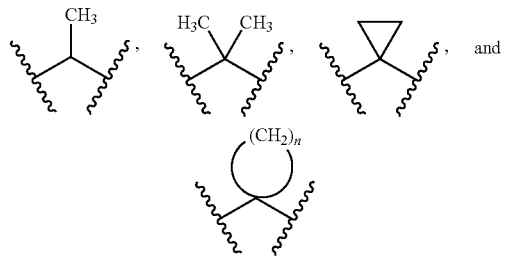

(where n is 4-6).

In one embodiment, the $M^1$ or $M^2$ group and neighboring variable(s) from group X or Y form the group:

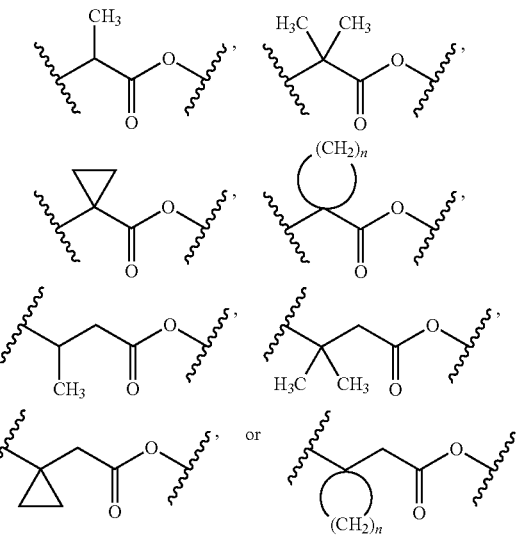

(where n is 4-6).

Yet another embodiment is a lipid particle that includes a cationic lipid of the present invention. In one embodiment, the lipid particle includes a c compound of formula I as described herein. In another embodiment, the lipid particle includes a compound of formula III as described herein.

In a preferred embodiment, the lipid particle includes a neutral lipid, a lipid capable of reducing aggregation, a cationic lipid, and optionally, a sterol (e.g., cholesterol). Suitable neutral lipids include, but are not limited to, distearoylphosphatidylcholine (DSPC), dipalmitoylphosphatidylcholine (DPPC), POPC, DOPE, and SM. Suitable lipids capable of reducing aggregation include, but are not limited to, a PEG lipid, such as PEG-DMA, PEG-DMG, or a combination thereof.

The lipid particle may further include an active agent (e.g., a therapeutic agent). The active agent can be a nucleic acid such as a plasmid, an immunostimulatory oligonucleotide, an siRNA, an antisense oligonucleotide, a microRNA, an antagomir, an aptamer, or a ribozyme. In a preferred embodiment, the nucleic acid is a siRNA. In another preferred embodiment, the nucleic acid is a miRNA.

In another embodiment, the lipid particle includes a cationic lipid of the present invention, a neutral lipid and a sterol. The lipid particle may further include an active agent, such as a nucleic acid (e.g., an siRNA or miRNA).

The lipid particles described herein may be lipid nanoparticles.

Yet another embodiment of the invention is a pharmaceutical composition which includes a lipid particle of the present invention and a pharmaceutically acceptable carrier.

In one embodiment, the cationic lipid remains intact until delivery of the nucleic acid molecule after which cleavage of the hydrophobic tail occurs in vivo.

In another embodiment, the present invention relates to a method of delivering a nucleic acid molecule comprising administering a nucleic lipid particle comprising the nucleic acid molecule and a cationic lipid of the present invention. In one embodiment, the cationic lipid remains intact until delivery of the nucleic acid molecule after which cleavage of the hydrophobic tail occurs in vivo.

Yet another aspect is a method of modulating the expression of a target gene in a cell by providing to the cell a lipid particle of the present invention. The active agent can be a nucleic acid selected from a plasmid, an immunostimulatory oligonucleotide, an siRNA, an antisense oligonucleotide, a microRNA, an antagomir, an aptamer, and a ribozyme. In a preferred embodiment, the nucleic acid is a siRNA or miRNA.

Yet another aspect is a method of treating a disease or disorder characterized by the overexpression of a polypeptide in a subject by providing to the subject a pharmaceutical composition of the present invention, wherein the active agent is a nucleic acid selected from an siRNA, a microRNA, and an antisense oligonucleotide, and wherein the siRNA, microRNA, or antisense oligonucleotide includes a polynucleotide that specifically binds to a polynucleotide that encodes the polypeptide, or a complement thereof. In a preferred embodiment, the nucleic acid is a siRNA or miRNA.

Yet another aspect is a method of treating a disease or disorder characterized by underexpression of a polypeptide in a subject by providing to the subject a pharmaceutical composition of the present invention, wherein the active agent is a plasmid that encodes the polypeptide or a functional variant or fragment thereof.

Yet another aspect is a method of inducing an immune response in a subject by providing to the subject a pharmaceutical composition wherein the active agent is an immunostimulatory oligonucleotide.

Yet another aspect is a transfection agent that includes the composition or lipid particles described above, where the composition or lipid particles include a nucleic acid. The agent, when contacted with cells, can efficiently deliver nucleic acids to the cells. Yet another aspect is a method of delivering a nucleic acid to the interior of a cell, by obtaining or forming a composition or lipid particles described above, and contacting the composition or lipid particles with a cell.

DETAILED DESCRIPTION

In one aspect, the present invention relates to a lipid particle that includes a neutral lipid, a lipid capable of reducing aggregation, a cationic lipid, and optionally a sterol. In certain embodiments, the lipid particle further includes an active agent (e.g., a therapeutic agent). Various exemplary embodiments of these lipids, lipid particles and compositions comprising the same, and their use to deliver therapeutic agents and modulate gene and protein expression are described in further detail below.

The Cationic Lipid

In one embodiment, the cationic lipid is a compound of Formula I. In another embodiment, the cationic lipid is a compound of Formula III. The following disclosure represents various embodiments of compounds of Formula I.

In one embodiment, $M^1$ and $M^2$ are each, independently:
—OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, or —OC(O)(C$R^3R^4$)C(O)—.

In another embodiment, $M^1$ and $M^2$ are each, independently:
—OC(O)—, —C(O)—O—, —C($R^5$)=N—, —N=C($R^5$)—, —C($R^5$)=N—O—, —O—N=C($R^5$)—, —O—C(O)O—, —C(O)N($R^5$)—, —N($R^5$)C(O)—, —C(O)S—, —SC(O)—, —C(S)O—, —OC(S)—, —OSi($R^5$)$_2$O—, —C(O)(C$R^3R^4$)C(O)O—, or —OC(O)(C$R^3R^4$)C(O)—.

In yet another embodiment, $M^1$ and $M^2$ are each, independently:
—C(O)—O—, —OC(O)—, —C($R^5$)=N—, —C($R^5$)=N—O—, —O—C(O)O—, —C(O)N($R^5$)—, —C(O)S—, —C(S)O—, —OSi($R^5$)$_2$O—, —C(O)(C$R^3R^4$)C(O)O—, or —OC(O)(C$R^3R^4$)C(O)—.

In another embodiment, $M^1$ and $M^2$ are each —C(O)O—.

In one embodiment, $R^1$ and $R^2$ are each, individually, optionally substituted alkyl, cycloalkyl, cycloalkylalkyl, or heterocycle. In one embodiment, $R^1$ is alkyl and $R^2$ is alkyl, cycloalkyl or cycloalkylalkyl. In one embodiment, $R^1$ and $R^2$ are each, individually, alkyl (e.g., $C_1$-$C_4$ alkyl, such as methyl, ethyl, or isopropyl). In one embodiment, $R^1$ and $R^2$ are both methyl. In another embodiment, $R^1$ and $R^2$, together with the nitrogen atom to which they are attached, form an optionally substituted heterocyclic ring (e.g., N-methylpiperazinyl). In another embodiment, one of $R^1$ and $R^2$ is

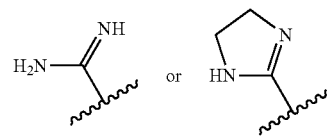

(e.g., $R^1$ is one of the two aforementioned groups and $R^2$ is hydrogen).

In one embodiment, R' is hydrogen or alkyl. In another embodiment, R' is hydrogen or methyl. In one embodiment, R' is absent. In one embodiment, R' is absent or methyl.

For cationic lipid compounds which contain an atom (e.g., a nitrogen atom) that carries a positive charge, the compound also contains a negatively charged counter ion. The counterion can be any anion, such as an organic or inorganic anion. Suitable examples of anions include, but are not limited to, tosylate, methanesulfonate, acetate, citrate, malonate, tartarate, succinate, benzoate, ascorbate, α-ketoglutarate, α-glycerophosphate, halide (e.g., chloride), sulfate, nitrate, bicarbonate, and carbonate. In one embodiment, the counterion is a halide (e.g., Cl).

In one embodiment each R is, independently, —(C$R^3R^4$)—, wherein $R^3$ and $R^4$ are each, independently, H or alkyl (e.g., $C_1$-$C_4$ alkyl). For example, in one embodiment each R is, independently, —(CH$R^4$)—, wherein each $R^4$ is, independently H or alkyl (e.g., $C_1$-$C_4$ alkyl). In another embodiment, each R is, independently, —CH$_2$—, —C(CH$_3$)$_2$— or —CH(iPr)- (where iPr is isopropyl). In another embodiment, each R is —CH$_2$—.

In another embodiment R$^5$ is, in each case, hydrogen or methyl. For example, R$^5$ can be, in each case, hydrogen.

In one embodiment, Q is absent, —C(O)O—, —OC(O)—, —C(O)N(R$^5$)—, —N(R$^5$)C(O)—, —S—S—, —OC(O)O—, —C(R$^5$)=N—O—, —OC(O)N(R$^5$)—, —N(R$^5$)C(O)N(R$^5$)—, —N(R$^5$)C(O)O—, —C(O)S—, —C(S)O— or —C(R$^5$)=N—O—C(O)—. In one embodiment, Q is —C(O)O—.

In one embodiment, the dashed line to Q is absent, b is 0 and R'R$^1$R$^2$N—(R)$_a$-Q- and the tertiary carbon adjacent to it (C*) form the following group:

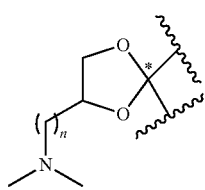

where n is 1 to 4 (e.g., n is 2).

In one embodiment, the dashed line to Q is absent, b is 0 and R'R$^1$R$^2$N—(R)$_a$-Q- and the tertiary carbon adjacent to it form the following group:

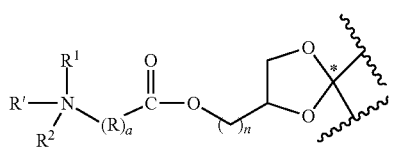

where n is 1 to 4 (e.g., n is 2), and R$^1$, R$^2$, R, a, and b are as defined with respect to formula (I). In one embodiment, a is 3.

In one embodiment, the dashed line to Q is absent, b is 0 and R'R$^1$R$^2$N—(R)$_a$-Q- and the tertiary carbon adjacent to it form the following group:

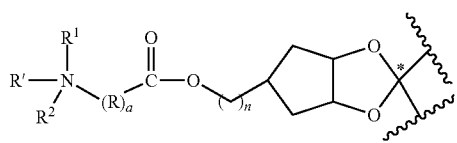

where n is 1 to 4 (e.g., n is 2), and R$^1$, R$^2$, R, a, and b are as defined with respect to formula (I). In one embodiment, a is 0. For example, the group can be:

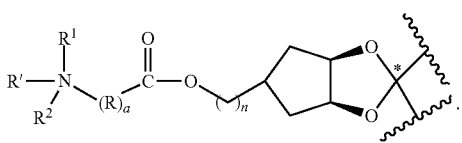

In one embodiment, b is 0. In another embodiment, a is 2, 3, or 4 and b is 0. For example, in one embodiment, a is 3 and b is 0. In another embodiment, a is 3, b is 0, and Q is —C(O)O—.

In certain embodiments, the biodegradable group present in the cationic lipid is selected from an ester (e.g., —C(O)O— or —OC(O)—), disulfide (—S—S—), oxime (e.g., —C(H)=N—O— or —O—N=C(H)—), —C(O)—O—, —OC(O)—, —C(R$^5$)=N—, —N=C(R$^5$)—, —C(R$^5$)=N—, —O—N=C(R$^5$)—, —O—C(O)O—, —C(O)N(R$^5$), —N(R$^5$)C(O)—, —C(S)(NR$^5$)—, (NR$^5$)C(S)—, —N(R$^5$)C(O)N(R$^5$)—, —C(O)S—, —SC(O)—, —C(S)O—, —OC(S)—, —OSi(R$^5$)$_2$O—, —C(O)(CR$^3$R$^4$)C(O)O—, or —OC(O)(CR$^3$R$^4$)C(O)—.

A suitable cholesterol moiety for the cationic lipids of the present invention (including compounds of formulas I and III) has the formula:

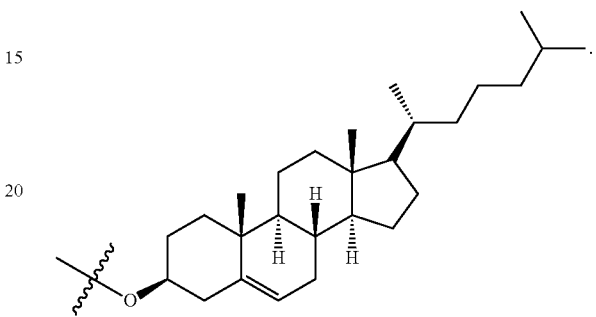

Additional embodiments include a cationic lipid having a head group, one or more hydrophobic tails, and a linker between the head group and the one or more tails. The head group can include an amine; for example an amine having a desired pK$_a$. The pK$_a$ can be influenced by the structure of the lipid, particularly the nature of head group; e.g., the presence, absence, and location of functional groups such as anionic functional groups, hydrogen bond donor functional groups, hydrogen bond acceptor groups, hydrophobic groups (e.g., aliphatic groups), hydrophilic groups (e.g., hydroxyl or methoxy), or aryl groups. The head group amine can be a cationic amine; a primary, secondary, or tertiary amine; the head group can include one amine group (monoamine), two amine groups (diamine), three amine groups (triamine), or a larger number of amine groups, as in an oligoamine or polyamine. The head group can include a functional group that is less strongly basic than an amine, such as, for example, an imidazole, a pyridine, or a guanidinium group. The head group can be zwitterionic. Other head groups are suitable as well.

The one or more hydrophobic tails can include two hydrophobic chains, which may be the same or different. The tails can be aliphatic, for example, they can be composed of carbon and hydrogen, either saturated or unsaturated but without aromatic rings. The tails can be fatty acid tails. Some such groups include octanyl, nonanyl, decyl, lauryl, myristyl, palmityl, stearyl, α-linoleyl, stearidonyl, linoleyl, γ-linolenyl, arachadonyl, and oleyl. Other hydrophobic tails are suitable as well.

The linker can include, for example, a glyceride linker, an acyclic glyceride analog linker, or a cyclic linker (including a spiro linker, a bicyclic linker, and a polycyclic linker). The linker can include functional groups such as an ether, an ester, a phosphate, a phosphonate, a phosphorothioate, a sulfonate, a disulfide, an acetal, a ketal, an imine, a hydrazone, or an oxime. Other linkers and functional groups are suitable as well.

In one embodiment, the cationic lipid is a racemic mixture. In another embodiment, the cationic lipid is enriched in one diastereomer, e.g. the cationic lipid has at least 95%, at least 90%, at least 80% or at least 70% diastereomeric excess. In yet another embodiment, the cationic lipid is enriched in one enantiomer, e.g. the lipid has at least 95%, at least 90%, at least 80% or at least 70% enantiomer excess. In yet another embodiment, the cationic lipid is chirally pure, e.g. is a single optical isomer. In yet another embodiment, the cationic lipid is enriched for one optical isomer.

The cationic lipid includes one or more biodegradable groups. The biodegradable group(s) include one or more bonds that may undergo bond breaking reactions in a biological environment, e.g., in an organism, organ, tissue, cell, or organelle. Functional groups that contain a biodegradable bond include, for example, esters, dithiols, and oximes. Biodegradation can be a factor that influences the clearance of the compound from the body when administered to a subject. Biodegredation can be measured in a cell based assay, where a formulation including a cationic lipid is exposed to cells, and samples are taken at various time points. The lipid fractions can be extracted from the cells and separated and analyzed by LC-MS. From the LC-MS data, rates of biodegradation (e.g., as $t_{1/2}$ values) can be measured.

For example, the compound structure of the compound, of course, influences the rate at which the compound undergoes biodegradation. Thus, a related compound such as

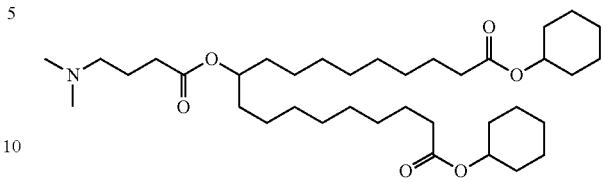

would be expected to exhibit a different rate of biodegradation. Greater effects on that rate would be expected from changes in the structure of the compound at the site of hydrolysis. One modification that can influence the rate of hydrolysis, and thereby influence the rate of biodegradation and clearance from a subject's body, is to make the leaving group of the hydrolysis reaction have a primary, rather than secondary, alcohol.

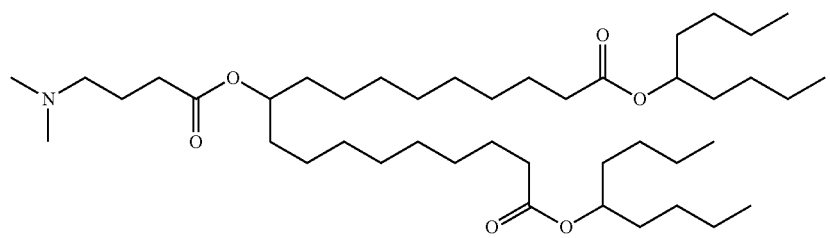 [SMILES: CCCCC(CCCC)OC(=O)CCCCCCCCC(CCCCCCCCC(=O)OC(CCCC)CCCC)OC(=O)CCCN(C)C]

includes an ester linkage in each aliphatic chain, which can undergo hydrolysis in a biological environment, for example, when exposed to, e.g., a lipase or an esterase. The For example, without wishing to be bound by theory, Compounds 1 and 2 shown above may be metabolized as shown in the scheme below:

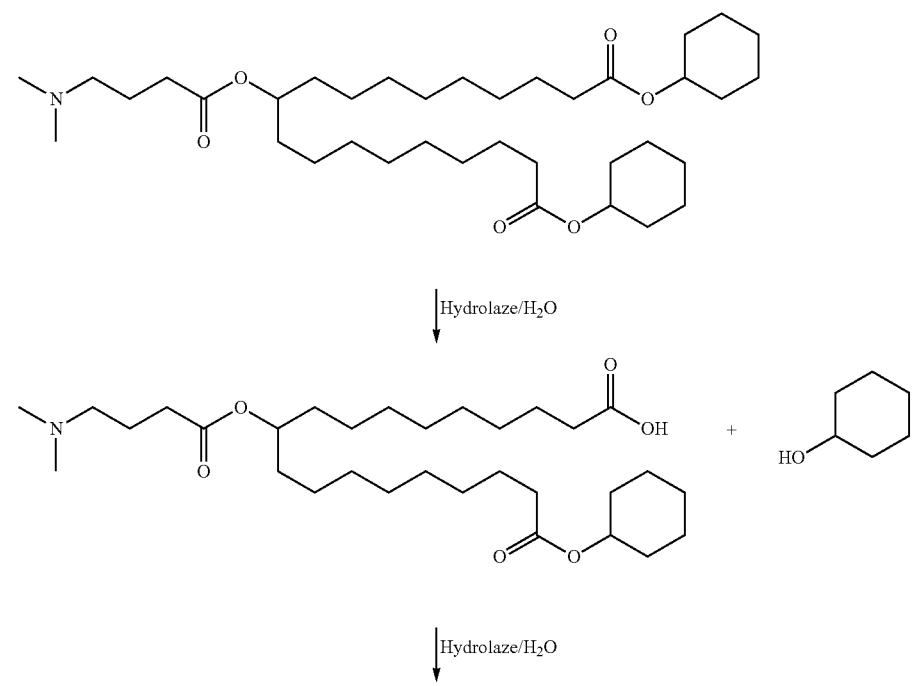

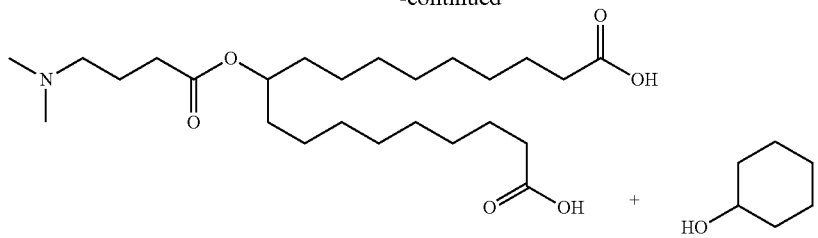

In one embodiment, a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a cationic lipid of any of the embodiments described herein containing a biodegradable group or groups has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Some cationic lipids can be conveniently represented as a hydrophobic group combined with a headgroup. By way of example, the compound:

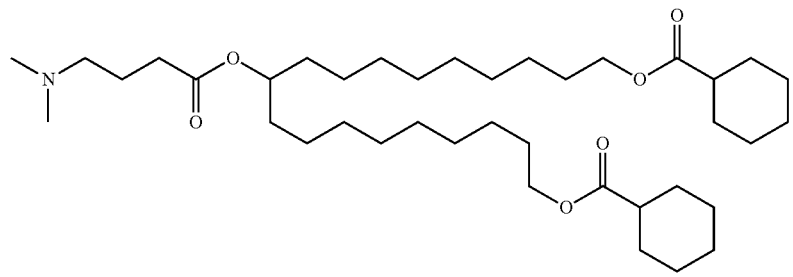 [SMILES: CN(C)CCCC(=O)OC(CCCCCCCCCOC(=O)C1CCCCC1)CCCCCCCCCOC(=O)C1CCCCC1]

can be thought of as a combination of a headgroup and a hydrophobic group as follows:

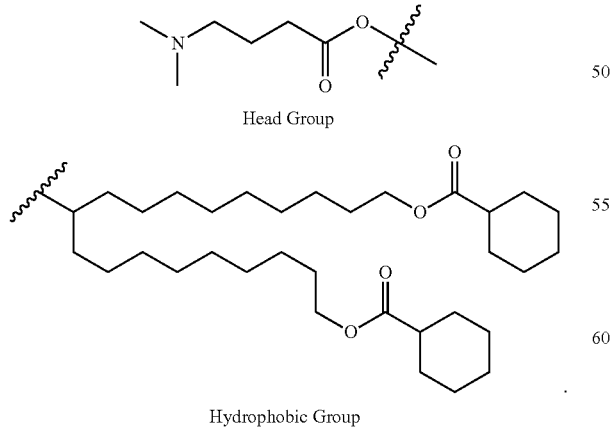

Head Group

Hydrophobic Group

Thus, some suitable head groups include those depicted in Table 1:

TABLE 1

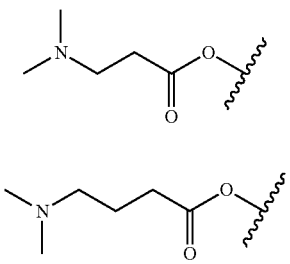

TABLE 1-continued

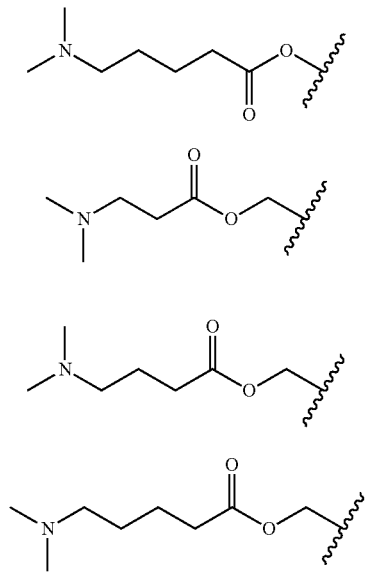

TABLE 1-continued
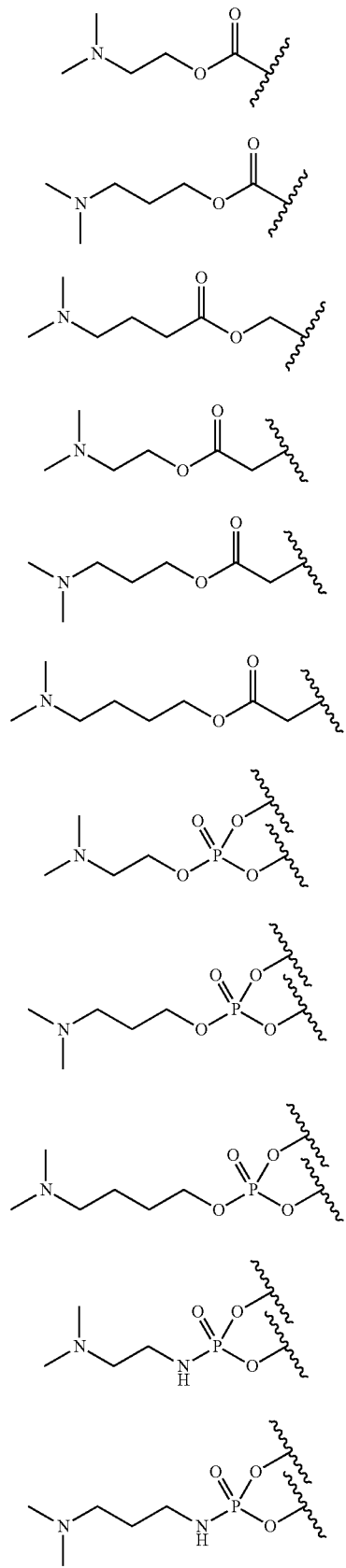
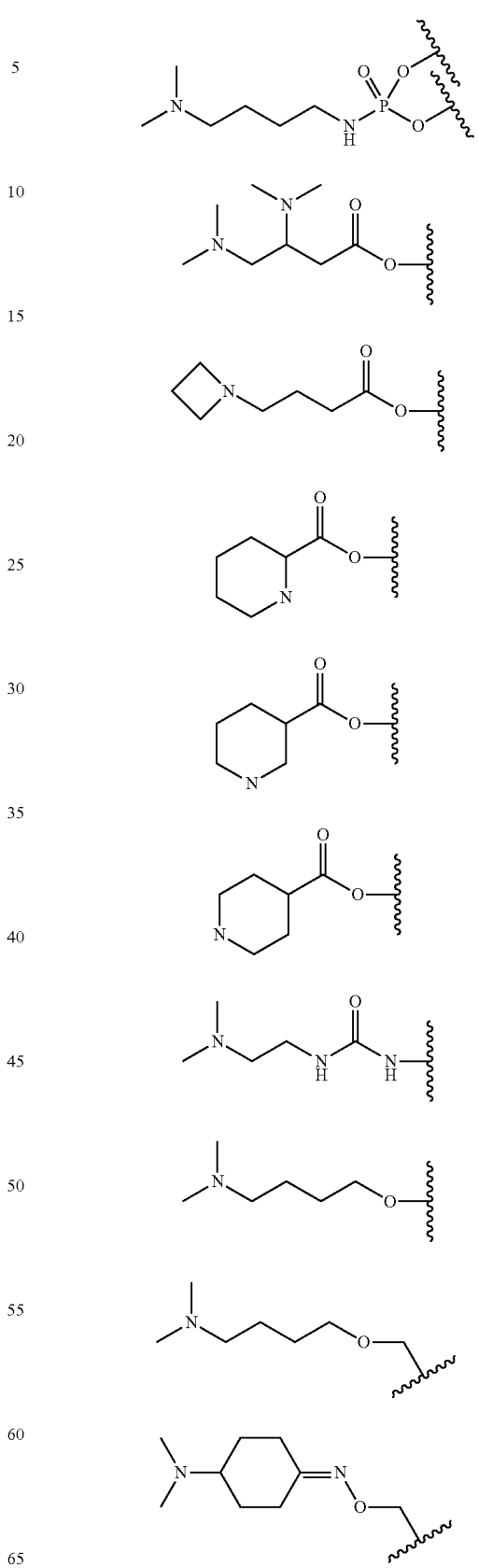

TABLE 1-continued
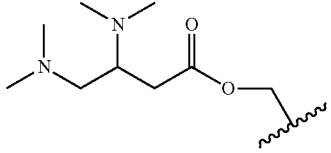 [SMILES: *COC(=O)CC(CN(C)C)N(C)C]
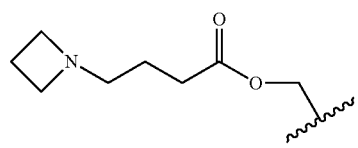 [SMILES: *COC(=O)CCCN1CCC1]
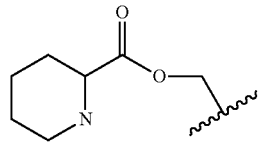 [SMILES: *COC(=O)C1CCCCN1]
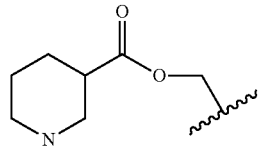 [SMILES: *COC(=O)C1CCCNC1]
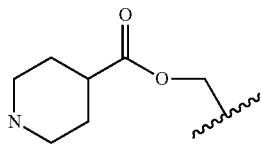 [SMILES: *COC(=O)C1CCNCC1]
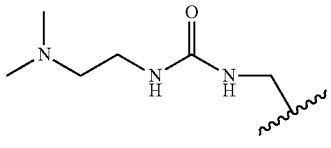 [SMILES: *CNC(=O)NCCN(C)C]
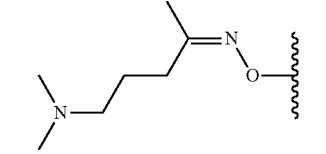 [SMILES: *O/N=C(/C)CCCN(C)C]
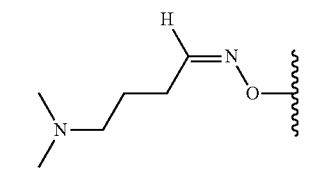 [SMILES: *O/N=C\CCCN(C)C]
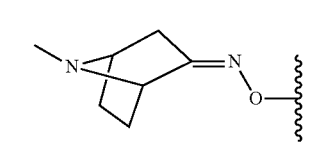 [SMILES: *O/N=C1/CC2CCC1N2C]
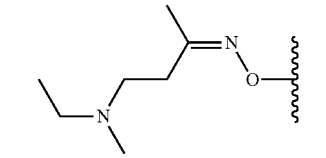 [SMILES: *O/N=C(/C)CCN(C)CC]
TABLE 1-continued
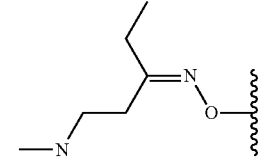
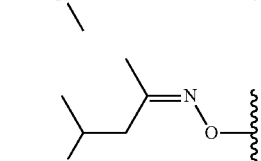
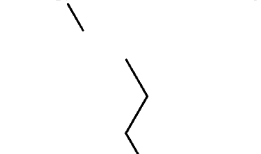
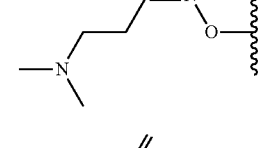
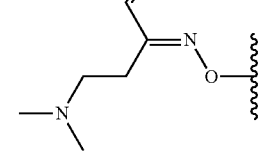
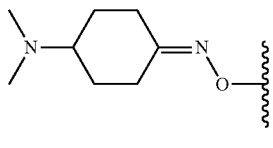 [SMILES: *ON=C1CCC(N(C)C)CC1]
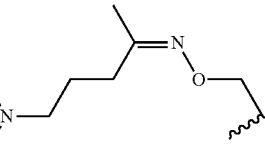
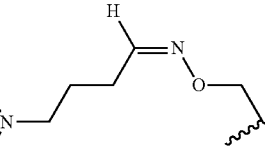
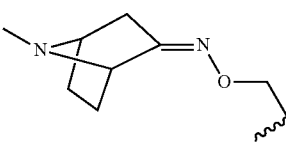
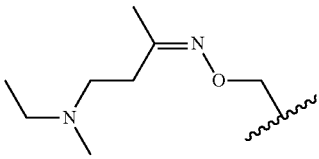 [SMILES: *CO/N=C(/C)CCN(C)CC]

TABLE 1-continued

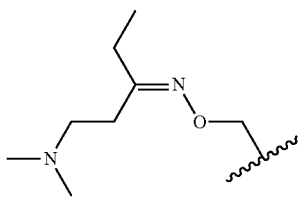 [SMILES: *CO/N=C(/CC)CCN(C)C]

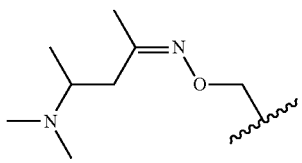 [SMILES: *CO/N=C(/C)CC(C)N(C)C]

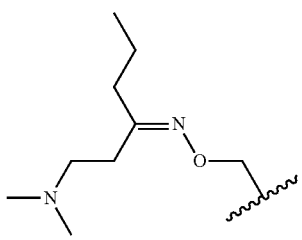 [SMILES: *CO/N=C(/CCC)CCN(C)C]

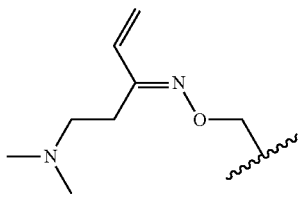 [SMILES: *CO/N=C(/C=C)CCN(C)C]

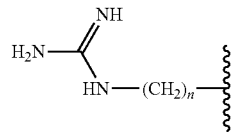

(where n is 0-5)

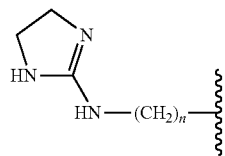

(where n is 0-5)

TABLE 1-continued

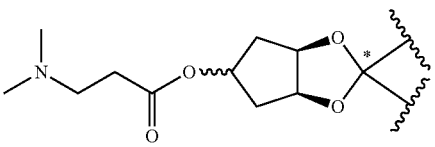

(the carbon with an asterisk is the tertiary carbon of the cation lipid and is not part of the head group)

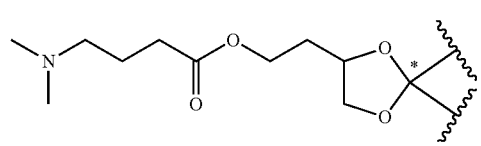

(the carbon with an asterisk is the tertiary carbon of the cation lipid and is not part of the head group)

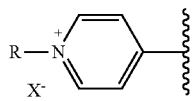

R = H, alkyl (e.g., methyl)
X = halogen (e.g., Cl)

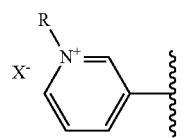

R = H, alkyl (e.g., methyl)
X = halogen (e.g., Cl)

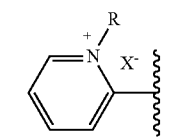

R = H, alkyl (e.g., methyl)
X = halogen (e.g., Cl)

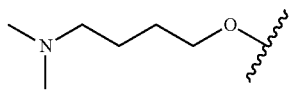 [SMILES: *OCCCCN(C)C]

Some suitable hydrophobic tail groups include those depicted in Table 2:

TABLE 2

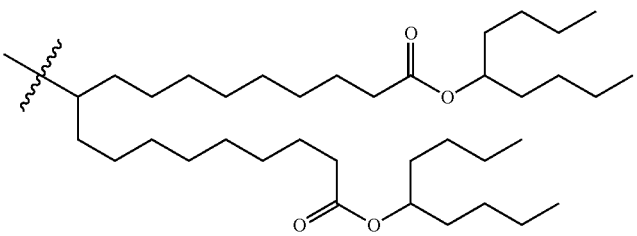 [SMILES: *C(CCCCCCCCC(=O)OC(CCCC)CCCC)CCCCCCCCC(=O)OC(CCCC)CCCC]

TABLE 2-continued
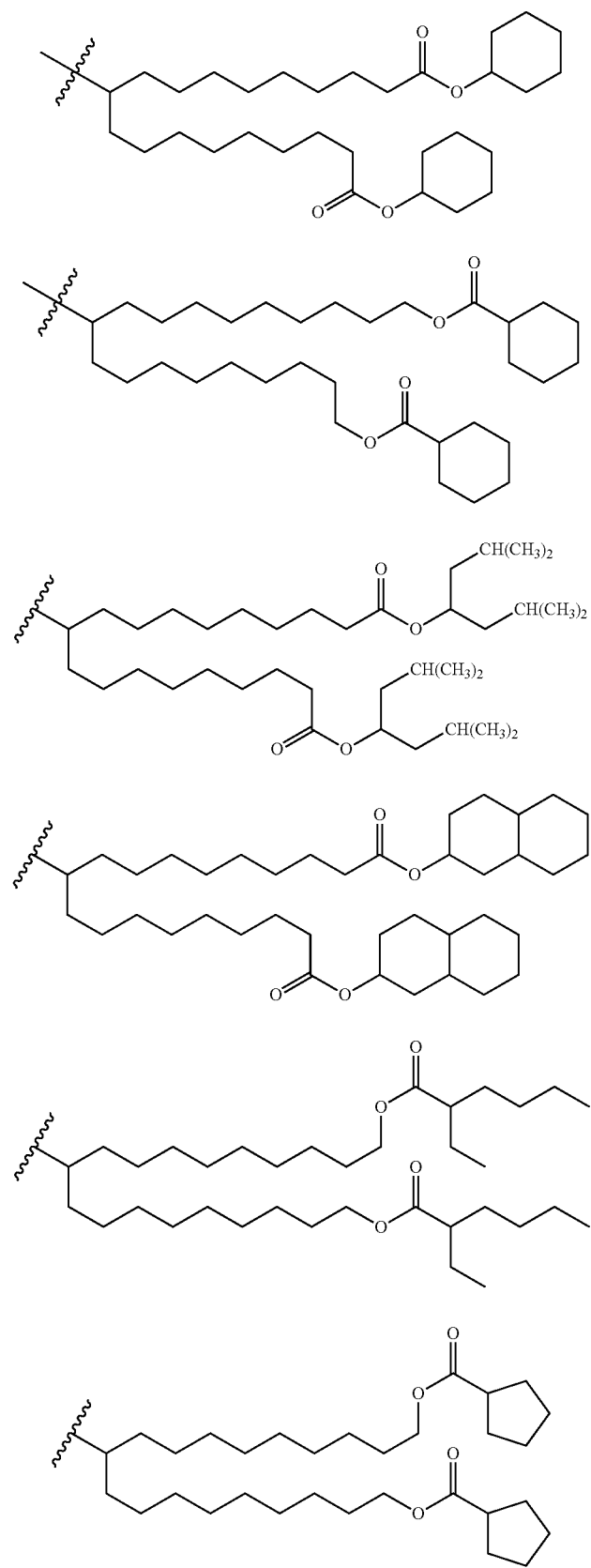

TABLE 2-continued
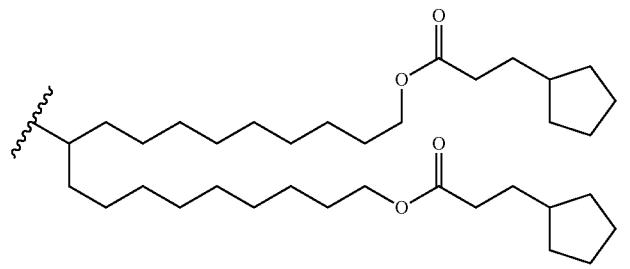 [SMILES: *C(CCCCCCCCCOC(=O)CCC1CCCC1)CCCCCCCCCOC(=O)CCC1CCCC1]
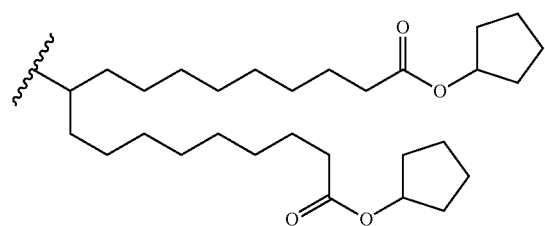 [SMILES: *C(CCCCCCCCC(=O)OC1CCCC1)CCCCCCCCC(=O)OC1CCCC1]
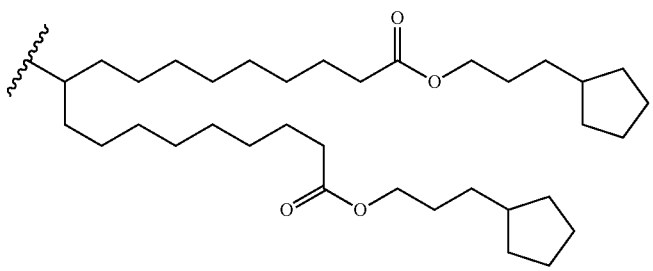 [SMILES: *C(CCCCCCCCC(=O)OCCCC1CCCC1)CCCCCCCCC(=O)OCCCC1CCCC1]
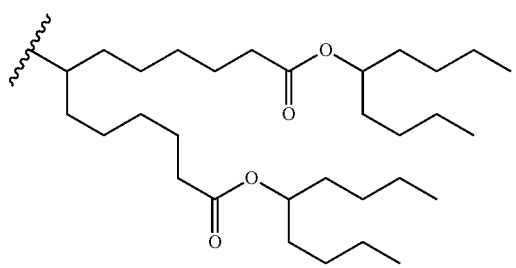 [SMILES: *C(CCCCCC(=O)OC(CCCC)CCCC)CCCCCC(=O)OC(CCCC)CCCC]
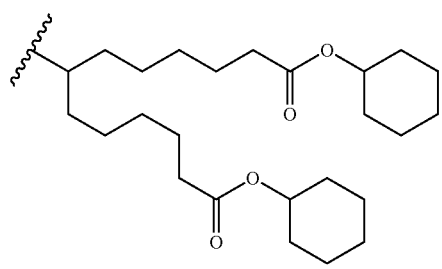 [SMILES: *C(CCCCCC(=O)OC1CCCCC1)CCCCCC(=O)OC1CCCCC1]
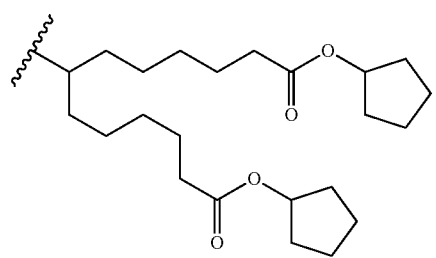 [SMILES: *C(CCCCCC(=O)OC1CCCC1)CCCCCC(=O)OC1CCCC1]

TABLE 2-continued
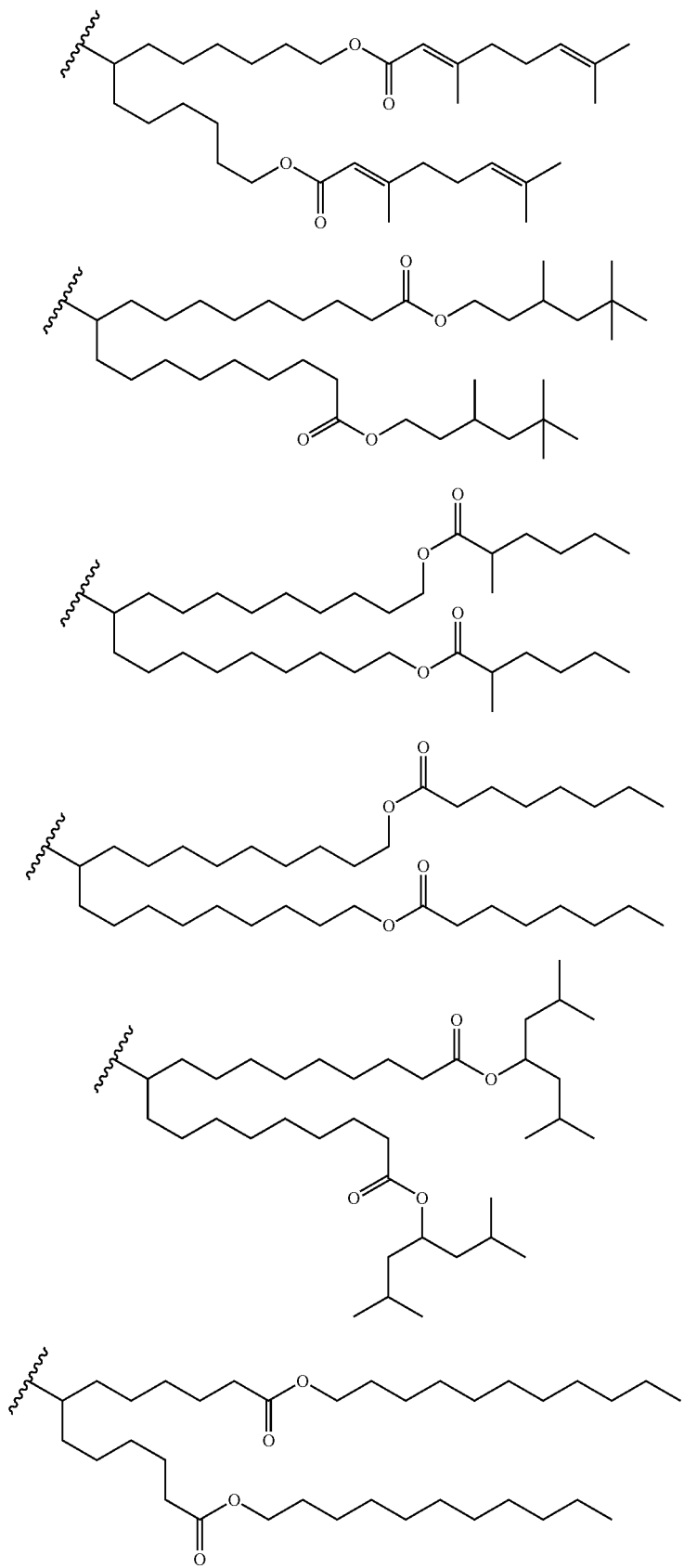

TABLE 2-continued
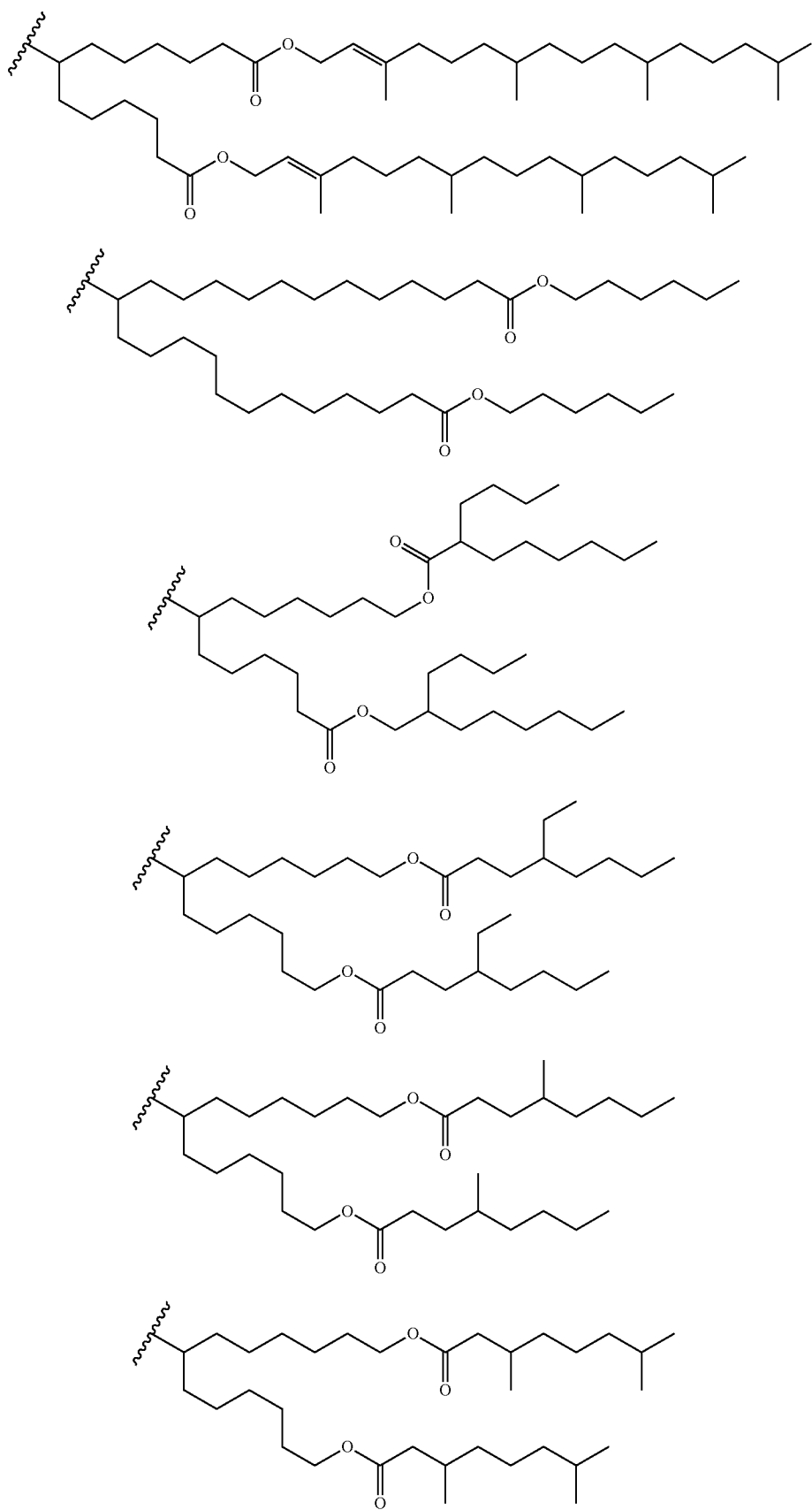

TABLE 2-continued
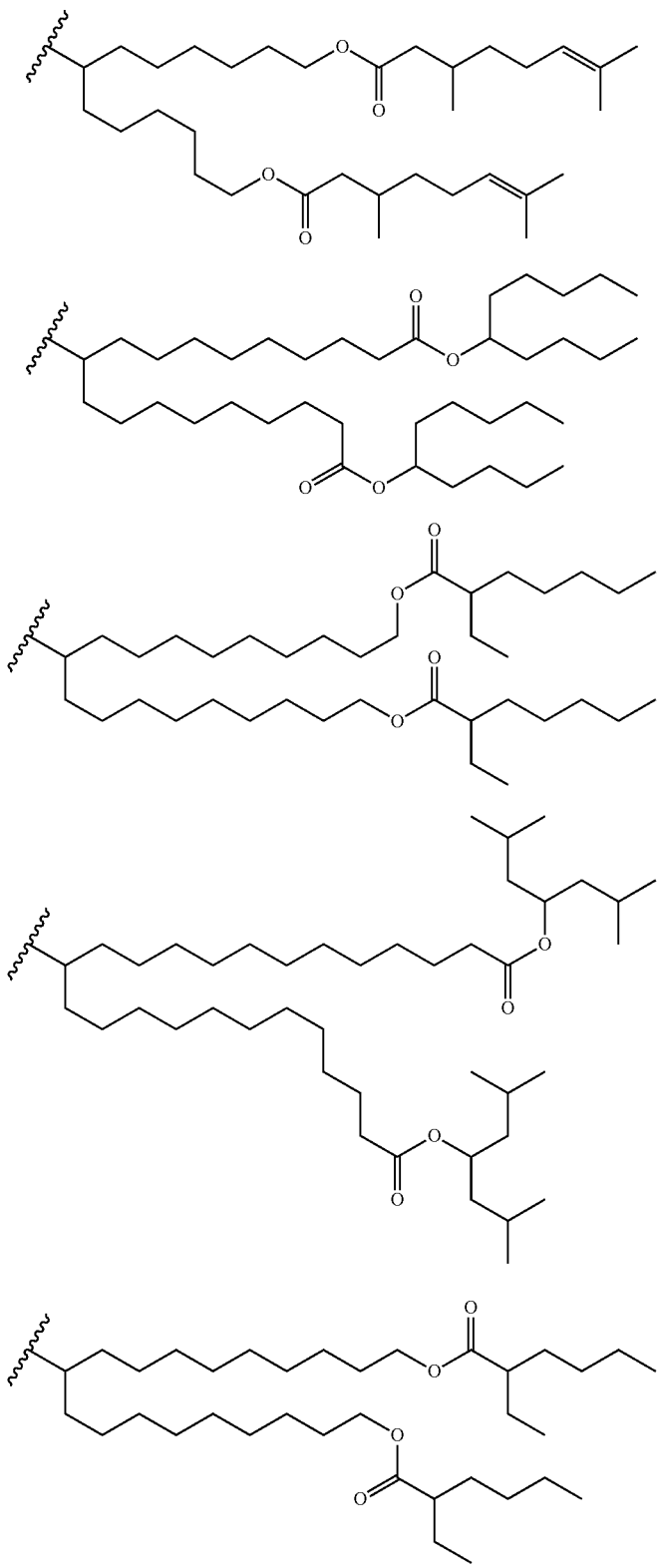
In another aspect, the present invention relates to a method of preparing a compound of Formula I. Suitable exemplary synthetic methods are illustrated in Schemes 1 and 2 below. The variables in the schemes below are the same as those variables at the same position in Formula I above.

The compounds of the present invention (for example, where $M_1$ and/or $M_2$ are —OC(O)—) may be prepared by Scheme 1 shown below.
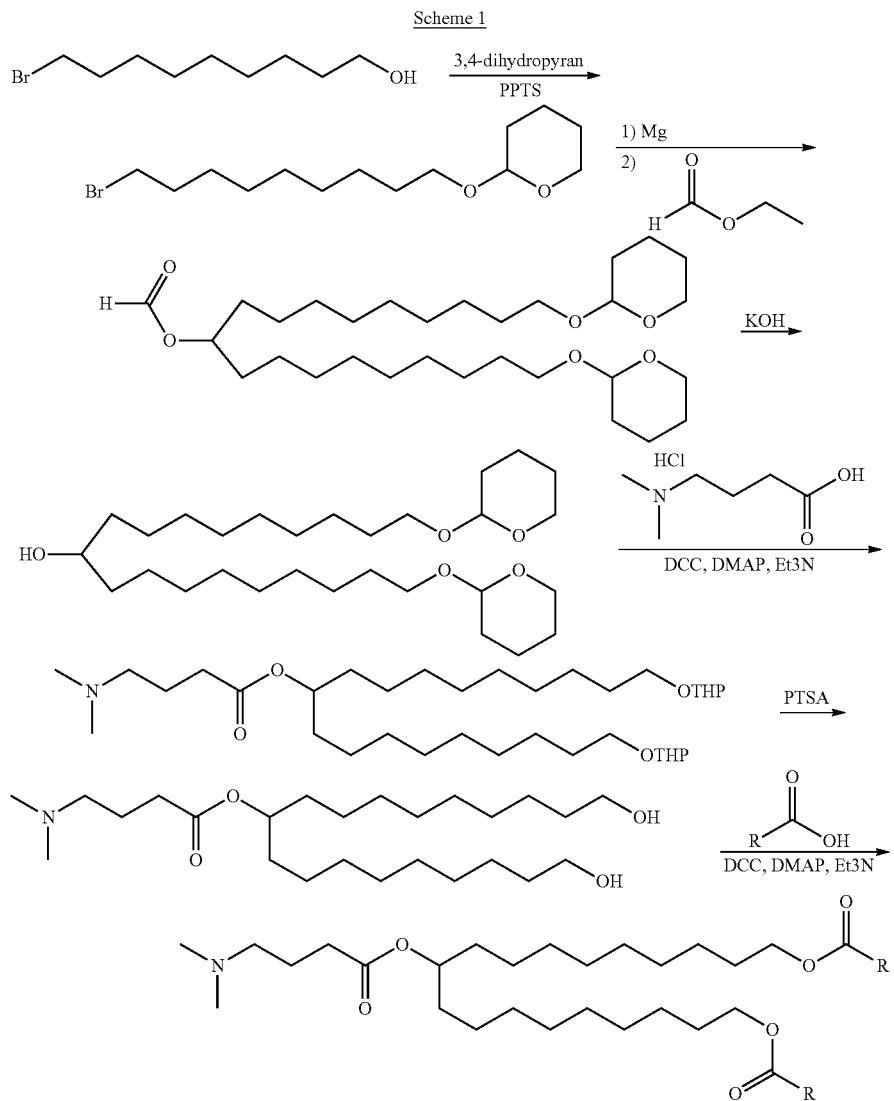
Another method of preparing the compounds of the present invention (for example, where $M_1$ and/or $M_2$ are —C(O)O—) is shown in Scheme 2 below.
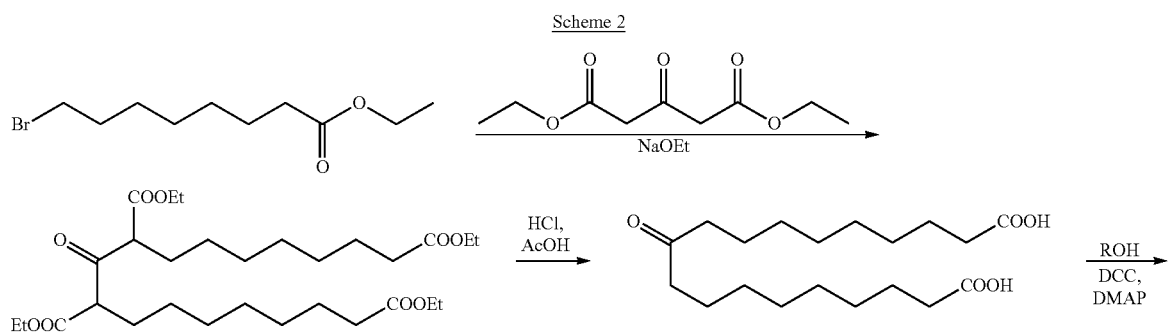

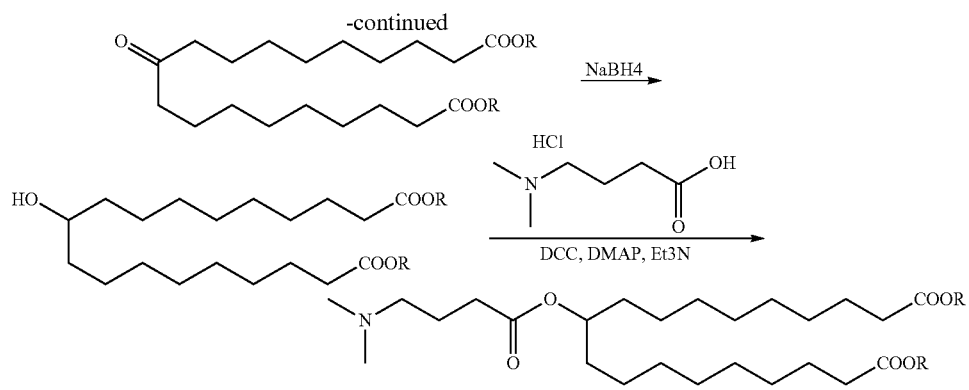
In one embodiment, the cationic lipid of the present invention is selected from the following compounds, and salts thereof (including pharmaceutically acceptable salts thereof):
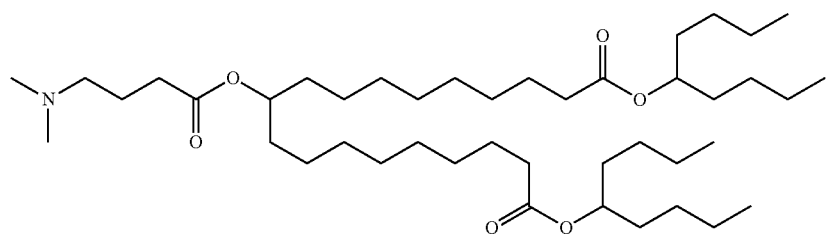
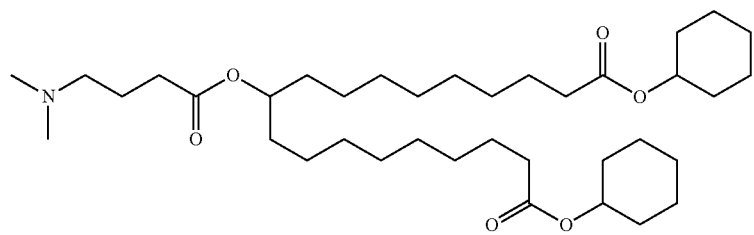
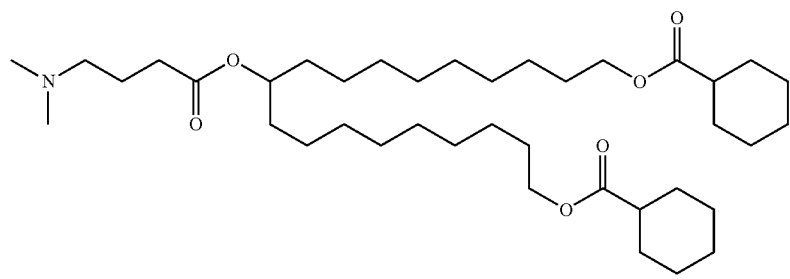
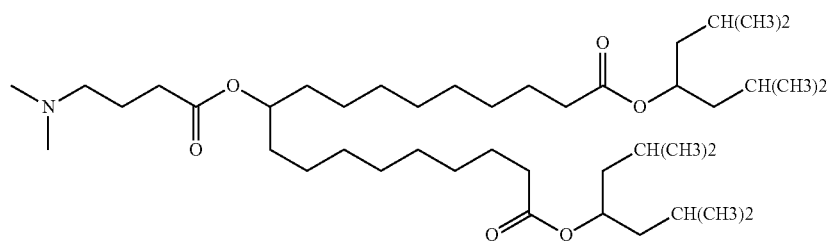

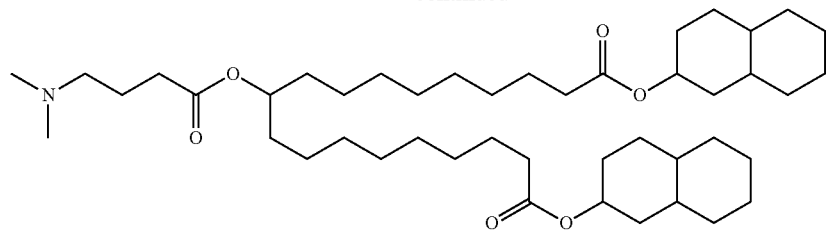
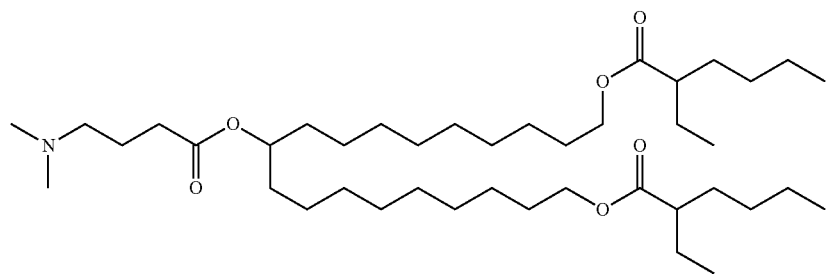 [SMILES: CCCCC(CC)C(=O)OCCCCCCCCCC(CCCCCCCCCOC(=O)C(CC)CCCC)OC(=O)CCCN(C)C]
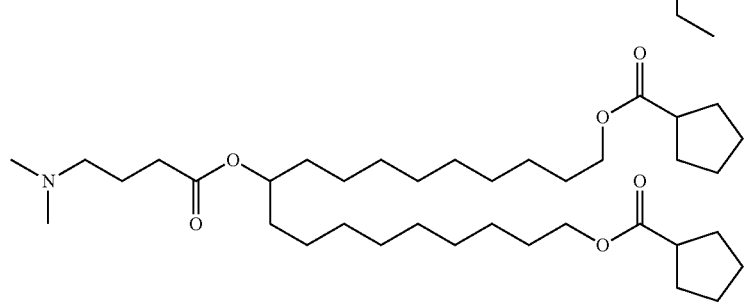
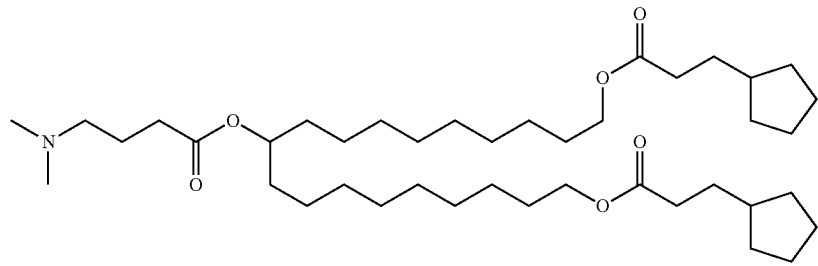
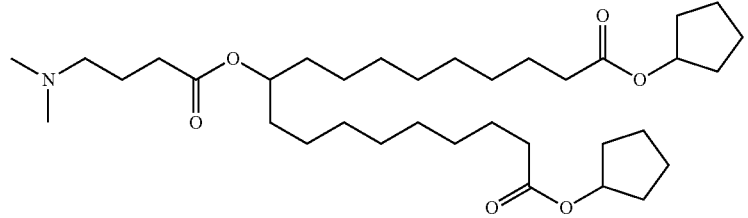
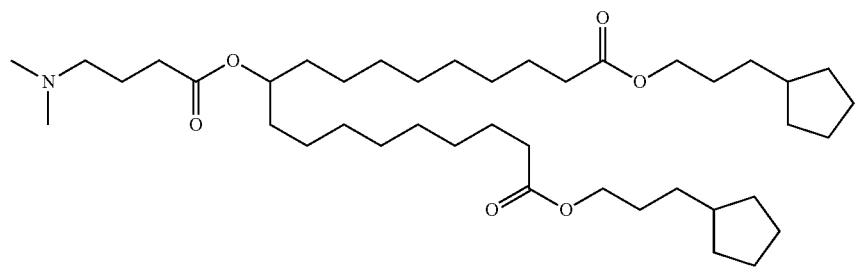

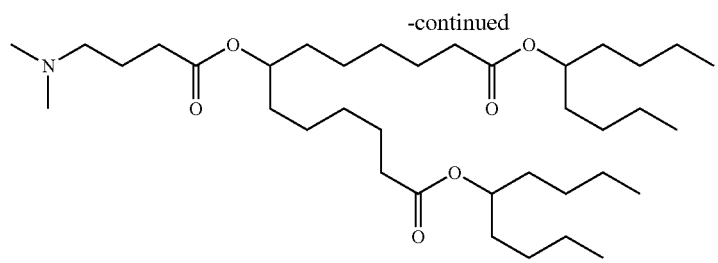
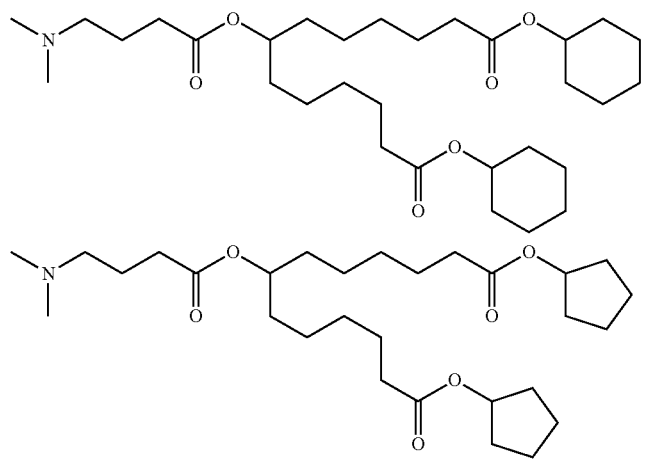
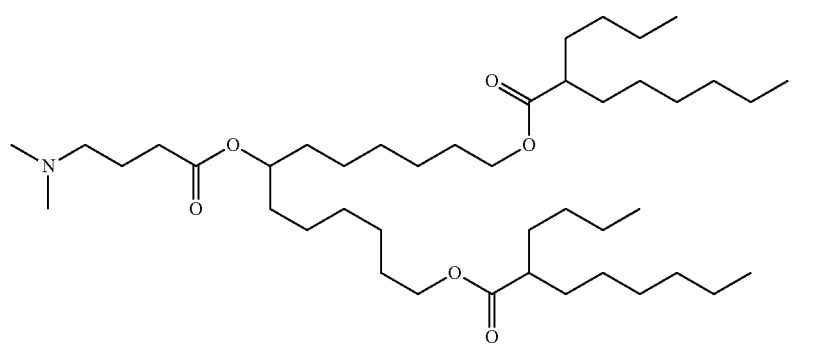
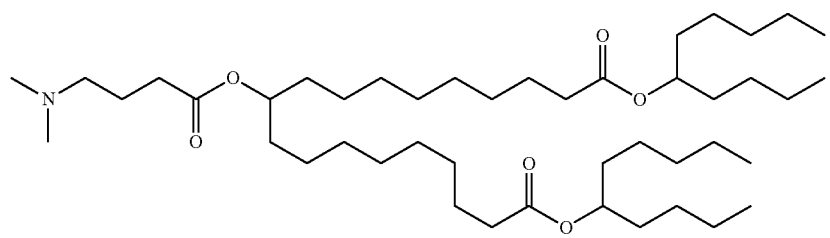
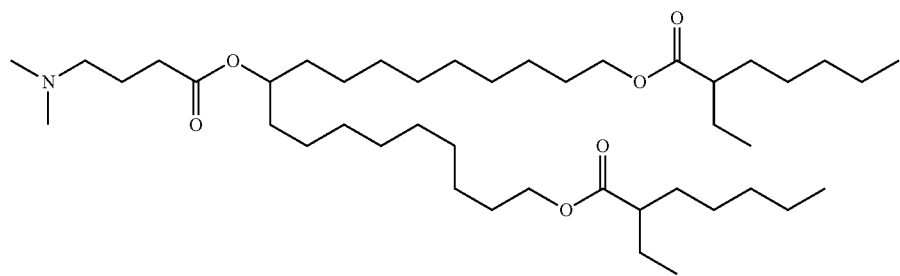

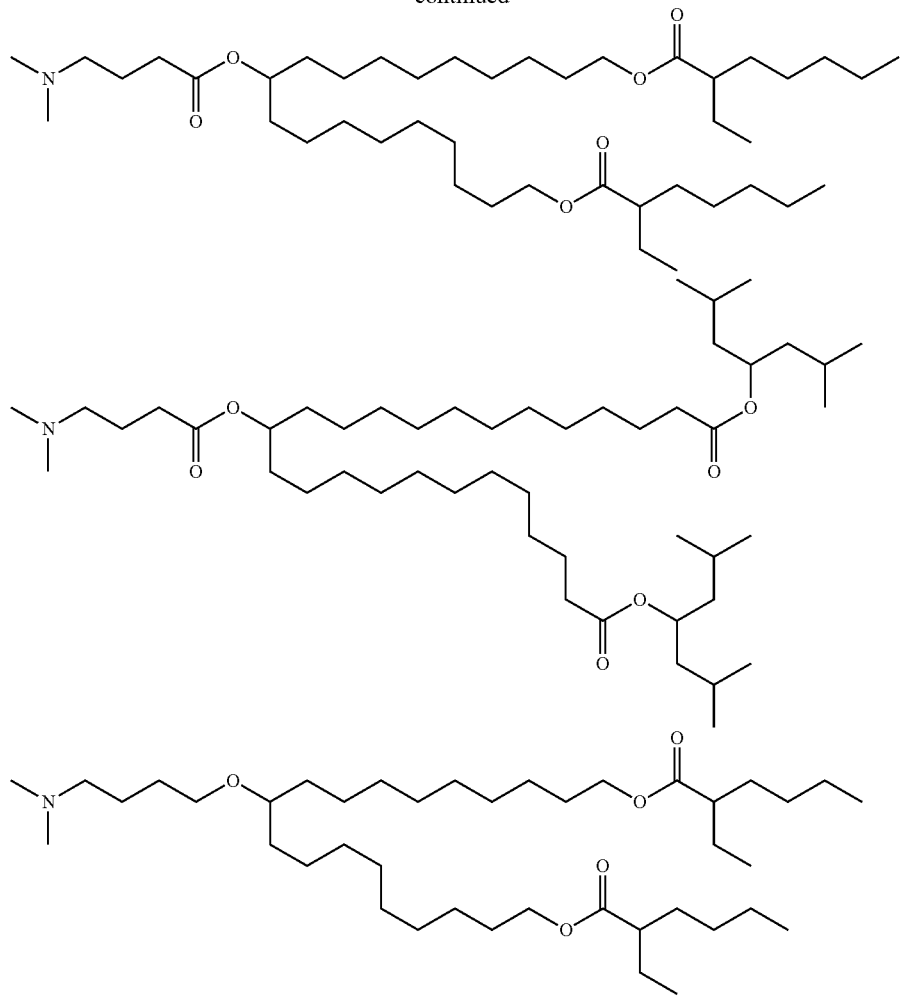
In another embodiment, the cationic lipid of the present invention is selected from the following compound, and salts thereof (including pharmaceutically acceptable salts thereof):
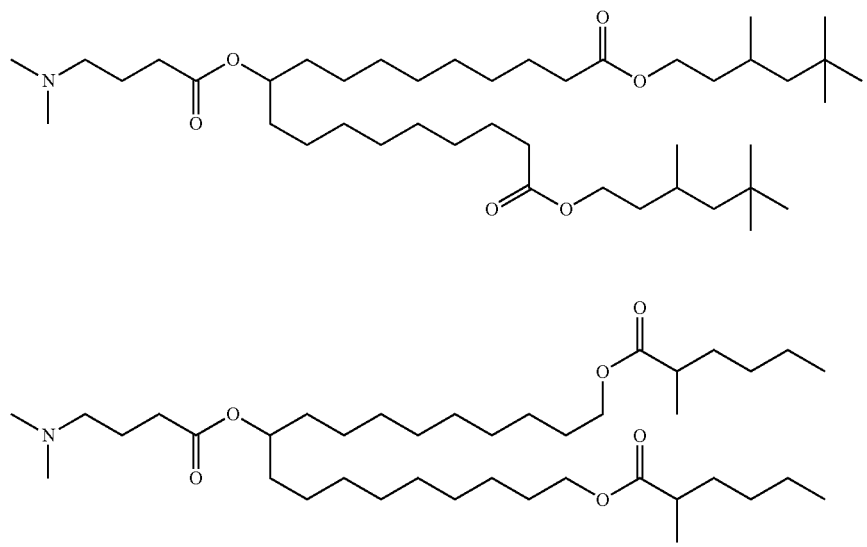

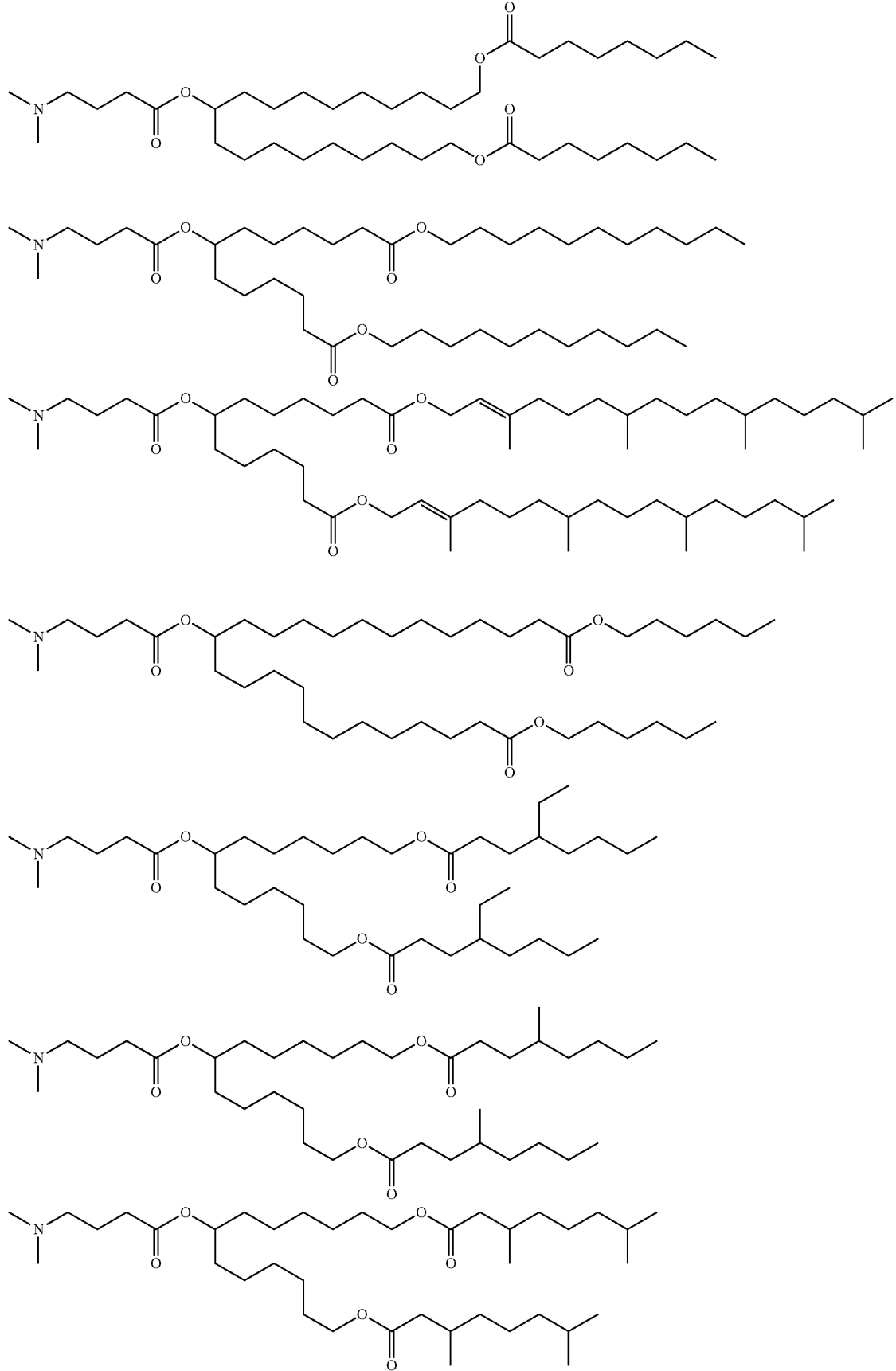

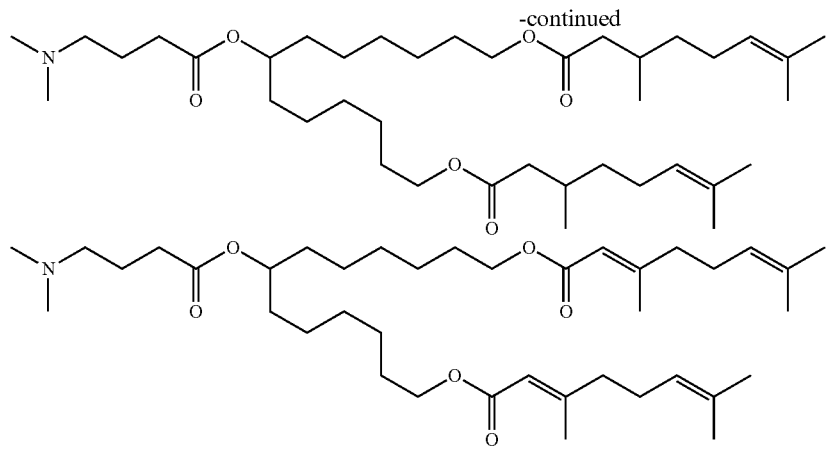

Cationic lipids include those having alternative fatty acid groups and other dialkylamino groups than those shown, including those in which the alkyl substituents are different (e.g., N-ethyl-N-methylamino-, and N-propyl-N-ethyl-amino-).

In certain embodiments, the cationic lipids have at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. The lipids can have more than one protonatable or deprotonatable group, or can be zwiterrionic.

In certain embodiments, protonatable lipids (i.e., cationic lipids) have a $pK_a$ of the protonatable group in the range of about 4 to about 11. For example, the lipids can have a $pK_a$ of about 4 to about 7, e.g., from about 5 to about 7, such as from about 5.5 to about 6.8, when incorporated into lipid particles. Such lipids may be cationic at a lower pH formulation stage, while particles will be largely (though not completely) surface neutralized at physiological pH around pH 7.4.

In particular embodiments, the lipids are charged lipids. As used herein, the term "charged lipid" includes, but is not limited to, those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine).

Included in the instant invention is the free form of the cationic lipids described herein, as well as pharmaceutically acceptable salts and stereoisomers thereof. The cationic lipid can be a protonated salt of the amine cationic lipid. The term "free form" refers to the amine cationic lipids in non-salt form. The free form may be regenerated by treating the salt with a suitable dilute aqueous base solution such as dilute aqueous NaOH, potassium carbonate, ammonia and sodium bicarbonate.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include non-toxic salts of the cationic lipids of this invention as formed by reacting a basic instant cationic lipids with an inorganic or organic acid. For example, non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, and trifluoroacetic (TFA).

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, and zinc. In one embodiment, the base is selected from ammonium, calcium, magnesium, potassium and sodium. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N[1]-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, and tromethamine.

It will also be noted that the cationic lipids of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

One or more additional cationic lipids, which carry a net positive charge at about physiological pH, in addition to those specifically described above, may also be included in the lipid particles and compositions described herein. Such cationic lipids include, but are not limited to N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoroacetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

The Other Lipid Components

The lipid particles and compositions described herein may also include one or more neutral lipids. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. In one embodiment, the neutral lipid component is a lipid having two acyl groups (e.g., diacylphosphatidylcholine and diacylphosphatidylethanolamine). In one embodiment, the neutral lipid contains saturated fatty acids with carbon chain lengths in the range of $C_{10}$ to $C_{20}$. In another embodiment, the neutral lipid includes mono or diunsaturated fatty acids with carbon chain lengths in the range of $C_{10}$ to $C_{20}$. Suitable neutral lipids include, but are not limited to, DSPC, DPPC, POPC, DOPE, DSPC, and SM.

The lipid particles and compositions described herein may also include one or more lipids capable of reducing aggregation. Examples of lipids that reduce aggregation of particles during formation include polyethylene glycol (PEG)-modified lipids (PEG lipids, such as PEG-DMG and PEG-DMA), monosialoganglioside Gm1, and polyamide oligomers ("PAO") such as (described in U.S. Pat. No. 6,320,017, which is incorporated by reference in its entirety). Suitable PEG lipids include, but are not limited to, PEG-modified phosphatidylethanolamine and phosphatidic acid, PEG-ceramide conjugates (e.g., PEG-CerC14 or PEG-CerC20) (such as those described in U.S. Pat. No. 5,820,873, incorporated herein by reference), PEG-modified dialkylamines and PEG-modified 1,2-diacyloxypropan-3-amines, PEG-modified diacylglycerols and dialkylglycerols, mPEG (mw2000)-diastearoylphosphatidylethanolamine (PEG-DSPE).

The lipid particles and compositions may include a sterol, such as cholesterol.

Lipid Particles

In a further aspect, the present invent relates to lipid particles that include one or more of the cationic lipids described herein. In one embodiment, the lipid particle includes one or more compounds of formula I-VII.

Lipid particles include, but are not limited to, liposomes. As used herein, a liposome is a structure having lipid-containing membranes enclosing an aqueous interior.

Another embodiment is a nucleic acid-lipid particle (e.g., a SNALP) comprising a cationic lipid of the present invention, a non-cationic lipid (such as a neutral lipid), optionally a PEG-lipid conjugate (such as the lipids for reducing aggregation of lipid particles discussed herein), and a nucleic acid. As used herein, the term "SNALP" refers to a stable nucleic acid-lipid particle. A SNALP represents a particle made from lipids, wherein the nucleic acid (e.g., an interfering RNA) is encapsulated within the lipids. In certain instances, SNALPs are useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in International Publication No. WO 00/03683, the disclosure of which is herein incorporated by reference in its entirety.

For example, the lipid particle may include a cationic lipid, a fusion-promoting lipid (e.g., DPPC), a neutral lipid, cholesterol, and a PEG-modified lipid. In one embodiment, the lipid particle includes the above lipid mixture in molar ratios of about 20-70% cationic lipid: 0.1-50% fusion promoting lipid: 5-45% neutral lipid: 20-55% cholesterol: 0.5-15% PEG-modified lipid.

In another embodiment of the lipid particle, the cationic lipid is present in a mole percentage of about 20% and about 60%; the neutral lipid is present in a mole percentage of about 5% to about 25%; the sterol is present in a mole percentage of about 25% to about 55%; and the PEG lipid is PEG-DMA, PEG-DMG, or a combination thereof, and is present in a mole percentage of about 0.5% to about 15%.

In particular embodiments, the molar lipid ratio, with regard to mol % cationic lipid/DSPC/Chol/PEG-DMG or PEG-DMA) is approximately 40/10/40/10, 35/15/40/10 or 52/13/30/5. This mixture may be further combined with a fusion-promoting lipid in a molar ratio of 0.1-50%, 0.1-50%, 0.5-50%, 1-50%, 5%-45%, 10%-40%, or 15%-35%. In other words, when a 40/10/40/10 mixture of lipid/DSPC/Chol/PEG-DMG or PEG-DMA is combined with a fusion-promoting peptide in a molar ratio of 50%, the resulting lipid particles can have a total molar ratio of (mol % cationic lipid/DSPC/Chol/PEG-DMG or PEG-DMA/fusion-promoting peptide) 20/5/20/5/50. In another embodiment, the neutral lipid, DSPC, in these compositions is replaced with POPC, DPPC, DOPE or SM.

In one embodiment, the lipid particles comprise a cationic lipid of the present invention, a neutral lipid, a sterol and a PEG-modified lipid. In one embodiment, the lipid particles include from about 25% to about 75% on a molar basis of cationic lipid, e.g., from about 35 to about 65%, from about 45 to about 65%, about 60%, about 57.5%, about 57.1%, about 50% or about 40% on a molar basis. In one embodiment, the lipid particles include from about 0% to about 15% on a molar basis of the neutral lipid, e.g., from about 3 to about 12%, from about 5 to about 10%, about 15%, about 10%, about 7.5%, about 7.1% or about 0% on a molar basis. In one embodiment, the neutral lipid is DPPC. In one embodiment, the neutral lipid is DSPC.

In one embodiment, the formulation includes from about 5% to about 50% on a molar basis of the sterol, e.g., about 15 to about 45%, about 20 to about 40%, about 48%, about 40%, about 38.5%, about 35%, about 34.4%, about 31.5% or about 31% on a molar basis. In one embodiment, the sterol is cholesterol.

The lipid particles described herein may further include one or more therapeutic agents. In a preferred embodiment, the lipid particles include a nucleic acid (e.g., an oligonucleotide), such as siRNA or miRNA.

In one embodiment, the lipid particles include from about 0.1% to about 20% on a molar basis of the PEG-modified lipid, e.g., about 0.5 to about 10%, about 0.5 to about 5%, about 10%, about 5%, about 3.5%, about 1.5%, about 0.5%, or about 0.3% on a molar basis. In one embodiment, the PEG-modified lipid is PEG-DMG. In one embodiment, the PEG-modified lipid is PEG-c-DMA. In one embodiment, the lipid particles include 25-75% of cationic lipid, 0.5-15% of the neutral lipid, 5-50% of the sterol, and 0.5-20% of the PEG-modified lipid on a molar basis.

In one embodiment, the lipid particles include 35-65% of cationic lipid, 3-12% of the neutral lipid, 15-45% of the sterol, and 0.5-10% of the PEG-modified lipid on a molar basis. In one embodiment, the lipid particles include 45-65% of cationic lipid, 5-10% of the neutral lipid, 25-40% of the sterol, and 0.5-5% of the PEG-modified lipid on a molar basis. In one embodiment, the PEG modified lipid comprises a PEG molecule of an average molecular weight of 2,000 Da. In one embodiment, the PEG modified lipid is PEG-distyryl glycerol (PEG-DSG).

In one embodiment, the ratio of lipid:siRNA is at least about 0.5:1, at least about 1:1, at least about 2:1, at least about 3:1, at least about 4:1, at least about 5:1, at least about 6:1, at least about 7:1, at least about 11:1 or at least about 33:1. In one embodiment, the ratio of lipid:siRNA ratio is between about 1:1 to about 35:1, about 3:1 to about 15:1, about 4:1 to about 15:1, or about 5:1 to about 13:1. In one embodiment, the ratio of lipid:siRNA ratio is between about 0.5:1 to about 12:1.

In one embodiment, the lipid particles are nanoparticles. In additional embodiments, the lipid particles have a mean diameter size of from about 50 nm to about 300 nm, such as from about 50 nm to about 250 nm, for example, from about 50 nm to about 200 nm.

In one embodiment, a lipid particle containing a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a lipid particle containing a cationic lipid of any of the embodiments described herein has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Additional Components

The lipid particles and compositions described herein can further include one or more antioxidants. The antioxidant stabilizes the lipid particle and prevents, decreases, and/or inhibits degradation of the cationic lipid and/or active agent present in the lipid particles. The antioxidant can be a hydrophilic antioxidant, a lipophilic antioxidant, a metal chelator, a primary antioxidant, a secondary antioxidant, salts thereof, and mixtures thereof. In certain embodiments, the antioxidant comprises a metal chelator such as EDTA or salts thereof, alone or in combination with one, two, three, four, five, six, seven, eight, or more additional antioxidants such as primary antioxidants, secondary antioxidants, or other metal chelators. In one preferred embodiment, the antioxidant comprises a metal chelator such as EDTA or salts thereof in a mixture with one or more primary antioxidants and/or secondary antioxidants. For example, the antioxidant may comprise a mixture of EDTA or a salt thereof, a primary antioxidant such as a-tocopherol or a salt thereof, and a secondary antioxidant such as ascorbyl palmitate or a salt thereof. In one embodiment, the antioxidant comprises at least about 100 mM citrate or a salt thereof. Examples of antioxidants include, but are not limited to, hydrophilic antioxidants, lipophilic antioxidants, and mixtures thereof. Non-limiting examples of hydrophilic antioxidants include chelating agents (e.g., metal chelators) such as ethylenediaminetetraacetic acid (EDTA), citrate, ethylene glycol tetraacetic acid (EGTA), 1,2-bis(o-aminophenoxy) ethane-N,N,N',N'-tetraacetic acid (BAPTA), diethylene triamine pentaacetic acid (DTPA), 2,3-dimercapto-1-propanesulfonic acid (DMPS), dimercaptosuccinic acid (DMSA), cc-lipoic acid, salicylaldehyde isonicotinoyl hydrazone (SIH), hexyl thioethylamine hydrochloride (HTA), desferrioxamine, salts thereof, and mixtures thereof. Additional hydrophilic antioxidants include ascorbic acid, cysteine, glutathione, dihydrolipoic acid, 2-mercaptoethane sulfonic acid, 2-mercaptobenzimidazole sulfonic acid, 6-hydroxy-2, 5,7,8-tetramethylchroman-2-carboxylic acid, sodium metabisulfite, salts thereof, and mixtures thereof. Non-limiting examples of lipophilic antioxidants include vitamin E isomers such as $\alpha$-, $\beta$-, $\gamma$-, and $\delta$-tocopherols and $\alpha$-, $\beta$-, $\gamma$-, and $\delta$-tocotrienols; polyphenols such as 2-tert-butyl-4-methyl phenol, 2-tert-butyl-5-methyl phenol, and 2-tert-butyl-6-methyl phenol; butylated hydroxyanisole (BHA) (e.g., 2-teri-butyl-4-hydroxyanisole and 3-tert-butyl-4-hydroxyanisole); butylhydroxytoluene (BHT); tert-butylhydroquinone (TBHQ); ascorbyl palmitate; rc-propyl gallate; salts thereof; and mixtures thereof. Suitable antioxidants and formulations containing such antioxidants are described in International Publication No. WO 2011/066651, which is hereby incorporated by reference.

In another embodiment, the lipid particles or compositions contain the antioxidant EDTA (or a salt thereof), the antioxidant citrate (or a salt thereof), or EDTA (or a salt thereof) in combination with one or more (e.g., a mixture of) primary and/or secondary antioxidants such as α-tocopherol (or a salt thereof) and/or ascorbyl palmitate (or a salt thereof).

In one embodiment, the antioxidant is present in an amount sufficient to prevent, inhibit, or reduce the degradation of the cationic lipid present in the lipid particle. For example, the antioxidant may be present at a concentration of at least about or about 0.1 mM, 0.5 mM, 1 mM, 10 mM, 100 mM, 500 mM, 1 M, 2 M, or 5M, or from about 0.1 mM to about 1 M, from about 0.1 mM to about 500 mM, from about 0.1 mM to about 250 mM, or from about 0.1 mM to about 100 mM.

The lipid particles and compositions described herein can further include an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

In a preferred embodiment, the active agent is a nucleic acid, such as a siRNA. For example, the active agent can be a nucleic acid encoded with a product of interest, including but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, vaccines and small molecules or mixtures thereof. In one more preferred embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long. In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression.

The nucleic acid that is present in a lipid-nucleic acid particle can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The lipid particles of the present invention can also deliver nucleic acids which are conjugated to one or more ligands.

Pharmaceutical Compositions

The lipid particles, particularly when associated with a therapeutic agent, may be formulated as a pharmaceutical composition, e.g., which further comprises a pharmaceutically acceptable diluent, excipient, or carrier, such as physiological saline or phosphate buffer.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary, for example, from less than about 0.01%, to at or at least about 0.05-5% to as much as 10 to 30% by weight.

Methods of Manufacture

Methods of making cationic lipids, lipid particles containing them, and pharmaceutical compositions containing the cationic lipids and/or lipid particles are described in, for example, International Publication Nos. WO 2010/054406, WO 2010/054401, WO 2010/054405, WO 2010/054384, WO 2010/042877, WO 2010/129709, WO 2009/086558, and WO 2008/042973, and U.S. Patent Publication Nos. 2004/0142025, 2006/0051405 and 2007/0042031, each of which is incorporated by reference in its entirety.

For example, in one embodiment, a solution of one or more lipids (including a cationic lipid of any of the embodiments described herein) in an organic solution (e.g., ethanol) is prepared. Similarly, a solution of one or more active (therapeutic) agents (such as, for example an siRNA molecule or a 1:1 molar mixture of two siRNA molecules) in an aqueous buffered (e.g., citrate buffer) solution is prepared. The two solutions are mixed and diluted to form a colloidal suspension of siRNA lipid particles. In one embodiment, the siRNA lipid particles have an average particle size of about 80-90 nm. In further embodiments, the dispersion may be filtered through 0.45/2 micron filters, concentrated and diafiltered by tangential flow filtration.

DEFINITIONS

As used herein, the term "cationic lipid" includes those lipids having one or two fatty acid or fatty aliphatic chains and an amino acid containing head group that may be protonated to form a cationic lipid at physiological pH. In some embodiments, a cationic lipid is referred to as an "amino acid conjugate cationic lipid."

A subject or patient in whom administration of the complex is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats, avian species, such as chickens, turkeys, and songbirds, i.e., for veterinary medical use.

Many of the chemical groups recited in the generic formulas above are written in a particular order (for example, —OC(O)—). It is intended that the chemical group is to be incorporated into the generic formula in the order presented unless indicated otherwise. For example, a generic formula of the form —(R)$_i$-(M$^1$)$_k$-(R)$_m$— where M$^1$ is —C(O)O— and k is 1 refers to —(R)$_i$—C(O)O—(R)$_m$— unless specified otherwise. It is to be understood that when a chemical group is written in a particular order, the reverse order is also contemplated unless otherwise specified. For example, in a generic formula —(R)$_i$-(M$^1$)$_k$-(R)$_m$— where M$^1$ is defined as —C(O)NH— (i.e., —(R)$_i$—C(O)—NH—(R)$_m$—), the compound where M$^1$ is —NHC(O)— (i.e., —(R)$_i$—NHC(O)—(R)$_m$—) is also contemplated unless otherwise specified.

As used herein, the term "biodegradable group" refers to a group that include one or more bonds that may undergo bond breaking reactions in a biological environment, e.g., in an organism, organ, tissue, cell, or organelle. For example, the biodegradable group may be metabolizable by the body of a mammal, such as a human (e.g., by hydrolysis). Some groups that contain a biodegradable bond include, for example, but are not limited to esters, dithiols, and oximes. Non-limiting examples of biodegradable groups are —OC(O)—, —C(O)O—, —SC(O)—, —C(O)S—, —OC(S)—, —C(S)O—, —S—S—, —C(R$^5$)=N—, —N=C(R$^5$)—, —C(R$^5$)=N—O—, —O—N=C(R$^5$)—, —C(O)(NR$^5$)—, —N(R$^5$)C(O)—, —C(S)(NR$^5$)—, —N(R$^5$)C(O)—, —N(R$^5$)C(O)N(R$^5$)—, —OC(O)O—, —OSi(R$^5$)$_2$O—, —C(O)(CR$^3$R$^4$)C(O)O—, or —OC(O)(CR$^3$R$^4$)C(O)—.

As used herein, an "aliphatic" group is a non-aromatic group in which carbon atoms are linked into chains, and is either saturated or unsaturated.

The terms "alkyl" and "alkylene" refer to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include methyl, ethyl, n-propyl, n-butyl, n-pentyl, and n-hexyl. Representative saturated branched alkyl groups include isopropyl, sec-butyl, isobutyl, tert-butyl, and isopentyl.

The term "alkenyl" refers to a straight or branched chain hydrocarbon moiety having one or more carbon-carbon double bonds. In one embodiment, the alkenyl group contains 1, 2, or 3 double bonds and is otherwise saturated. Unless otherwise specified, the "alkenyl" group contains from 2 to 24 carbon atoms. Alkenyl groups include both cis and trans isomers. Representative straight chain and branched alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

The term "alkynyl" refers to a straight or branched chain hydrocarbon moiety having one or more carbon-carbon triple bonds. Unless otherwise specified, the "alkynyl" group contains from 2 to 24 carbon atoms. Representative straight chain and branched alkynyl groups include acetylenyl, propynyl, 1-butynyl, 2-butynyl, 1-pentynyl, 2-pentynyl, and 3-methyl-1-butynyl.

Unless otherwise specified, the term "acyl" refers to a carbonyl group substituted with hydrogen, alkyl, partially saturated or fully saturated cycloalkyl, partially saturated or fully saturated heterocycle, aryl, or heteroaryl. For example, acyl groups include groups such as ($C_1$-$C_{20}$)alkanoyl (e.g., formyl, acetyl, propionyl, butyryl, valeryl, caproyl, and t-butylacetyl), ($C_3$-$C_{20}$)cycloalkylcarbonyl (e.g., cyclopropylcarbonyl, cyclobutylcarbonyl, cyclopentylcarbonyl, and cyclohexylcarbonyl), heterocyclic carbonyl (e.g., pyrrolidinylcarbonyl, pyrrolid-2-one-5-carbonyl, piperidinylcarbonyl, piperazinylcarbonyl, and tetrahydrofuranylcarbonyl), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, and benzo[b]thiophenyl-2-carbonyl).

The term "aryl" refers to an aromatic monocyclic, bicyclic, or tricyclic hydrocarbon ring system. Unless otherwise specified, the "aryl" group contains from 6 to 14 carbon atoms. Examples of aryl moieties include, but are not limited to, phenyl, naphthyl, anthracenyl, and pyrenyl.

The terms "cycloalkyl" and "cycloalkylene" refer to a saturated monocyclic or bicyclic hydrocarbon moiety such as cyclopropyl, cyclobutyl, cyclopentyl, and cyclohexyl. Unless otherwise specified, the "cycloalkyl" or "cycloalkylene" group contains from 3 to 10 carbon atoms.

The term "cycloalkylalkyl" refers to a cycloalkyl group bound to an alkyl group, where the alkyl group is bound to the rest of the molecule.

The term "heterocycle" (or "heterocyclyl") refers to a non-aromatic 5- to 8-membered monocyclic, or 7- to 12-membered bicyclic, or 11- to 14-membered tricyclic ring system which is either saturated or unsaturated, and which contains from 1 to 3 heteroatoms if monocyclic, 1-6 heteroatoms if bicyclic, or 1-9 heteroatoms if tricyclic, independently selected from nitrogen, oxygen and sulfur, and wherein the nitrogen and sulfur heteroatoms may be optionally oxidized, and the nitrogen heteroatom may be optionally quaternized. For instance, the heterocycle may be a cycloalkoxy group. The heterocycle may be attached to the rest of the molecule via any heteroatom or carbon atom in the heterocycle. Heterocycles include, but are not limited to, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heteroaryl" refers to an aromatic 5-8 membered monocyclic, 7-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively). The heteroaryl groups herein described may also contain fused rings that share a common carbon-carbon bond.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, dialkylamino, and cyclic amino compounds.

The term "halogen" or "halo" refers to fluoro, chloro, bromo and iodo.

The following abbreviations may be used in this application:
DSPC: distearoylphosphatidylcholine; DPPC: 1,2-Dipalmitoyl-sn-glycero-3-phosphocholine; POPC: 1-palmitoyl-2-oleoyl-sn-phosphatidylcholine; DOPE: 1,2-dileoyl-sn-3-phosphoethanolamine; PEG-DMG generally refers to 1,2-dimyristoyl-sn-glycerol-methoxy polyethylene glycol (e.g., PEG 2000); TBDPSCl: tert-Butylchlorodiphenylsilane; DMAP: dimethylaminopyridine; NMO: N-methylmorpholin-N-oxide; LiHDMS: lithium bis(trimethylsilyl)amide; HMPA: hexamethylphosphoramide; EDC: 1-ethyl-3-(3-dimethylaminopropyl)carbodiimide; DIPEA: diisopropylethylamine; DCM: dichloromethane; TEA: triethylamine; TBAF: tetrabutylammonium fluoride Methods to prepare various organic groups and protective groups are known in the art and their use and modification is generally within the ability of one of skill in the art (see, for example, Green, T. W. et. al., *Protective Groups in Organic Synthesis* (1999); Stanley R. Sandler and Wolf Karo, *Organic Functional Group Preparations* (1989); Greg T. Hermanson, Bioconjugate Techniques (1996); and Leroy G. Wade, *Compendium Of Organic Synthetic Methods* (1980)). Briefly, protecting groups are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds may be prepared by at least one of the techniques described herein or known organic synthesis techniques.

EXAMPLES

Example 1

Synthesis of Intermediate 1

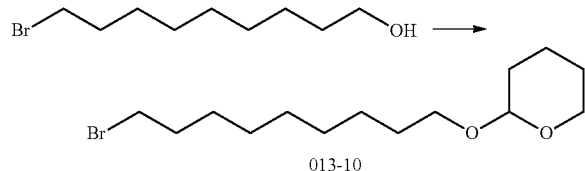

To a solution of 9-bromononan-1-ol (5 g, 22.4 mmol) and 2,3-dihydro-2H-pyran (1.93 g, 23 mmol) in DCM (125 mL) was added PPTS (628 mg, 2.5 mmol, pyridinium p-toluenesulfonate). The mixture was stirred for three hours at RT and was then concentrated. The residue was taken up in hexanes and filtered. The filtrate was concentrated and purified by dry column chromatography (0 to 5% ethyl acetate in hexanes). This gave a colorless oil (6.75 g, 22.0 mmol, 98%).

Synthesis of Intermediate 2

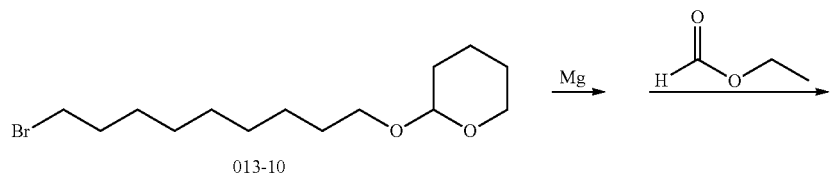

To magnesium (588 mg, 24.2 mmol)) and a small crystal of iodine in 10 mL of anhydrous ether was added 5 mL of a solution of Intermediate 1 (6.75 g, 22 mmol) in 40 mL of anhy diethyl ether. The mixture was refluxed for 20 min and then the rest of Intermediate 1 solution was added. The mixture was continued to reflux overnight. The mixture was cooled to RT, followed by addition of ethyl formate (26 mmol, 2.1 mL, 1.93 g) dropwise in 10 min. More ether (30 mL) was added. The resulting mixture was stirred overnight at ambient temperature. The mixture was diluted with ether and saturated NH4Cl solution was added. The aqueous phase was extracted with ether. The combined organic extracts were washed with brine, dried with sodium sulfate. Concentration gave a light yellow oil that was quickly cleaned by column chromatography on silica gel (230-400 mesh) eluted with 30% ethyl acetate in hexanes. This gave the desired product (013-11B) as slightly yellow oil (6.95 g).

The formate (013-11B, 6.96 g) and KOH (13 mmol, 808 mg in 13 mL of water) were stirred in EtOH (75 mL) at room temperature under nitrogen for 2 h. Upon completion of the reaction, 15 drops of conc HCl was added to the reaction mixture and the solvent was evaporated. The residue was washed with hexanes (3×30 mL) and filtered. The filtrate was concentrated to give a slightly yellow oil (5.45 g). The oil was purified by column chromatography (0-15% ethyl acetate in hexanes). This gave the desired product as a white solid (013-11C—Intermediate 2, 2.86 g). $^1$H NMR (400 MHz, CDCl3) δ: 4.58 (m, 2H), 3.91-3.85 (m, 2H), 3.75 (t, J=6.9 Hz, 1H), 3.72 (t, J=6.9 Hz, 1H), 3.59 (m, 1H), 3.53-3.48 (m, 2H), 3.40 (t, J=6.6 Hz, 1H), 3.37 (t, J=6.6 Hz, 1H), 1.88-1.79 (m, 2H), 1.76-1.69 (m, 2H), 1.63-1.50 (m, 8H estimated, due to overlap with water peak), 1.50-1.26 (m, 32H).

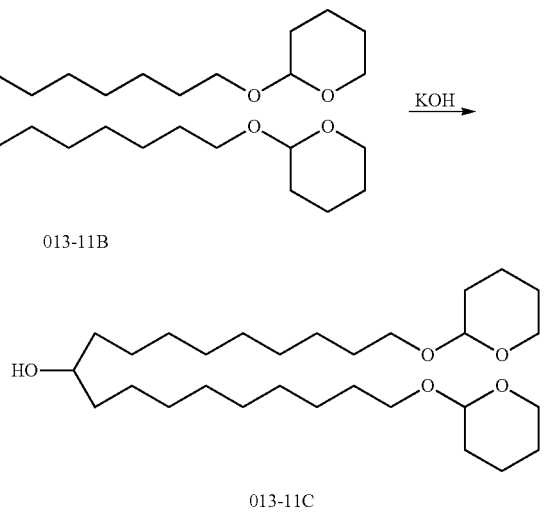

Synthesis of Intermediate 3

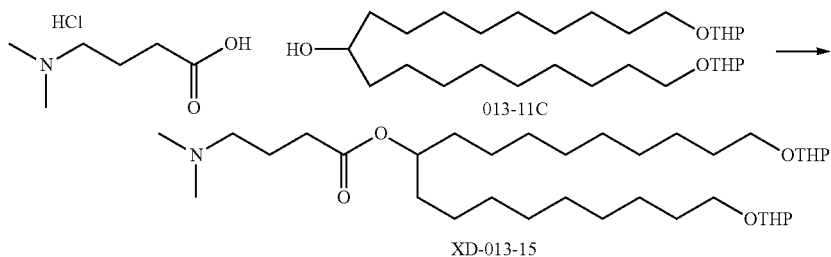

Under an argon atmosphere, to a round-bottom flask charged with 013-11C—Intermediate 2 (2.40 g, 4.96 mmol), 4-dimethylaminobutyric acid hydrochloride (1.67 g, 10 mmol), 4-(dimethylamino)pyridine (300 mg) and triethylamine (1.67 mL, 12 mmol) in dichloromethane (80 mL) was added dicyclohexylcarbodiimide (DCC, 2.27 g, 11 mmol). Upon being stirred for 16-hour period at ambient temperature, the white precipitate is discarded by filtration. The filtrate was concentrated to dryness. The resulting residue was taken up in water and ethyl acetate/hexanes (ca, 1:3). The two layers were separated. The aqueous phase was adjusted to pH 8 with HCl and sodium bicarbonate. The aqueous was then extracted with hexanes (3×50 mL). The combined extracts were dried over sodium sulfate and concentrated. The residue was purified by column chromatography on silica gel (0 to 6% methanol in dichloromethane). This gave the desired product as a colorless oil (2.70 g, 4.51 mmol, 92%). $^1$H NMR (400 MHz, CDCl3) δ: 4.87 (quintet-like, J=6.2 Hz, 1H), 4.58 (m, 2H), 3.91-3.85 (m, 2H), 3.75 (t, J=6.9 Hz, 1H), 3.72 (t, J=6.9 Hz, 1H), 3.54-3.48 (m, 2H), 3.40 (t, J=6.6 Hz, 1H), 3.37 (t, J=6.6 Hz, 1H), 2.33 (t, J=7.5 Hz, 2H), 2.29 (t, J=7.5 Hz, 2H), 2.23 (s, 6H), 1.89-1.69 (m, 6H), 1.63-1.49 (m, 16H), 1.40-1.26 (m, 24H).

Synthesis of Intermediate 4

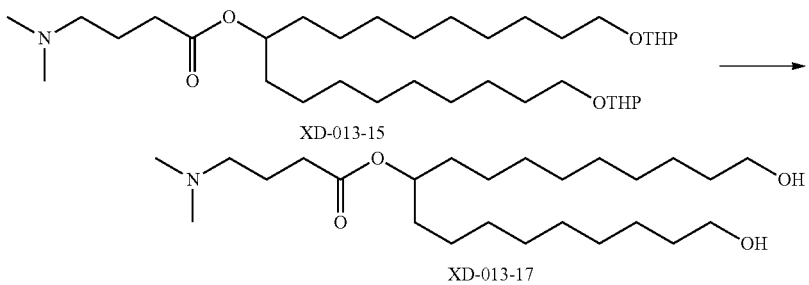

To a flask containing XD-013-15—Intermediate 3 (2.70 g, 4.51 mmol, in EtOH (80 mL) was added p-toluenesulfonic acid monohydrate (4.5 mmol, 855 mg), at room temperature and stirred for 24 h. After the reaction was quenched with dilute sodium bicarbonate solution (200 mL), the aqueous layer was extracted with diethyl ether (3×100 mL). The combined organic layers were washed with half saturated brine (100 mL), dried over sodium sulfate, filtered and concentrated. The residue was purified by column chromatography on silica gel (0 to 14% methanol in dichloromethane). This gave the desired product as a slightly yellow solid (1.604 g, 3.73 mmo, 83%).

Synthesis of Compound 1

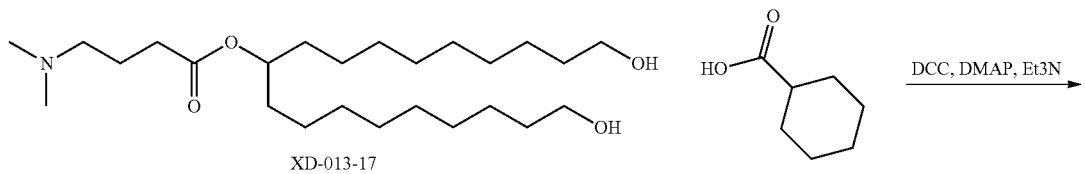

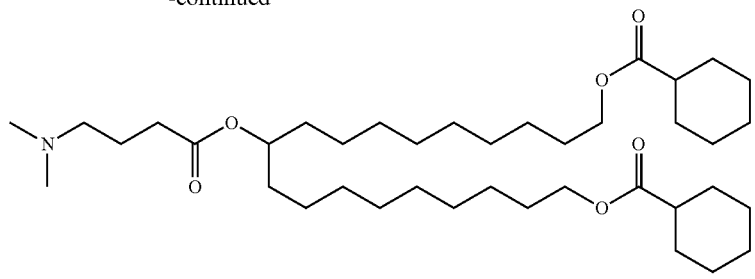

XD-013-18

Dicyclohexylcarbodiimide (DCC, 851 mg, 4.12 mmol, 5.5 eq) was added to a solution of cyclohexanecarboxylic acid (479 mg, 3.74 mmol, 5 eq.), XD-013-17—Intermediate 4 (321 mg, 0.75 mmol) and 4-dimethylaminopyridine (DMAP, 60 mg) and triethylamine (4.12 mmol, 0.57 mL) in dichloromethane (20 mL). After being stirred for 16 h, the mixture was concentrated and the residue was taken in hexanes and water. The white precipitate is filtered off. The colorless filtrate was washed twice with dilute sodium carbonate. The aqueous phase was extracted with hexanes once (70 mL). The combined organic phases were washed with brine (100 mL), dried over sodium sulfate, filtered and concentrated to dryness. The residue was purified by column chromatography on silica gel (0 to 5% methanol in DCM). This gave the desired product as a slightly yellow oil (264 mg, 0.41 mmol, 54%). $^1$H NMR (400 MHz, CDCl3) δ: 4.87 (quintet-like, J=6.2 Hz, 1H), 4.05 (t, J=6.7 Hz, 4H), 2.35-2.25 (m, 6H), 2.23 (s, 6H), 1.93-1.87 (m, 4H), 1.84-1.73 (m, 6H), 1.68-1.57 (m, 6H), 1.56-1.39 (m, 8H), 1.36-1.21 (m, 30H).

Synthesis of Compound 2

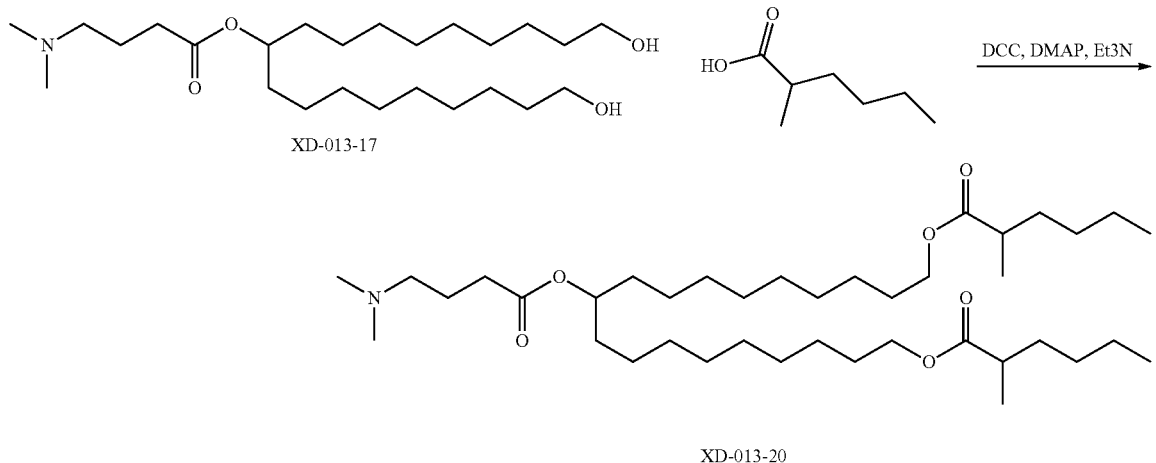

XD-013-17

XD-013-20

Compound 2 (XD-013-20) was prepared in a similar manner to that described for XD-013-18—Compound 1 (slightly yellow oil, 327 mg, 0.50 mmol, 66.7%). $^1$H NMR (400 MHz, CDCl3) δ: 4.87 (quintet-like, J=6.2 Hz, 1H), 4.06 (t, J=6.6 Hz, 4H), 2.42 (sixtet-like, J=7 Hz, 2H), 2.33 (t, J=7.6 Hz, 2H), 2.29 (t-like, J=7.4 Hz, 2H), 2.23 (s, 6H), 1.80 (quintet, J=7.4 Hz, 2H), 1.70-1.48 (m, 8H, estimated; overlapped with water peak), 1.48-1.20 (m, 36H), 1.14 (d, J=7 Hz, 6H), 0.90 (t, J=6.9 Hz, 6H).

Synthesis of Compound 3

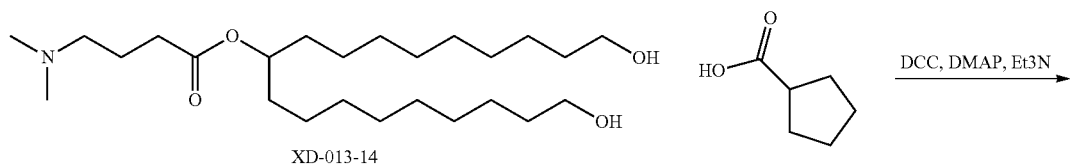

XD-013-14

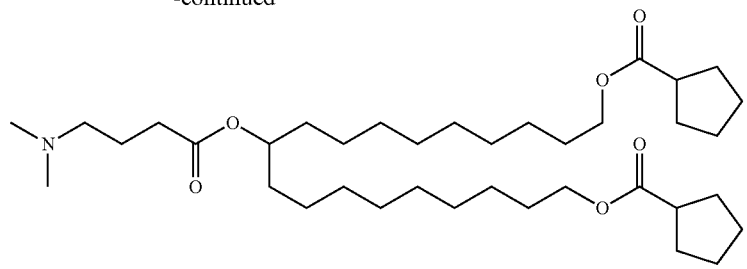

XD-013-16

Compound 3 (XD-013-16) was prepared in a similar manner to that described for Compound 1 (XD-013-18) (a slightly yellow oil, 189 mg, 0.30 mmol, 78%). $^1$H NMR (400 MHz, CDCl3) δ: 4.87 (quintet-like, J=6.2 Hz, 1H), 4.06 (t, J=6.6 Hz, 4H), 2.72 (quintet, J=8 Hz, 2H), 2.33 (t, J=7.6 Hz, 2H), 2.29 (t-like, J=7.6 Hz, 2H), 2.23 (s, 6H), 1.93-1.48 (m, 26H), 1.36-1.25 (m, 24H).

Synthesis of Compound 4

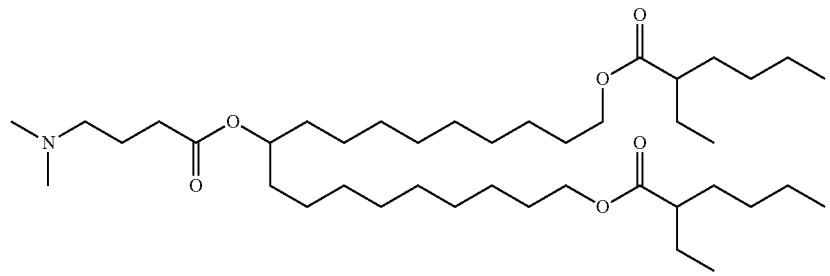

Compound 4 (XD-013-41) was prepared in a similar manner to that described for Compound 1 (XD-013-18) (a slightly yellow oil, 201 mg, 0.29 mmol, 75%). $^1$H NMR (400 MHz, CDCl3) δ: 4.87 (quintet-like, J=6.2 Hz, 1H), 4.08 (t, J=6.6 Hz, 4H), 2.35-2.24 (m, 6H), 2.22 (s, 6H), 1.79 (quintet-like, J=7.4 Hz, 2H), 1.66-1.41 (m, 16H), 1.37-1.21 (m, 32H), 0.89 (2 triplets, 12H).

Synthesis of Compound 5

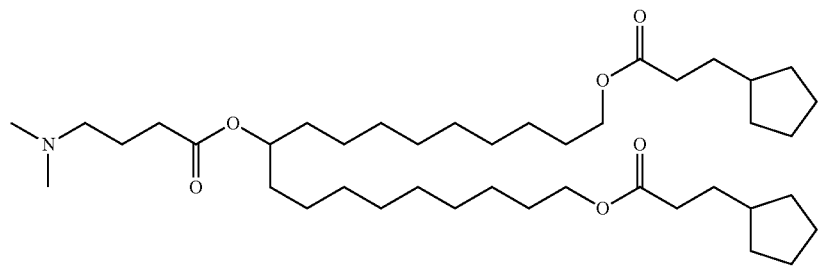 [SMILES: CN(C)CCCC(=O)OC(CCCCCCCCCOC(=O)CCC1CCCC1)CCCCCCCCCOC(=O)CCC1CCCC1]

Compound 5 (XD-013-42) was prepared in a similar manner to that described for Compound 1 (XD-013-18) (a slightly yellow oil, 233 mg, 0.34 mmol, 88%). $^1$H NMR (400 MHz, CDCl3) δ: 4.87 (quintet-like, J=6.2 Hz, 1H), 4.06 (t, J=6.8 Hz, 4H), 2.35-2.26 (m, 8H), 2.27 (s, 6H), 1.83-1.72 (m, 8H), 1.67-1.48 (m, 20H), 1.37-1.24 (m, 24H), 1.15-1.06 (m, 4H).

Synthesis of Compound 6

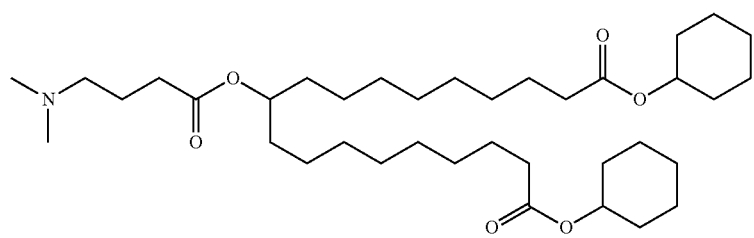 [SMILES: CN(C)CCCC(=O)OC(CCCCCCCCC(=O)OC1CCCCC1)CCCCCCCCC(=O)OC1CCCCC1]

Compound 6 is prepared by the methods described herein.

Synthesis of Intermediate 5

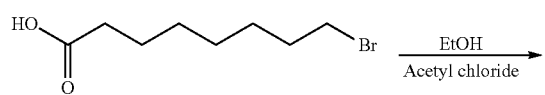

Synthesis of Intermediate 6

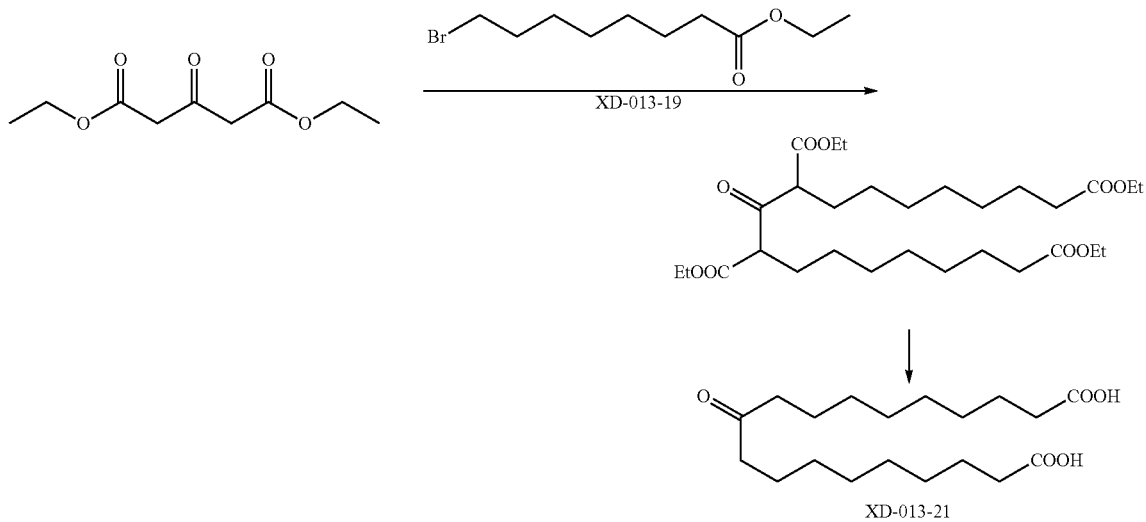

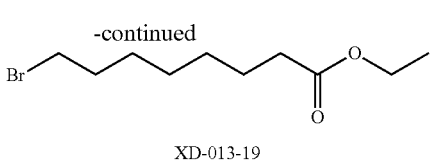

To an ice-salt-cooled solution of 10 g (45 mmol) of 8-bromooctanoic acid in 180 mL of ethanol is added slowly 9 mL of acetyl chloride (127 mmol) under Ar. The resulting mixture was stirred for 20 min before removing the cooling bath. The solution is allowed to stand overnight at room temperature (20 h). Solvent was removed under reduced pressure. The residual oil was dissolved in hexanes (200 mL) and washed with dilute sodium bicarbonate twice (2×70 mL). The aqueous phase was extracted with hexanes (100 mL). The combined organic solution was washed with brine (2×70 mL), dried over sodium sulfate, filtered and concentrated to give a colorless oil (10.49 g, 41.8 mmol, 93%).

To a solution of sodium ethoxide (1.422 g, 20.9 mmol) in EtOH (10 mL) was added diethyl acetonedicarboxylate (4.23 g, 3.800 mL, 20.9 mmole). The stirred solution was heated to the reflux temperature, and then ethyl 8-bromooctanoate (XD-013-19, 5.24 g, 20.9 mmol) was added slowly. Stirring and heating were continued for two hours. After another solution of sodium ethoxide (20.9 mmole in 10 mL of EtOH) was added at reflux temperature, another 20.9 mmole of ethyl 8-bromooctanoate was added dropwise. The mixture was heated and stirred for 16 hours after addition was complete. Most of the ethanol was removed under reduced pressure. To the residue were added water (70 mL) and ether (250 mL). Saturated NH4Cl solution was added to adjust to pH 7. The two layers were separated. The ethereal solution was washed again with dilute NH4Cl, brine. Concentration led to a brownish oil (11.44 g). The oil was hydrolyzed by boiling for 18 hours with a mixture of concentrated hydrochloric acid (21 mL) and glacial acetic acid (10.5 mL). The hydrolysis mixture was evaporated to dryness under reduced pressure, and the solid residue was washed with water and was crystallized from acetone. The product was dried well and was obtained as a pale solid (1.74 g).

Synthesis of Intermediate 7

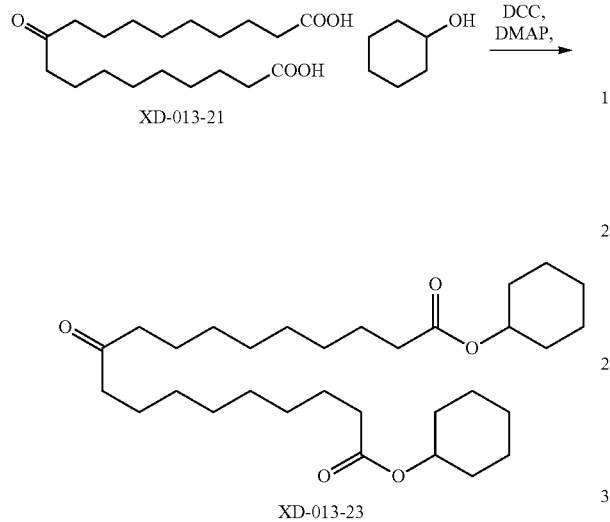

DCC (957 mg, 4.64 mmol) was added to a solution of cyclohexanol (696 mg, 6.96 mmol), Intermediate 6 (XD-013-21) (400 mg, 1.16 mmol) and 4-dimethylaminopyridine (DMAP, 366 mg, 3 mmol) in dichloromethane (20 mL). After being stirred for 16 h, the reaction mixture was filtered. The filtrate was concentrated. The residue was purified by column chromatography on silica gel (0 to 5% ethyl acetate in hexanes). This gave the desired product as a white solid (0.44 g, 0.87 mmol, 75%).

Synthesis of Intermediate 8

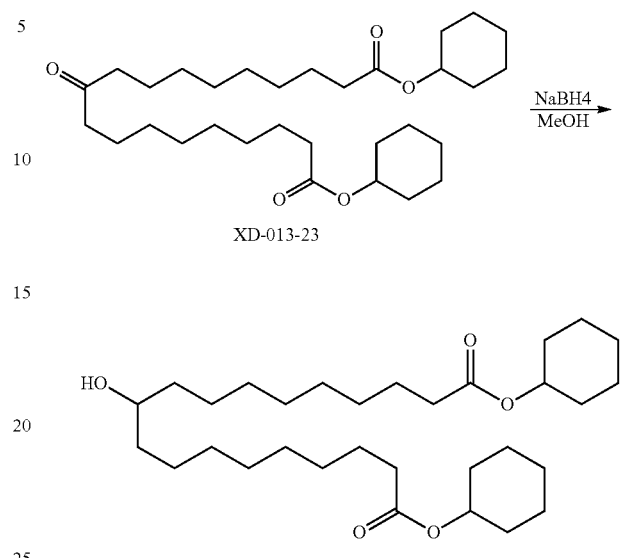

A solution of Intermediate 8 (XD-013-23) in 10% methanol in dichloromethane (25 mL) was cooled to 5° C., followed by addition of NaBH4 (1.74 mmol, 66 mg). After being stirred for 10 min, the cooling bath was removed and the reaction was stirred at RT for 30 min. Diluted with sodium bicarbonate solution (ca 30 mL) and dichloromethane (60 mL). The organic layer was separated and the aqueous layer was extracted with dichloromethane (3×30 mL). The combined organic layers were washed with brine, dried over sodium sulfate and concentrated. The residue was loaded on a column (40 mL of silica gel). The column was eluted with ethyl acetate in hexanes (4 to 15%). The desired product was obtained as a white solid (0.40 g, 0.78 mmol, 90%).

Synthesis of Compound 6

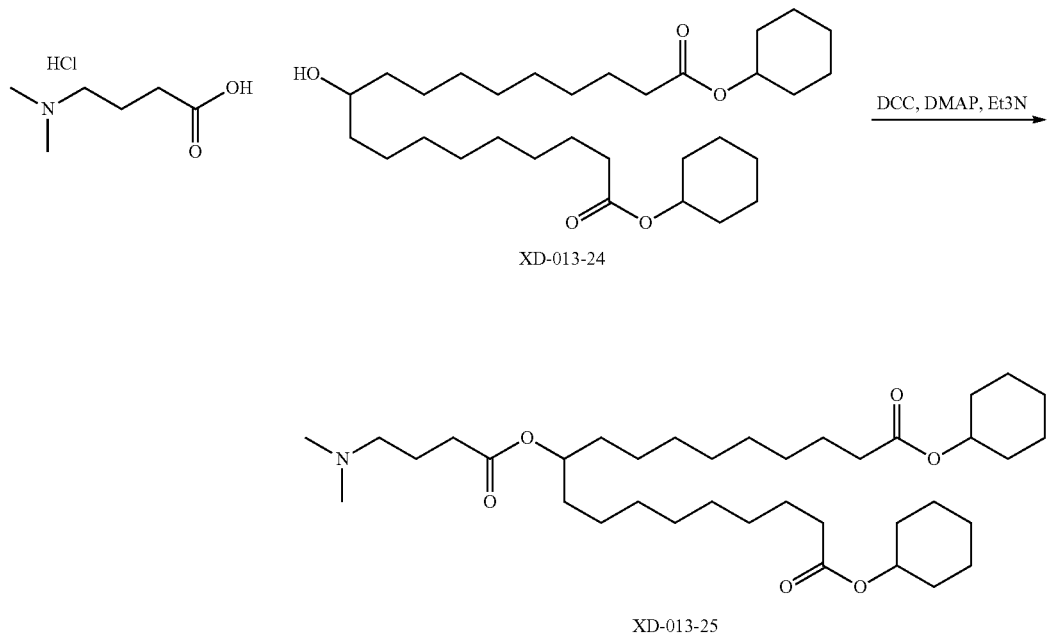

Under an argon atmosphere, to a round-bottom flask charged with XD-013-24—Intermediate 8 (400 mg, 0.78 mmol), 4-dimethylaminobutyric acid hydrochloride (261 mg, 1.56 mmol), 4-(dimethylamino)pyridine (60 mg) and triethylamine (261 uL) in dichloromethane (20 mL) was added dicyclohexylcarbodiimide (354 mg, 1.72 mmol). After the mixture is stirred for 16 hr at ambient temperature, the white precipitate is discarded by filtration. The filtrate was concentrated to dryness. The resulting residue was purified by column chromatography on silica gel (230-400 mesh, 40 mL) eluted with methanol in dichloromethane (0 to 5%). This gave the desired product as a colorless oil (330 mg, 0.53 mmol, 68%). $^1$H NMR (400 MHz, CDCl3) δ: 4.87 (quintet-like, J=6.2 Hz, 1H), 4.76 (m, 2H), 2.35-2.25 (m, 8H), 2.22 (s, 6H), 1.87-1.56 (m, 14H), 1.55-1.22 (m, 36H).

Synthesis of Compound 7

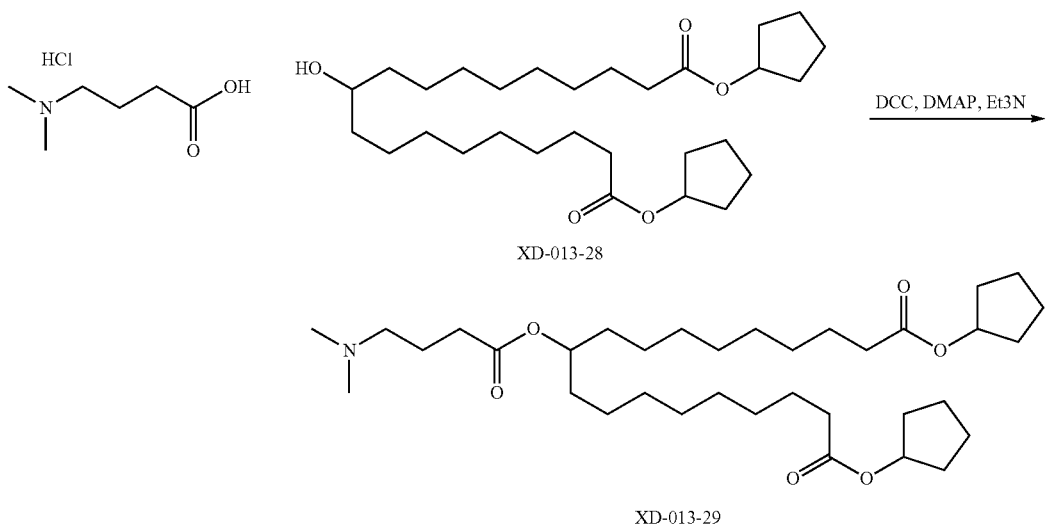

Compound 7 (XD-013-29) was prepared in a similar manner to that described for Compound 6 (XD-013-25) (a colorless oil, 421 mg, 0.71 mmol, 61% overall yield in 3 steps from XD-013-21—Intermediate 6). $^1$H NMR (400 MHz, CDCl3) δ: 5.19-5.14 (m, 2H), 4.86 (quintet-like, J=6.2 Hz, 1H), 2.38-2.23 (m, 14H), 1.91-1.79 (m, 6H), 177-1.55 (m, 16H), 1.55-1.46 (m, 4H), 1.35-1.22 (m, 20H).

Synthesis of Compound 8

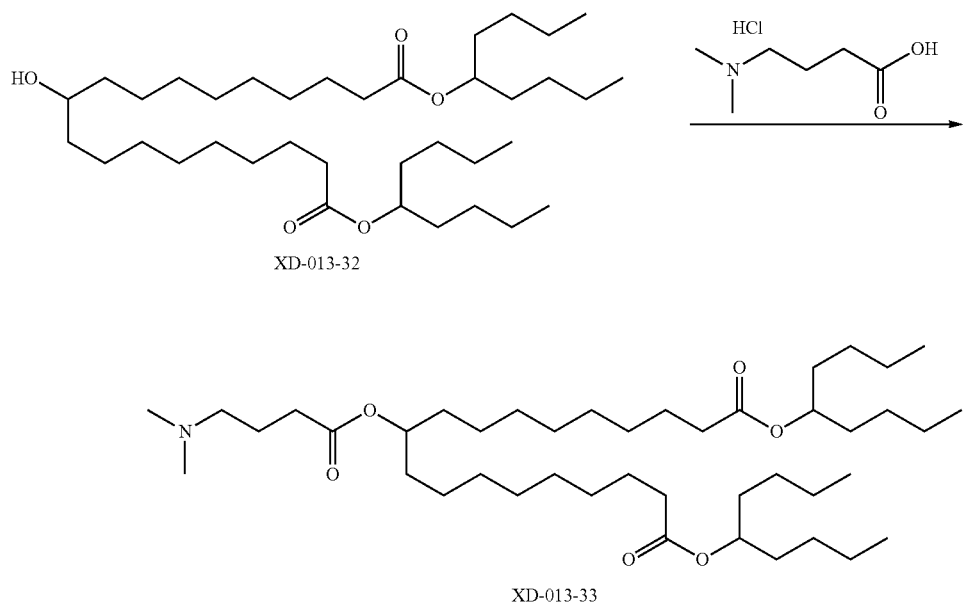

Compound 8 (XD-013-33) was prepared in a similar manner to that described for Compound 6 (XD-013-25) (a colorless oil, 295 mg, 0.41 mmol, 35% overall yield in 3 steps from XD-013-21—Intermediate 6). $^1$H NMR (400 MHz, CDCl3) δ: 4.91-4.83 (m, 3H), 2.35-2.26 (m, 8H), 2.22 (s, 6H), 1.79 (quintet-like, J=7.4 Hz, 2H), 1.66-1.59 (m, 4H, overlap with water peak), 1.56-1.48 (m, 12H), 1.35-1.22 (m, 36H), 0.89 (t-like, J=6.8 Hz, 12H).

Synthesis of Compound 9

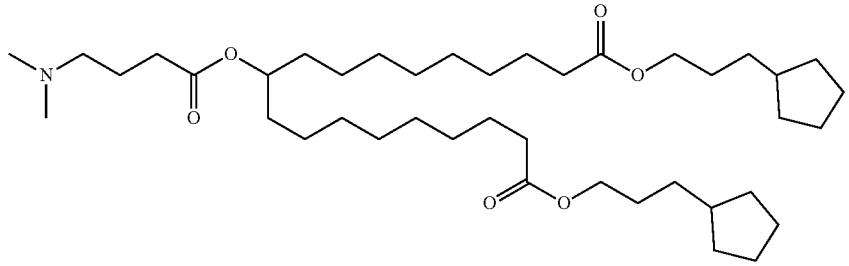 [SMILES: CN(C)CCCC(=O)OC(CCCCCCCCC(=O)OCCCC1CCCC1)CCCCCCCCC(=O)OCCCC1CCCC1]

Compound 9 (XD-013-45) was prepared in a similar manner to that described for Compound 6 (XD-013-25) (a slightly yellow oil, 309 mg, 0.45 mmol, 45% overall yield in 3 steps from XD-013-21—Intermediate 6). $^1$H NMR (400 MHz, CDCl3) δ: 4.87 (quintet-like, J=6.2 Hz, 1H), 4.06 (t, J=6.8 Hz, 4H), 2.35-2.26 (m, 8H), 2.23 (s, 6H), 1.83-1.71 (m, 8H), 1.68-1.57 (m, 14H, overlap with water peak), 1.55-1.46 (m, 8H), 1.39-(m, 22H), 1.13-1.03 (4H).

Synthesis of Compound 10

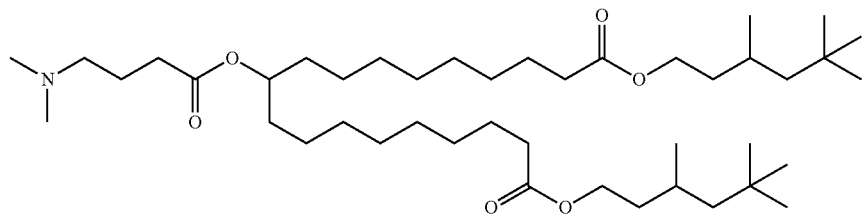 [SMILES: CC(CCOC(=O)CCCCCCCCC(CCCCCCCCC(=O)OCCC(C)CC(C)(C)C)OC(=O)CCCN(C)C)CC(C)(C)C]

Compound 10 (XD-013-58) was prepared in a similar manner to that described for Compound 6 (XD-013-25) (a slightly yellow oil, 205 mg, 0.29 mmol, 31% overall yield in 3 steps from XD-013-21—Intermediate 6). $^1$H NMR (400 MHz, CDCl3) δ: 4.86 (m, 1H), 4.09 (t, J=6.6 Hz, 4H), 2.35-2.27 (m, 8H), 2.22 (s, 6H), 1.79 (quintet-like, J=7.4 Hz, 2H), 1.68-1.56 (m, 8H), 1.50-1.41 (m, 4H), 1.38-1.22 (m, 24H), 1.11-1.06 (m, 2H), 0.95 (d, J=6.4 Hz, 6H), 0.90 (s, 18H).

Synthesis of Compound 11

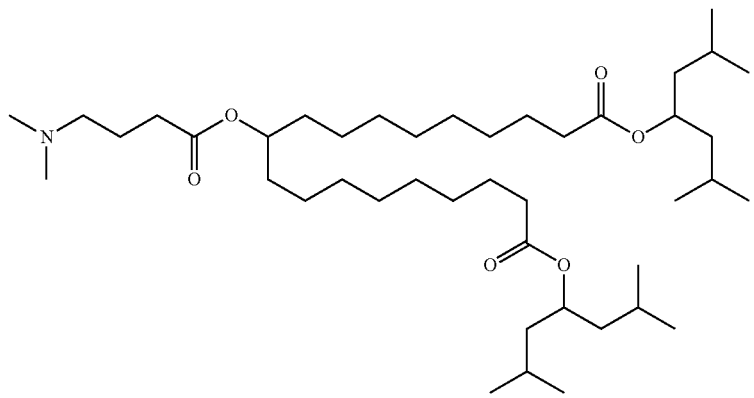 [SMILES: CC(C)CC(CC(C)C)OC(=O)CCCCCCCCC(CCCCCCCCC(=O)OC(CC(C)C)CC(C)C)OC(=O)CCCN(C)C]

Compound 11 (XD-013-60) was prepared in a similar manner to that described for Compound 6 (XD-013-25) (a slightly yellow, 175 mg, 0.25 mmol, 27% overall yield in 3 steps from XD-013-21—Intermediate 6). $^1$H NMR (400 MHz, CDCl3) δ: 5.11-5.03 (m, 2H), 4.87 (m, 1H), 2.35-2.25 (m, 8H), 2.23 (s, 6H), 1.79 (quintet-like, J=7.4 Hz, 2H), 1.68-1.56 (m, 8H), 1.55-1.45 (m, 8H), 1.34-1.22 (m, 24H), 0.91 (d, 24H).

Synthesis of Compound 12

Synthesis of 1,13-bis(nonan-5-yl) 7-oxotridecanedioate: A solution of 7-oxo-tridecane-1,13-dioic acid (1.01 g), 4-dimethylaminopyridine (1.43 g), N-(3-dimethylaminopropyl)-N-ethylcarbodiimide hydrochloride (2.1 g) and nonan-5-ol (1.96 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 2.85 g of product.

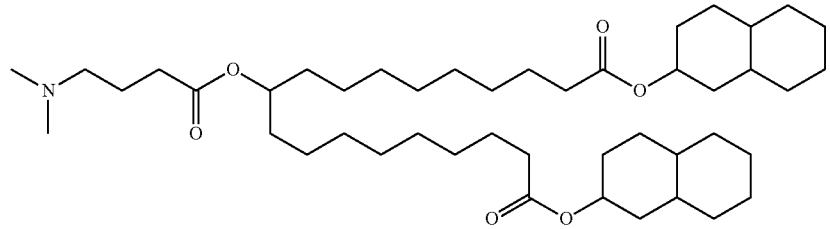 [SMILES: CN(C)CCCC(=O)OC(CCCCCCCCC(=O)OC1CCC2CCCCC2C1)CCCCCCCCC(=O)OC1CCC2CCCCC2C1]
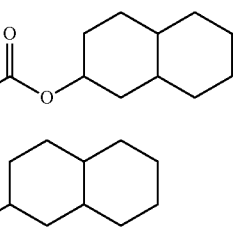

Compound 12 (XD-013-63) was prepared in a similar manner to that described for Compound 6 (XD-013-25). Compound 12 was produced as a slightly yellow oil (197 mg, mmol, 29% overall yield in 3 steps from XD-013-21—Intermediate 6). $^1$H NMR (400 MHz, CDCl3) δ: 5.00-4.92 (m, 1H), 4.87 (m, 1H), 4.79-4.68 (m, 1H), 2.35-2.23 (m, 8H), 2.23 (s, 6H), 1.79 (quintet-like, J=7.4 Hz, 2H).

Synthesis of Intermediate 11 (ethyl 5-iodovalerate)

A solution of ethyl 5-bromovalerate (25 g) and sodium iodide (90 g) in acetone (300 mL) was stirred at room temperature overnight. The reaction mixture was diluted with water (200 mL) and extracted with diethyl ether (200 mL). The organic fraction was washed with water, dried over anhydrous magnesium sulfate, filtered and the solvent removed, yielding ethyl 5-iodovalerate (32 g).

Synthesis of Intermediate 12
(7-oxo-tridecane-1,13-dioic acid)

Sodium ethoxide (3.6 g) was dissolved in absolute ethanol (30 mL). Diethylacetone dicarboxylate (12 g) was added and the solution heated to reflux. Ethyl 5-iodovalerate (16 g) was slowly added and the solution refluxed for an hour. A solution of sodium ethoxide (3.6 g) in ethanol (30 mL) was added, followed by ethyl 5-iodovalerate (16 g). The solution was refluxed overnight. The reaction mixture was cooled, diluted with water (200 mL) and extracted with diethyl ether (200 mL). The organic fraction was washed with water and the solvent removed. The residue was treated with acetic acid (30 mL) and concentrated hydrochloric acid (60 mL), and then refluxed overnight. The solution was cooled, diluted with water and extracted with dichloromethane. The solvent was removed and the residue recrystallized from acetone, yielding 7-oxo-tridecane-1,13-dioic acid as a white powder (5.9 g)

Synthesis of Compound 13

Synthesis of 1,13-bis(nonan-5-yl) 7-hydroxytridecanedioate: A solution of 1,13-bis(nonan-5-yl) 7-oxotridecanedioate (2.85 g) in dichloromethane (20 mL) and methanol (1 mL) was treated with sodium borohydride (0.60 g). When the reaction was complete (as judged by TLC) the solution was diluted with water, acidified and extracted with dichloromethane. The organic fraction was dried over anhydrous magnesium sulfate, filtered and the solvent removed. The residue was passed down a silica gel (20 g) column using 0-3% methanol/dichloromethane as the eluent, yielding 1.26 g of product.

Synthesis of 1,13-bis(nonan-5-yl) 7-{[4-(dimethylamino) butanoyl]oxy}tridecanedioate: A solution of 1,13-bis(nonan-5-yl) 7-hydroxytridecanedioate (1.26 g), 4-dimethylaminopyridine (0.98 g), N-(3-dimethylaminopropyl)-N-ethylcarbodiimide hydrochloride (0.78 g) and N,N-dimethylaminobutyric acid hydrochloride (1.22 g) in dichloromethane (20 mL) was stirred at room temperature overnight. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-3% methanol/dichloromethane as the eluent, yielding 1.04 g of product. $^1$H NMR (CDCl$_3$): δ4.87 (p; J=6.2 Hz; 3H); 2.3 (m; 8H); 2.22 (bs; 6H); 1.78 (p; J=7.2 Hz; 2H); 0.89 (t; J=6.8 Hz; 12H).

Synthesis of Compound 14

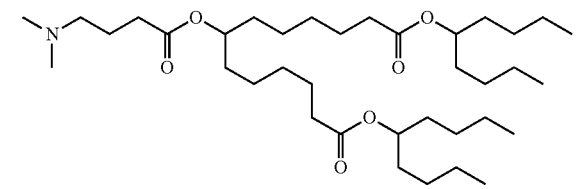 [SMILES: CCCCC(CCCC)OC(=O)CCCCCC(CCCCCC(=O)OC(CCCC)CCCC)OC(=O)CCCN(C)C]
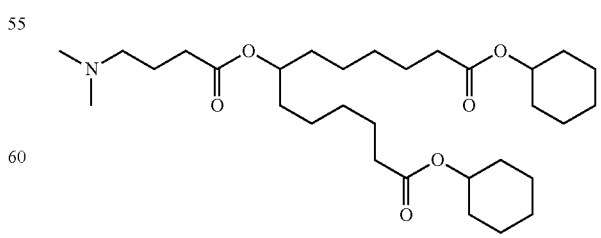

Synthesis of 1,13-dicyclohexyl 7-oxotridecanedioate: A solution of 7-oxo-tridecane-1,13-dioic acid (1.02 g), 4-dimethylaminopyridine (1.46 g), N-(3-dimethylaminopropyl)-

N-ethylcarbodiimide hydrochloride (2.2 g) and cyclohexanol (2.40 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 1.52 g of product.

Synthesis of 1,13-dicyclohexyl 7-hydroxytridecanedioate: A solution of 1,13-dicyclohexyl 7-oxotridecanedioate (1.52 g) in dichloromethane (20 mL) and methanol (1 mL) was treated with sodium borohydride (0.70 g). When the reaction was complete (as judged by TLC) the solution was diluted with water, acidified and extracted with dichloromethane. The organic fraction was dried over anhydrous magnesium sulfate, filtered and the solvent removed. The residue was passed down a silica gel (20 g) column using 0-3% methanol/dichloromethane as the eluent, yielding 1.41 g of product.

Synthesis of 1,13-dicyclohexyl 7-{[4-(dimethylamino)butanoyl]oxy}tridecanedioate: A solution of 1,13-dicyclohexyl 7-hydroxytridecanedioate (1.41 g), 4-dimethylaminopyridine (1.45 g), N-(3-dimethylaminopropyl)-N-ethylcarbodiimide hydrochloride (0.91 g) and N,N-dimethylaminobutyric acid hydrochloride (1.67 g) in dichloromethane (20 mL) was stirred at room temperature overnight. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-8% methanol/dichloromethane as the eluent, yielding 1.64 g of product.
$^1$H NMR (CDCl$_3$): δ4.86 (p; J=6.1 Hz; 1H); 4.75 (m; 2H); 2.3 (m; 8H); 2.22 (s; 6H).

passed down a silica gel (20 g) column using dichloromethane as the eluent, yielding 1.23 g of product.

Synthesis of 1,13-dicyclopentyl 7-hydroxytridecanedioate: A solution of 1,13-dicyclopentyl 7-oxotridecanedioate (1.23 g) in dichloromethane (20 mL) and methanol (1 mL) was treated with sodium borohydride (0.6 g). When the reaction was complete (as judged by TLC) the solution was diluted with water, acidified and extracted with dichloromethane. The organic fraction was dried over anhydrous magnesium sulfate, filtered and the solvent removed. The residue was passed down a silica gel (20 g) column using 0-2% methanol/dichloromethane as the eluent, yielding 1.36 g of product.

Synthesis of 1,13-dicyclopentyl 7-{[4-(dimethylamino)butanoyl]oxy}tridecanedioate: A solution of 1,13-dicyclopentyl 7-hydroxytridecanedioate (1.36 g), 4-dimethylaminopyridine (1.27 g), N-(3-dimethylaminopropyl)-N-ethylcarbodiimide hydrochloride (1.05 g) and N,N-dimethylaminobutyric acid hydrochloride (1.62 g) in dichloromethane (20 mL) was stirred at room temperature overnight. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-8% methanol/dichloromethane as the eluent, yielding 1.57 g of product.
$^1$H NMR (CDCl3): δ5.15 (m; 2H); 4.86 (p, J=6.2 Hz, 1H); 2.3 (m, 8H); 2.22 (s; 6H).

Synthesis of Compound 16

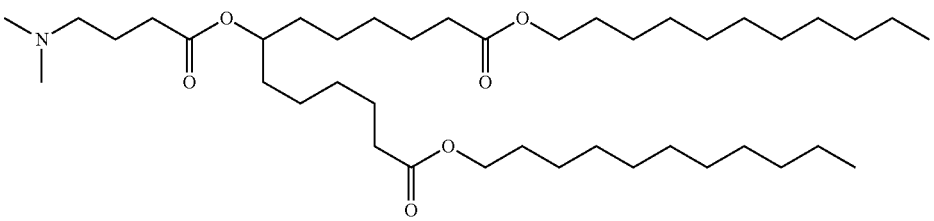

Synthesis of Compound 15

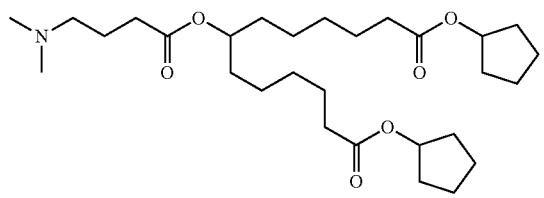 [SMILES: CN(C)CCCC(=O)OC(CCCCCC(=O)OC1CCCC1)CCCCCC(=O)OC1CCCC1]

Synthesis of 1,13-dicyclopentyl 7-oxotridecanedioate: A solution of 7-oxo-tridecane-1,13-dioic acid (0.99 g), 4-dimethylaminopyridine (1.47 g), N-(3-dimethylaminopropyl)-N-ethylcarbodiimide hydrochloride (2.32 g) and cyclopentanol (2.00 g) in dichloromethane (20 mL) was stirred at room temperature overnight. The solution was washed with diluted hydrochloric acid, dried over anhydrous magnesium sulfate, filtered and the solvent removed. The residue was Synthesis of 1,13-diundecyl 7-oxotridecanedioate: A solution of 7-oxo-tridecane-1,13-dioic acid (0.59 g), 4-dimethylaminopyridine (0.75 g), N-(3-dimethylaminopropyl)-N-ethylcarbodiimide hydrochloride (1.20 g) and undecanol (1.17 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 1.03 g of product.

Synthesis of 1,13-diundecyl 7-hydroxytridecanedioate: A solution of 1,13-diundecyl 7-oxotridecanedioate (1.03 g) in dichloromethane (20 mL) and THF (20 mL) was treated with sodium borohydride (1 g). When the reaction was complete (as judged by TLC) the solution was diluted with water, acidified and extracted with dichloromethane. The organic fraction was dried over anhydrous magnesium sulfate, filtered and the solvent removed. The residue was passed down a silica gel (20 g) column using 0-2% methanol/dichloromethane as the eluent, yielding 0.88 g of product.

Synthesis of 1,13-diundecyl 7-{[4-(dimethylamino)butanoyl]oxy}tridecanedioate: A solution of 1,13-diundecyl 7-hydroxytridecanedioate (0.88 g), 4-dimethylaminopyridine (0.68 g), N-(3-dimethylaminopropyl)-N-ethylcarbodiimide hydrochloride (0.54 g) and N,N-dimethylaminobutyric acid hydrochloride (0.82 g) in dichloromethane (20 mL) was stirred at room temperature overnight. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-5% methanol/dichloromethane as the eluent, yielding 0.77 g of product. $^1$H NMR (CDCl$_3$): δ4.87 (p; J=6.2 Hz; 1H); 4.05 (t; J=6.7 Hz; 4H); 2.3 (m; 8H); 2.22 (s; 6H); 1.79 (p; J=7.3 Hz; 1H); 0.87 (t; J=6.8 Hz; 6H)

The organic fraction was dried over anhydrous magnesium sulfate, filtered and the solvent removed. The residue was passed down a silica gel (20 g) column using 0-2% methanol/dichloromethane as the eluent, yielding 0.89 g of product.

Synthesis of 1,13-bis(2E)-3,7,11,15-tetramethylhexadec-2-en-1-yl 7-{[4-dimethylamino)-butanoyl]oxy}tridecanedioate: A solution of 1,13-bis(2E)-3,7,11,15-tetramethylhexadec-2-en-1-yl 7-hydroxytridecanedioate (0.89 g), 4-dimethylaminopyridine (0.46 g), N-(3-dimethylaminopropyl)-N-ethylcarbodiimide hydrochloride (0.37 g) and N,N-dimethylaminobutyric acid hydrochloride (0.63 g)

Synthesis of Compound 17

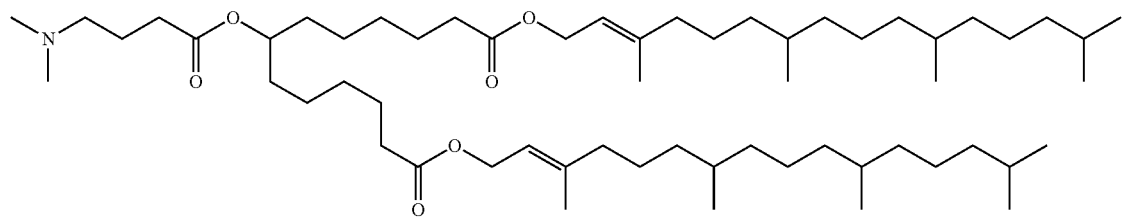 [SMILES: C/C(=C\COC(=O)CCCCCC(CCCCCC(=O)OC/C=C(\C)CCCC(C)CCCC(C)CCCC(C)C)OC(=O)CCCN(C)C)CCCC(C)CCCC(C)CCCC(C)C]

Synthesis of 1,13-bis(2E)-3,7,11,15-tetramethylhexadec-2-en-1-yl 7-oxotridecanedioate: A solution of 7-oxo-tridecane-1,13-dioic acid (0.51 g), 4-dimethylaminopyridine (0.76 g), N-(3-dimethylaminopropyl)-N-ethylcarbodiimide hydrochloride (0.60 g) and phytol (1.77 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 1.7 g of product.

Synthesis of 1,13-bis(2E)-3,7,11,15-tetramethylhexadec-2-en-1-yl 7-hydroxytridecanedioate: A solution of 1,13-bis(2E)-3,7,11,15-tetramethylhexadec-2-en-1-yl 7-oxotridecanedioate (1.7 g) in methanol (5 mL) and THF (10 mL) was in dichloromethane (20 mL) was stirred at room temperature overnight. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-4% methanol/dichloromethane as the eluent, yielding 0.62 g of product. $^1$H NMR (CDCl$_3$): δ4.87 (p, J=6.2 Hz, 3H)

Synthesis of Compound 18

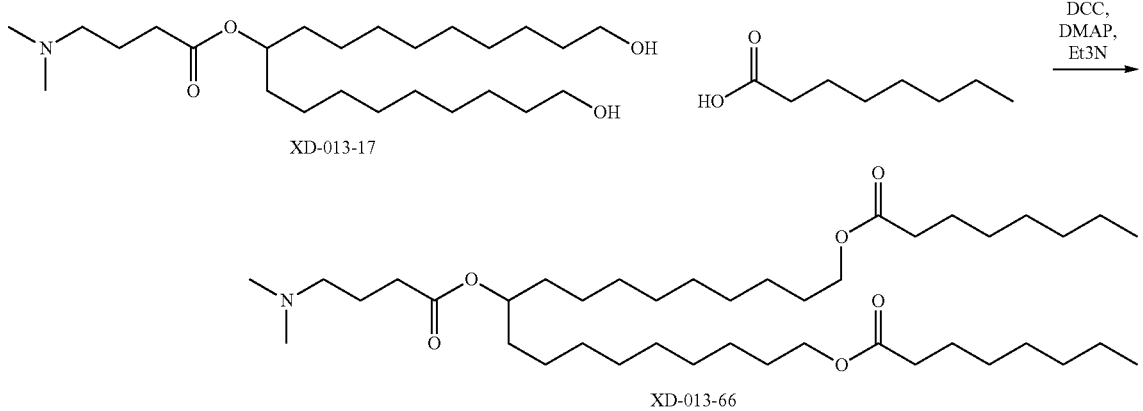

treated with sodium borohydride (1 g). When the reaction was complete (as judged by TLC) the solution was diluted with water, acidified and extracted with dichloromethane.

Compound 18 (XD-013-66) was prepared in a similar manner to that described for Compound 1 (XD-013-18) using appropriate starting materials. Compound 19 was produced as a slightly yellow oil (238 mg, 0.35 mmol, 89%). ¹H NMR (400 MHz, CDCl3) δ: 4.87 (quintet-like, J=6.2 Hz, 1H), 4.06 (t, J=6.8 Hz, 4H), 2.39-2.27 (m, 14H), 1.83 (quintet, J=7.4 Hz, 2H), 1.66-1.58 (m, 8H, estimated; overlapped with water peak), 1.54-1.48 (m, 4H), 1.37-1.22 (40H), 0.89 (t-like, J=6.8 Hz, 6H).

Synthesis of Compound 19

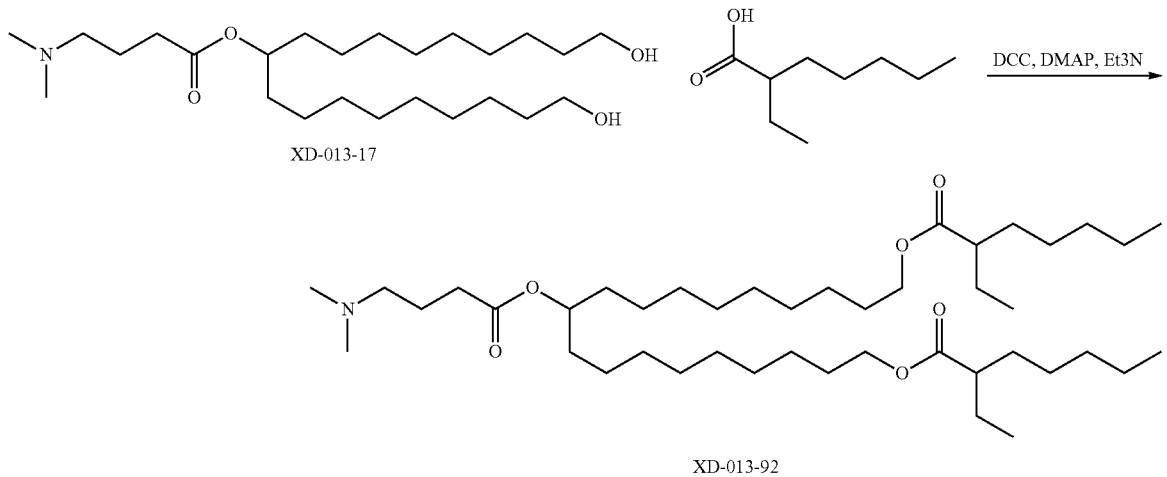

Compound 19 (XD-013-92) was prepared in a similar manner to that described for Compound 1 (XD-013-18). Compound 19 was produced as a colorless oil (208 mg, 0.29 mmol, 63%). ¹H NMR (400 MHz, CDCl3) δ: 4.87 (quintet-like, J=6.2 Hz, 1H), 4.08 (t, J=6.6 Hz, 4H), 2.38-2.32 (m, 4H), 2.27 (s, 6H), 2.30-2.22 (m, 2H), 1.82 (quintet-like, J=7.4 Hz, 2H), 1.66-1.41 (m, 16H), 1.37-1.21 (m, 36H), 0.92-0.86 (m, 12H).

Synthesis of Compound 20

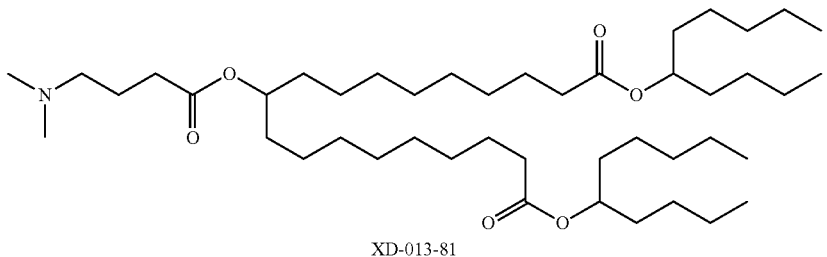 [SMILES: CCCCCC(CCCC)OC(=O)CCCCCCCCC(CCCCCCCCC(=O)OC(CCCC)CCCCC)OC(=O)CCCN(C)C]

Compound 20 (XD-013-81) was prepared in a similar manner to that described for Compound 6 (XD-013-25). Compound 20 was produced as a slightly yellow oil (381 mg, 0.52 mmol, 55% overall yield in 3 steps from XD-013-21—Intermediate 6). ¹H NMR (400 MHz, CDCl3) δ: 4.91-4.83 (m, 3H), 2.35-2.26 (m, 8H), 2.22 (s, 6H), 1.79 (quintet-like, J=7.4 Hz, 2H), 1.66-1.59 (m, 4H), 1.56-1.47 (m, 12H), 1.35-1.22 (m, 40H), 0.91-0.86 (m, 12H).

Synthesis of Compound 21

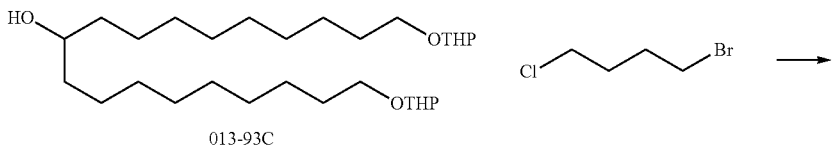

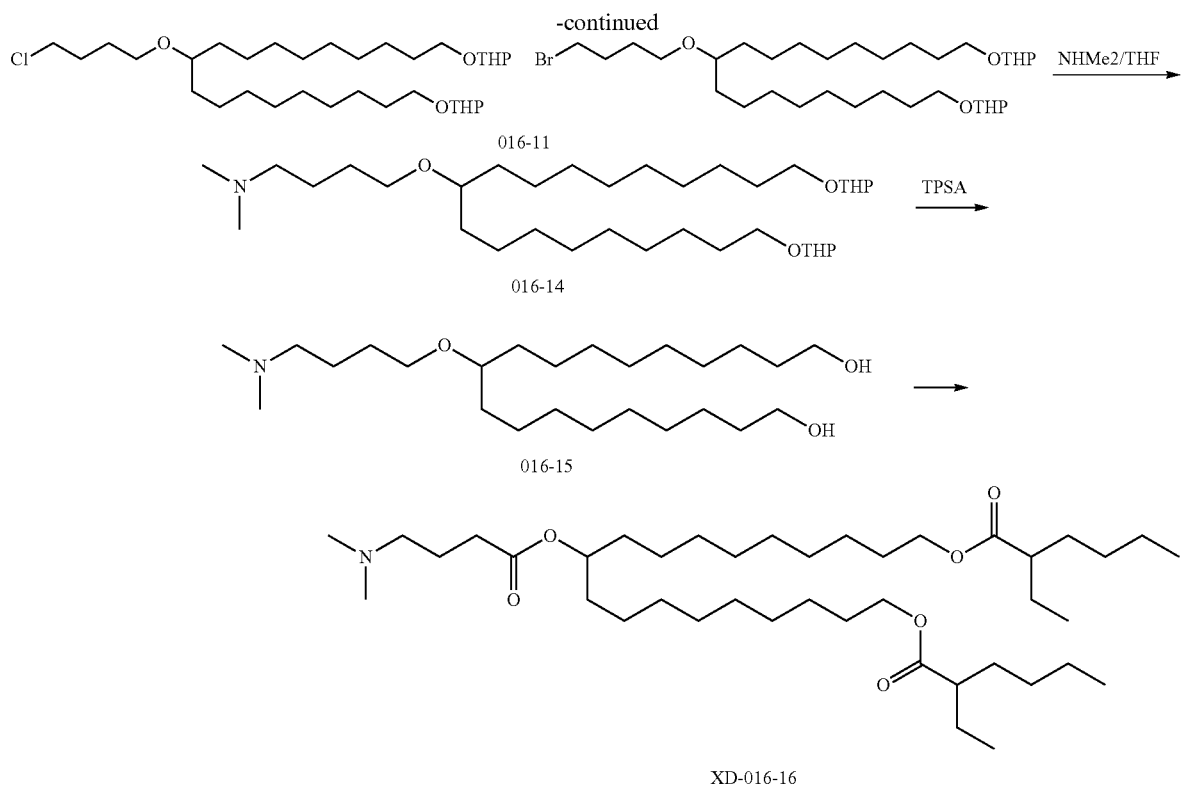

Compound 21 (XD-016-16) was prepared as follows.

Synthesis of Intermediate 13 (016-11)

To a solution of alcohol 016-93C (shown above) and 1-chloro-4-bromobutane (8 mmol, 0.92 mL) in benzene (40 mL) was added NaH (130 mg) was added. Refluxed for 16 h. More NaH (40 mg) was added and refluxed for 16 h. More NaH (90 mg) was added and refluxed for 3 days. Benzene was removed and the residue was taken in hexanes-EtOAc and washed with water, brine and dried over sodium sulfate. Concentration gave colorless oil (2 g). The residue was purified by column chromatography on silica gel (EtOAc in hexanes, 0 to 25%). This gave the desired product as colorless oil (0.28 g, 0.48 mmol, 24% based on chloride). The unreacted starting material was recovered in later fractions (0.63 g, 1.30 mmol, 63%).

Synthesis of Intermediate 14 (016-14)

The above product, Intermediate 13—016-11 (0.28 g, 0.48 mmol), was dissolved in a solution of dimethylamine in THF (2M, 15 mL). To the solution was added trace of NaI and the mixture was heated at 68-72 C for 2 days. The mixture was cooled and concentrated under reduced pressure. The residue was taken up in hexanes-EtOAc (200 mL) and washed with water, brine, dried over sodium sulfate and concentrated. The residue was combined with the product from previous batch of the same reaction. This gave 0.41 g of the desired product in total.

Synthesis of Intermediate 15 (016-15)

To a solution of the THP-protected di-OH (0.41 g, 0.7 mmol, Intermediate 14—016-14), in EtOH (20 mL) was added p-toluenesulfonic acid hydrate (0.7 mmol, 133 mg) at room temperature and was heated at 70 to 55 C for 1.5 h. Concentrated and the residue was taken up in saturated sodium bicarbonate (50 mL) and water (50 mL), the mixture was extracted with diethyl ether (2×75 mL), and the combined organic layers were washed with brine (50 mL) and dried over sodium sulfate. Concentrated and the residue was washed with hexanes (2×1 ml). This gave the desired product as a brownish solid (0.24 g).

Synthesis of Compound 21 (016-16)

Under an argon atmosphere, to a round-bottom flask charged with the alcohol, 016-15 (0.24 g, 0.58 mmol), 2-ethylhexanoic acid (500 mg, 3.46 mmol, 6 eq), 4-(dimethylamino)pyridine (200 mg) and triethylamine (0.487 mL, 3.5 mmol) in dichloromethane (15 mL) was added dicyclohexylcarbodiimide (774 mg, 3.75 mmol). After the mixture is stirred for 20 hr at ambient temperature, the mixture was concentrated. The residue was taken in hexanes/EtOAt (100 mL). The precipitate is discarded by filtration. The filtrate was washed with dilute solution of ammonium chloride and concentrated. The residue was purified by column chromatography on silica gel (methanol in DCM, 0 to 10%). This gave the desired product as slightly yellow oil (150 mg).

$^1$H NMR (400 MHz, CDCl3) δ: 4.08 (t, J=6.8 Hz, 4H), 3.42 (t-like, 6.2 Hz, 2H), 3.18 (quintet-like, 5.5 Hz, 1H), 2.51-2.44 (m, 2H), 2.36 (s, 6H), 2.29-2.22 (m, 2H), 1.85 (br. Water, shift to low field might be due to interaction between amino group and water), 1.67-1.55 (m, 12H), 1.55-1.41 (m, 8H), 1.39-1.21 (m, 32H), 0.89 (2 sets of triplets, 12H).

Synthesis of Compound 22

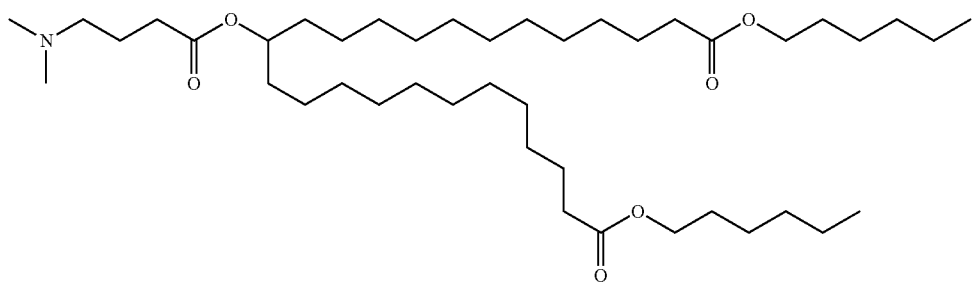 [SMILES: CCCCCCOC(=O)CCCCCCCCCCCC(CCCCCCCCCCCC(=O)OCCCCCC)OC(=O)CCCN(C)C]

Compound 22 was prepared as follows.

Synthesis of Intermediate 16 (13-oxo-pentacosane-1,25-dioic acid (SMA-11-100))

Sodium ethoxide (1.56 g) was dissolved in absolute ethanol (30 mL). Diethylacetone dicarboxylate (4.5 g) was added and the solution heated to reflux. Ethyl 11-bromododecanoate (6.8 g) was slowly added and the solution refluxed for an hour. Sodium ethoxide (1.53 g) was added, followed by ethyl 11-bromododecanoate (18 g). The solution was refluxed overnight. The reaction mixture was cooled, diluted with water, acidified with dilute hydrochloric acid and extracted with methylene chloride. The organic fraction was washed with water and the solvent removed. The crude product was passed down a silica gel column (80 g) using methanol/methylene chloride as the eluent to recover unreacted starting materials. The residue containing the product was treated with acetic acid (10 mL) and concentrated hydrochloric acid (20 mL), and then refluxed overnight. The solution was cooled, diluted with water and filtered. The collected precipitate was recrystallized from acetone, yielding 13-oxo-pentacosane-1,25-dioic acid as a white powder (2.9 g).

Synthesis of 1,25-bis(hexyl) 13-oxo-pentacosanedioate

A solution of Intermediate 16 (13-oxo-pentacosane-1,25-dioic acid) (1.00 g), 4-dimethylaminopyridine (1.12 g), N-(3-dimethylaminopropyl)-N-ethylcarbodiimide hydrochloride (0.99 g) and nonan-5-ol (1.40 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 0.82 g of product.

Synthesis of 1,25-bis(hexyl) 13-hydroxy-pentacosanedioate

A solution of 1,25-bis(hexyl) 13-oxo-pentacosanedioate (0.82 g) in tetrahydrofuran (23 mL) and methanol (10 mL) was treated with sodium borohydride (0.63 g). The reaction was stirred for 15 minutes and then diluted with water, acidified and extracted with dichloromethane. The organic fraction was dried over anhydrous magnesium sulfate, filtered and the solvent removed. The residue was passed down a silica gel (20 g) column using dichloromethane as the eluent, yielding 0.59 g of product.

Synthesis of 1,25-dihexyl 13-{[4-(dimethylamino)butanoyl]oxy}pentacosanedioate A solution of 1,25-bis(hexyl) 13-hydroxy-pentacosanedioate (0.59 g), 4-dimethylaminopyridine (0.46 g), N-(3-dimethylaminopropyl)-N-ethylcarbodiimide hydrochloride (0.36 g) and N,N-dimethylaminobutyric acid hydrochloride (0.64 g) in dichloromethane (20 mL) was stirred at room temperature for one hour. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-4% methanol/dichloromethane as the eluent, yielding 0.57 g of product. $^1$H NMR (CDCl$_3$): δ4.87 (p; J=6.2 Hz; 3H); 4.06 (t; J=6.7 Hz; 4H); 2.25-2.36 (m; 8H); 2.3 (m; 8H); 2.22 (s; 6H); 1.79 (p; J=7.4 Hz; 2H); 0.90 (t; J=6.8 Hz; 6H).

Synthesis of Compound 23

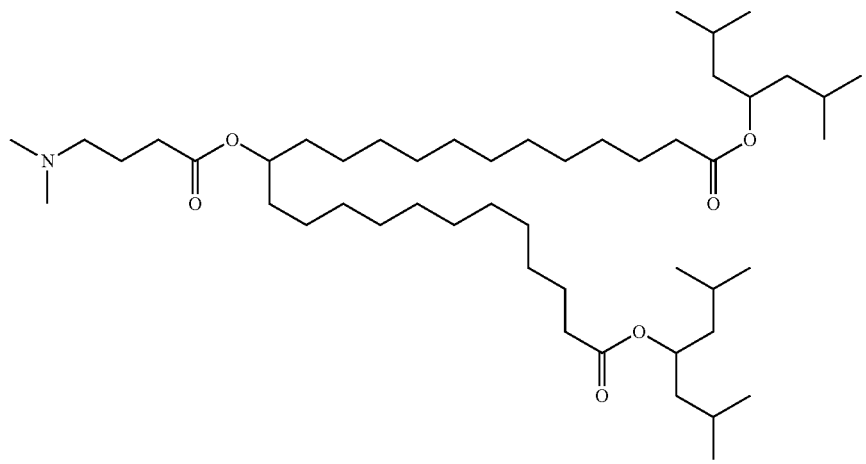 [SMILES: CC(C)CC(CC(C)C)OC(=O)CCCCCCCCCCCC(CCCCCCCCCCCC(=O)OC(CC(C)C)CC(C)C)OC(=O)CCCN(C)C]

Synthesis of 1,25-bis(2,6-dimethylheptan-4-yl) 13-oxopentacosanedioate

A solution of Intermediate 16 (13-oxo-pentacosane-1,25-dioic acid) (1.01 g), 4-dimethylaminopyridine (0.86 g), N-(3-dimethylaminopropyl)-N-ethylcarbodiimide hydrochloride (0.95 g) and 2,6-dimethylheptan-4-ol (1.92 g) in dichloromethane (20 mL) was stirred at room temperature overnight. The solution was washed with diluted hydrochloric acid, dried over anhydrous magnesium sulfate, filtered and the solvent removed. The residue was passed down a silica gel (20 g) column using dichloromethane as the eluent, yielding 0.40 g of product.

Synthesis of 1,25-bis(2,6-dimethylheptan-4-yl) 13-hydroxypentacosanedioate

A solution of 1,25-bis(2,6-dimethylheptan-4-yl) 13-oxopentacosanedioate (0.40 g) in tetrahydrofuran (10 mL) and methanol (10 mL) was treated with sodium borohydride. The reaction was stirred for 30 minutes and then diluted with water, acidified and extracted with dichloromethane. The organic fraction was dried over anhydrous magnesium sulfate, filtered and the solvent removed. The residue was passed down a silica gel (20 g) column using dichloromethane as the eluent, yielding 0.40 g of product.

Synthesis of 1,25-bis(2,6-dimethylheptan-4-yl) 13-{[4-(dimethylamino)butanoyl]oxy}-pentacosanedioate A solution of 1,25-bis(2,6-dimethylheptan-4-yl) 13-hydroxypentacosanedioate (0.49 g), 4-dimethylaminopyridine (0.45 g), N-(3-dimethylaminopropyl)-N-ethylcarbodiimide hydrochloride (0.28 g) and N,N-dimethylaminobutyric acid hydrochloride (0.32 g) in dichloromethane (20 mL) was stirred at room temperature for two hours. The solution was washed with diluted hydrochloric acid followed by aqueous sodium bicarbonate. The organic phase was dried over anhydrous magnesium sulfate, filtered and the solvent removed. The residue was passed down a silica gel (20 g) column using 0-8% methanol/dichloromethane as the eluent, yielding 0.48 g of product. $^1$H NMR (CDCl$_3$): δ5.07 (m, J=4.3 Hz; 2H); 4.87 (p; J=6.4 Hz; 1H); 4.15 (t; J=6.4 Hz; 8H); 2.32 (t; J=7.5 Hz; 2H); 2.27 (q; J=7.6 Hz; 6H); 2.22 (s; 6H); 1.79 (p; J=7.5 Hz; 2H); 0.90 (d; J=6.6 Hz; 24H).

Example 2

FVII In Vivo Evaluation Using the Cationic Lipid Derived Liposomes

C57BL/6 mice (Charles River Labs, Mass.) receive either saline or siRNA in desired formulations via tail vein injection at a volume of 0.01 mL/g. At various time points post-administration, animals are anesthesized by isofluorane inhalation and blood is collected into serum separator tubes by retro orbital bleed. Serum levels of Factor VII protein are determined in samples using a chromogenic assay (Coaset Factor VII, DiaPharma Group, OH or Biophen FVII, Aniara Corporation, OH) according to manufacturer protocols. A standard curve is generated using serum collected from saline treated animals. In experiments where liver mRNA levels are assessed, at various time points post-administration, animals are sacrificed and livers are harvested and snap frozen in liquid nitrogen. Frozen liver tissue is ground into powder. Tissue lysates are prepared and liver mRNA levels of Factor VII and apoB are determined using a branched DNA assay (QuantiGene Assay, Panomics, Calif.).

Example 3

Determination of Efficacy of Lipid Particle Formulations Containing Various Cationic Lipids Using an In Vivo Rodent Factor VII Silencing Model Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining siRNA-mediated downregulation of hepatocyte-derived proteins, as well as monitoring plasma concentrations and tissue distribution of the nucleic acid lipid particles and siRNA, such as the siRNA shown in Table 19.

TABLE 19

| Duplex | Sequence 5'-3' | SEQ ID NO: | Target |
|---|---|---|---|
| AD-1661 | GGAfUfCAfUfCfUfCAAGfUfCfUfUA fCdTsdT | 1 | FVII |
|  | GfUAAGAfCfUfUGAGAfUGAfUfCfCd TsdT | 2 | |

Lower case is 2'OMe modification and Nf is a 2'F modified nucleobase, dT is deoxythymidine, s is phosphothioate The cationic lipids described herein are used to formulate liposomes containing the AD-1661duplex using an in-line mixing method, as described in International Publication No. WO 2010/088537, which is incorporated by reference in its entirety. Lipid particles are formulated using the following molar ratio: 50% Cationic lipid/10% distearoylphosphatidylcholine (DSPC)/38.5% Cholesterol/1.5% PEG-DMG (1-(monomethoxy-polyethyleneglycol)-2,3-dimyristoylglycerol, with an average PEG molecular weight of 2000).

C57BL/6 mice (Charles River Labs, Mass.) receive either saline or formulated siRNA via tail vein injection. At various time points after administration, serum samples are collected by retroorbital bleed. Serum levels of Factor VII protein are determined in samples using a chromogenic assay (Biophen FVII, Aniara Corporation, OH). To determine liver mRNA levels of Factor VII, animals are sacrificed and livers are harvested and snap frozen in liquid nitrogen. Tissue lysates are prepared from the frozen tissues and liver mRNA levels of Factor VII are quantified using a branched DNA assay (QuantiGene Assay, Panomics, Calif.).

FVII activity is evaluated in FVII siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 4 siRNA Formulation Using Preformed Vesicles

Cationic lipid containing particles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. This generally requires 1-3 passes. For some cationic lipid mixtures which do not form small vesicles hydrating the lipid mixture with a lower pH buffer (50 mM citrate, pH 3) to protonate the phosphate group on the DSPC headgroup helps form stable 70-90 nm vesicles.

The FVII siRNA (solubilised in a 50 mM citrate, pH 4 aqueous solution containing 30% ethanol) is added to the vesicles, pre-equilibrated to 35° C., at a rate of ~5 mL/min with mixing. After a final target siRNA/lipid ratio of 0.06 (wt/wt) is achieved, the mixture is incubated for a further 30 minutes at 35° C. to allow vesicle re-organization and encapsulation of the FVII siRNA. The ethanol is then removed and the external buffer replaced with PBS (155 mM NaCl, 3 mM Na2HPO4, 1 mM KH2PO4, pH 7.5) by either dialysis or tangential flow diafiltration. The final encapsulated siRNA-to-lipid ratio is determined after removal of unencapsulated siRNA using size-exclusion spin columns or ion exchange spin columns.

Example 5

In Vivo Determination of Efficacy of Lipid Formulations

Test formulations were prepared using the following in-line mixing method:

General Protocol for the In-Line Mixing Method

Individual and separate stock solutions are prepared—one containing lipid and the other siRNA. Lipid stock containing lipid A, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3-5, depending on the type of fusogenic lipid employed. The siRNA is also solubilized in citrate buffer at a concentration of 4 mg/mL. For small scale, 5 mL of each stock solution is prepared.

Stock solutions are completely clear and lipids must be completely solubilized before combining with siRNA. Therefore stock solutions may be heated to completely solubilize the lipids. The siRNAs used in the process may be unmodified oligonucleotides or modified and may be conjugated with lipophilic moieties such as cholesterol.

The individual stocks are combined by pumping each solution to a T-junction. A dual-head Watson-Marlow pump is used to simultaneously control the start and stop of the two streams. A 1.6 mm polypropylene tubing is further downsized to a 0.8 mm tubing in order to increase the linear flow rate. The polypropylene line (ID=0.8 mm) are attached to either side of a T-junction. The polypropylene T has a linear edge of 1.6 mm for a resultant volume of 4.1 mm. Each of the large ends (1.6 mm) of polypropylene line is placed into test tubes containing either solubilized lipid stock or solubilized siRNA. After the T-junction a single tubing is placed where the combined stream will emit. The tubing is then extending into a container with 2× volume of PBS. The PBS is rapidly stirring. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

Test formulations are initially assessed for their FVII knockdown in female 7-9 week old, 15-25 g, female C57Bl/6 mice at 0.1, 0.3, 1.0 and 5.0 mg/kg with 3 mice per treatment group. All studies include animals receiving either phosphate-buffered saline (PBS, Control group) or a benchmark formulation. Formulations are diluted to the appropriate concentration in PBS immediately prior to testing. Mice are weighed and the appropriate dosing volumes calculated (10 µl/g body weight). Test and benchmark formulations as well as PBS (for Control animals) are administered intravenously via the lateral tail vein. Animals are anesthetised 24 hours later with an intraperitoneal injection of Ketamine/Xylazine and 500-700 µl of blood is collected by cardiac puncture into serum separator tubes (BD Microtainer). Blood is centrifuged at 2,000×g for 10 minutes at 15° C. and serum is collected and stored at −70° C. until analysis. Serum samples are thawed at 37° C. for 30 minutes, diluted in PBS and aliquoted into 96-well assay plates. Factor VII levels are assessed using a chromogenic assay (Biophen FVII kit, Hyphen BioMed) according to manufacturer's instructions and absorbance is measured in a microplate reader equipped with a 405 nm wavelength filter. Plasma FVII levels are quantified and $ED_{50}$s (dose resulting in a 50% reduction in plasma FVII levels compared to control animals) calculated using a standard curve generated from a pooled sample of serum from control animals. Those formulations of interest showing high levels of FVII knockdown ($ED_{50} \ll 0.1$ mg/kg) are re-tested in independent studies at a lower dose range to confirm potency and establish $ED_{50}$ levels.

The following table shows $ED_{50}$ values for some of the cationic lipids described herein:

| Cationic Lipid Compound | $ED_{50}$ (Mouse FVII) (mg/kg) |
|---|---|
| 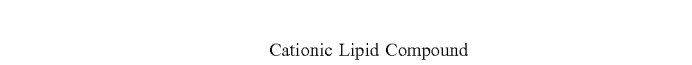 | >0.30 |

-continued
| Cationic Lipid Compound | ED$_{50}$ (Mouse FVII) (mg/kg) |
|---|---|
| 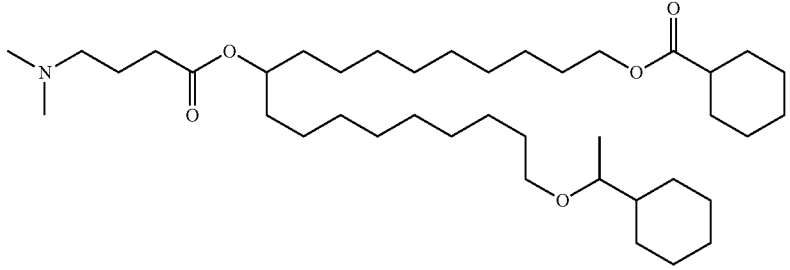 [SMILES: CC(OCCCCCCCCCC(CCCCCCCCCOC(=O)C1CCCCC1)OC(=O)CCCN(C)C)C1CCCCC1] | 0.032 |
| 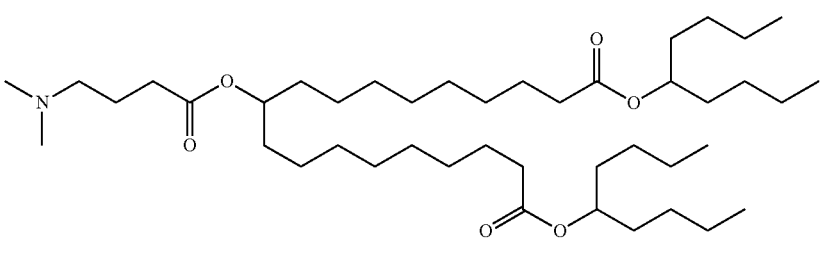 [SMILES: CCCCC(CCCC)OC(=O)CCCCCCCCC(CCCCCCCCC(=O)OC(CCCC)CCCC)OC(=O)CCCN(C)C] | 0.010 |
| 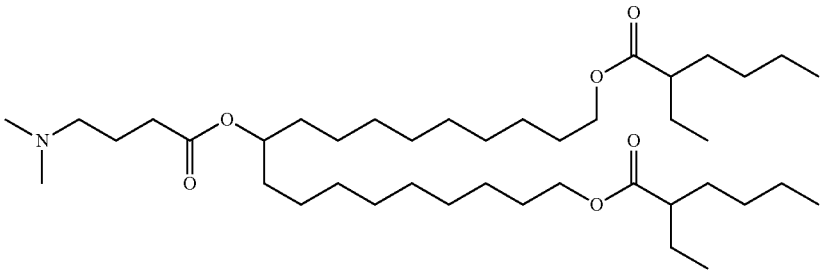 [SMILES: CCCCC(CC)C(=O)OCCCCCCCCCC(CCCCCCCCCOC(=O)C(CC)CCCC)OC(=O)CCCN(C)C] | 0.005 |
| 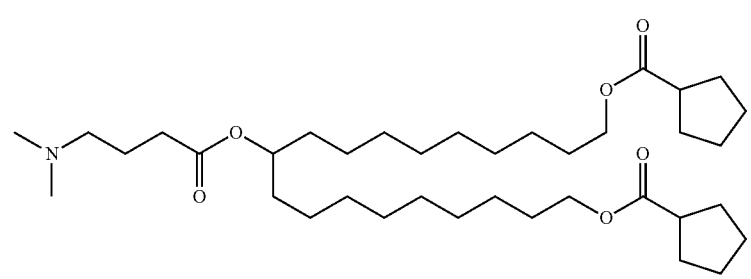 [SMILES: CN(C)CCCC(=O)OC(CCCCCCCCCOC(=O)C1CCCC1)CCCCCCCCCOC(=O)C1CCCC1] | >0.30 |
| 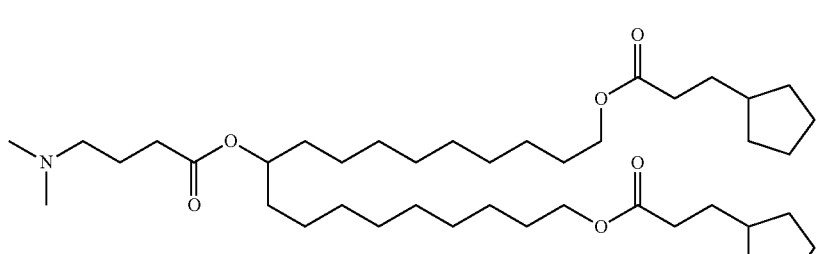 | 0.023 |

| Cationic Lipid Compound | ED$_{50}$ (Mouse FVII) (mg/kg) |
|---|---|
| 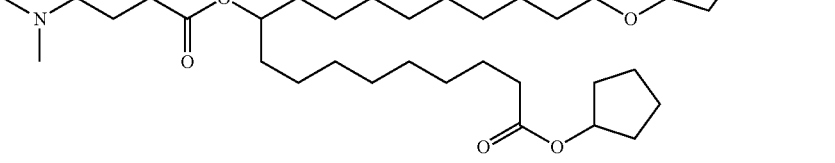 | >0.30 |
| 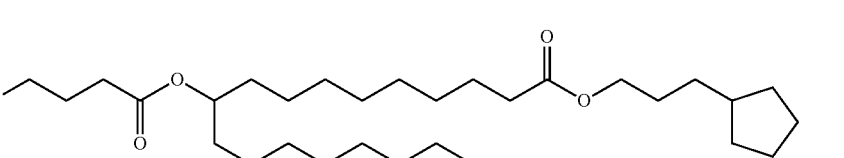 | 0.12 |
| 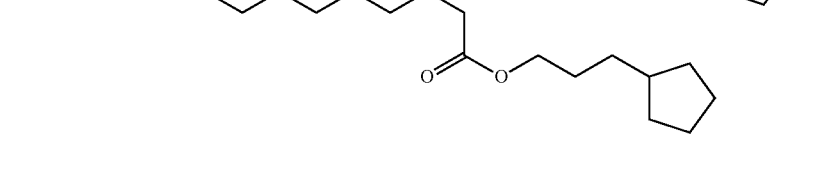 | >0.30 |
| 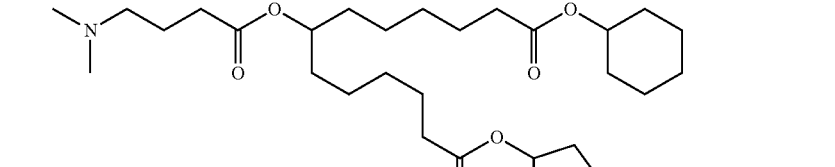 | >0.30 |
| 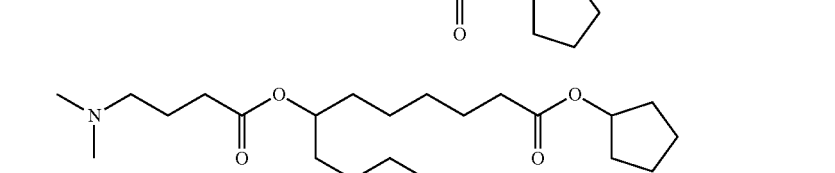 | >0.30 |
| 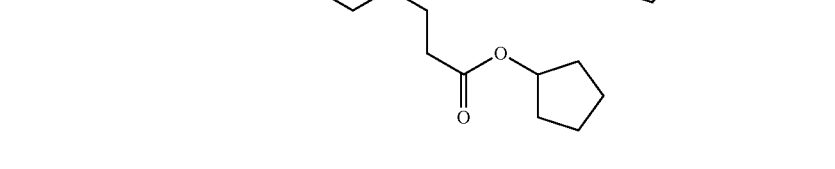 | >0.30 |

| Cationic Lipid Compound | ED$_{50}$ (Mouse FVII) (mg/kg) |
|---|---|
| 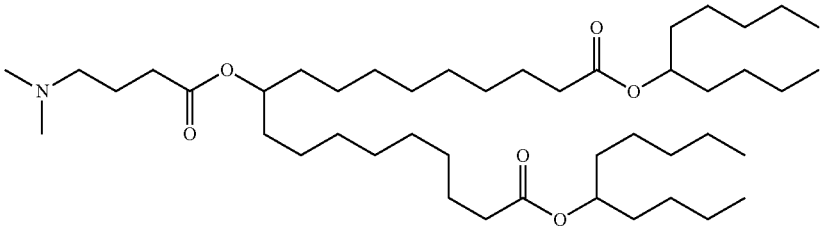 [SMILES: CCCCCC(CCCC)OC(=O)CCCCCCCCC(CCCCCCCCC(=O)OC(CCCC)CCCCC)OC(=O)CCCN(C)C] | 0.009 |
| 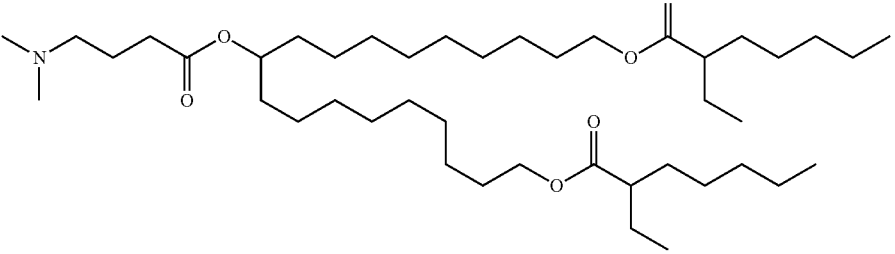 | 0.008 |
| 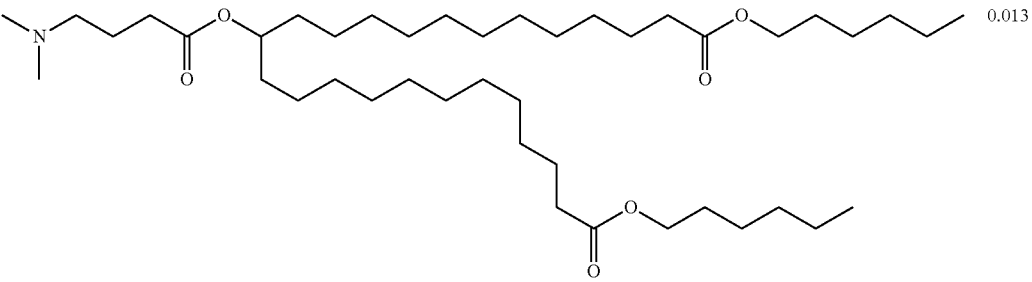 | 0.013 |
| 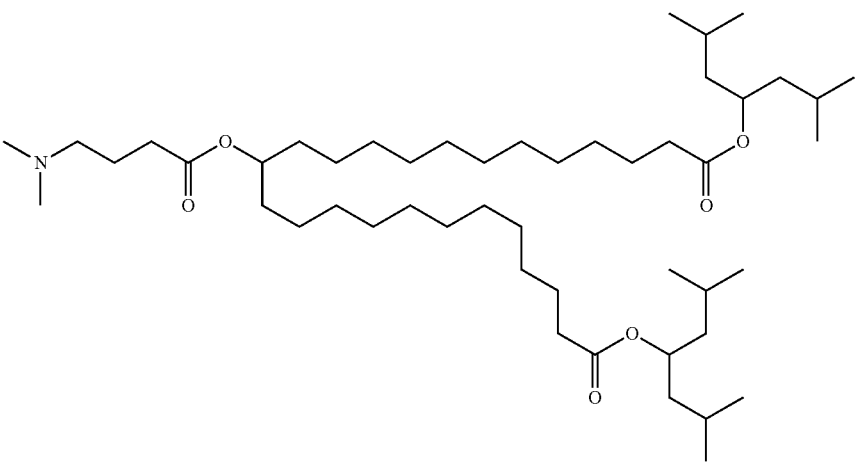 [SMILES: CC(C)CC(CC(C)C)OC(=O)CCCCCCCCCCCC(CCCCCCCCCCCC(=O)OC(CC(C)C)CC(C)C)OC(=O)CCCN(C)C] | 0.020 |
| 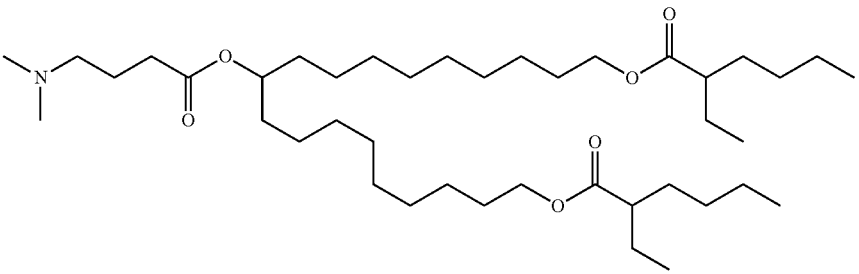 [SMILES: CCCCC(CC)C(=O)OCCCCCCCCCC(CCCCCCCCCOC(=O)C(CC)CCCC)OC(=O)CCCN(C)C] | 0.088 |

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound of Formula (I):

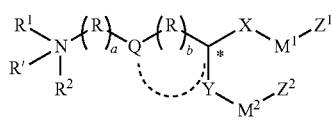

Formula (I)

or a salt thereof, wherein
R' is absent, hydrogen, or alkyl;
with respect to $R^1$ and $R^2$,
  (i) $R^1$ and $R^2$ are each, independently, optionally substituted alkyl, alkenyl, alkynyl, cycloalkyl, cycloalkylalkyl, heterocycle, or $R^{10}$;
  (ii) $R^1$ and $R^2$, together with the nitrogen atom to which they are attached, form an optionally substituted heterocylic ring; or
  (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the $(R)_a$ group adjacent to the nitrogen atom;
each occurrence of R is, independently, —$(CR^3R^4)$—;
each occurrence of $R^3$ and $R^4$ are, independently hydrogen, OH, alkyl, alkoxy, —$NH_2$, $R^{10}$, alkylamino, or dialkylamino;
each occurrence of $R^{10}$ is independently selected from PEG and polymers based on poly(oxazoline), poly(ethylene oxide), poly(vinyl alcohol), poly(glycerol), poly(N-vinylpyrrolidone), poly[N-(2-hydroxypropyl) methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula (I) has at most two $R^{10}$ groups;
the dashed line to Q is absent or a bond;
when the dashed line to Q is absent then Q is absent or is —O—, —NH—, —S—, —C(O)—, —C(O)O, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or
when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms;
each occurrence of $R^5$ is, independently, hydrogen or alkyl;
X and Y are each, independently, —$(CR^6R^7)_c$—;
each occurrence of $R^6$ and $R^7$ are, independently hydrogen, OH, alkyl, alkoxy, —$NH_2$, alkylamino, or dialkylamino;

$M^1$ and $M^2$ are each, independently, a biodegradable group;
a is 1, 2, 3, 4, 5 or 6;
b is 0, 1, 2, or 3;
each occurrence of c is, independently, 2-10; and
$Z^1$ and $Z^2$ are each, independently (i) $C_3$-$C_{10}$ cycloalkyl, (ii) $C_3$-$C_{10}$ cycloalkyl($C_1$-$C_6$ alkyl), or (iii)

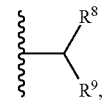

wherein each of $R^8$ and $R^9$ is a $C_2$-$C_8$ alkyl.

2. The compound of claim 1, wherein $M^1$ and $M^2$ are each, independently, —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R_5$)—, —N($R^5$)C(O)—, —N($R^5$)C(O)N($R^5$)—, —OC(O)O—, —OSi($R^5$)$_2$O—, —C(O)($CR^3R^4$)C(O)O—, or —OC(O)($CR^3R^4$)C(O)—.

3. The compound of claim 1, wherein $M^1$ and $M^2$ are each, independently, —OC(O)— or —C(O)O—.

4. The compound of claim 1, wherein $R^1$ and $R^2$ are each alkyl.

5. The compound of claim 1, wherein $R^1$ and $R^2$ are each methyl.

6. The compound of claim 1, wherein a is 3 and b is 0.

7. The compound of claim 1, wherein X and Y are each, independently —$(CH_2)_c$—.

8. The compound of claim 1, wherein $Z^1$ and $Z^2$ are each, independently, $C_3$-$C_{10}$ cycloalkyl.

9. The compound of claim 8, wherein $Z^1$ and $Z^2$ are each cyclohexyl or decahydronaphthalenyl.

10. The compound of claim 1, wherein $Z^1$ and $Z^2$ are each, independently, represented by Formula II:

Formula II wherein $R^8$ and $R^9$ are each, independently, $C_3$-$C_8$ alkyl.

11. The compound of claim 1, selected from:
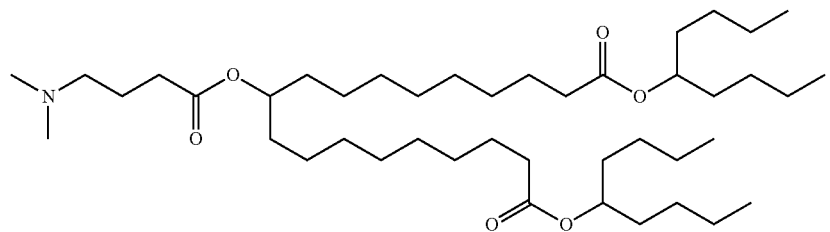
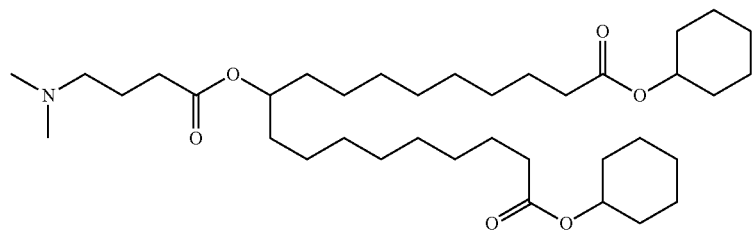
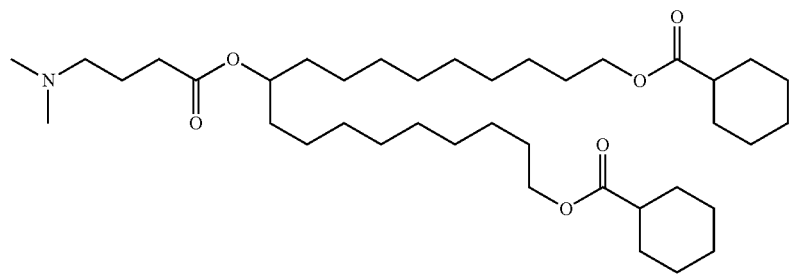
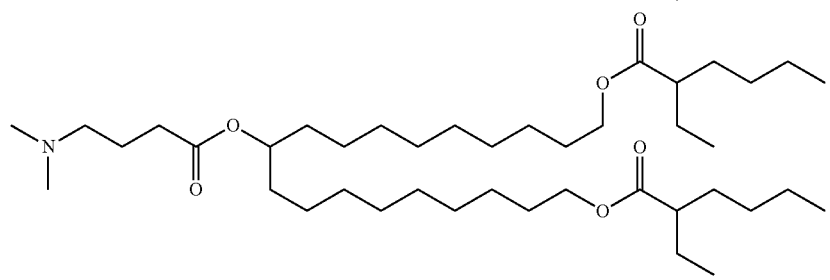
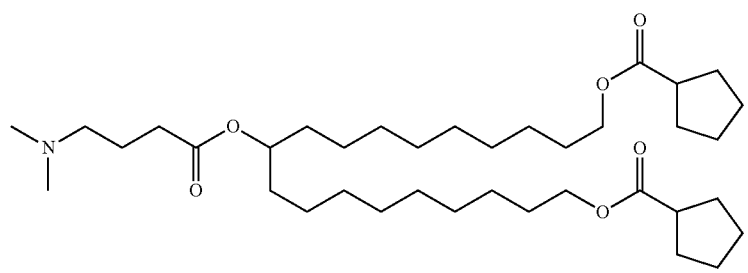
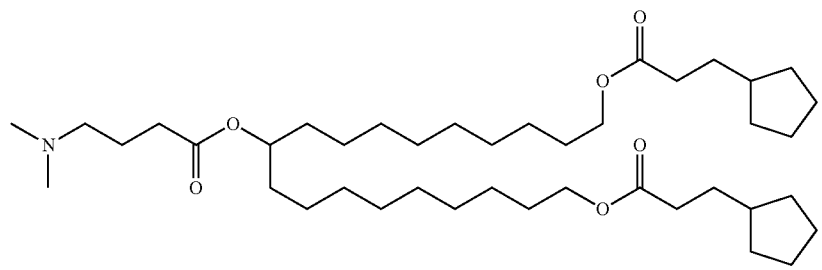

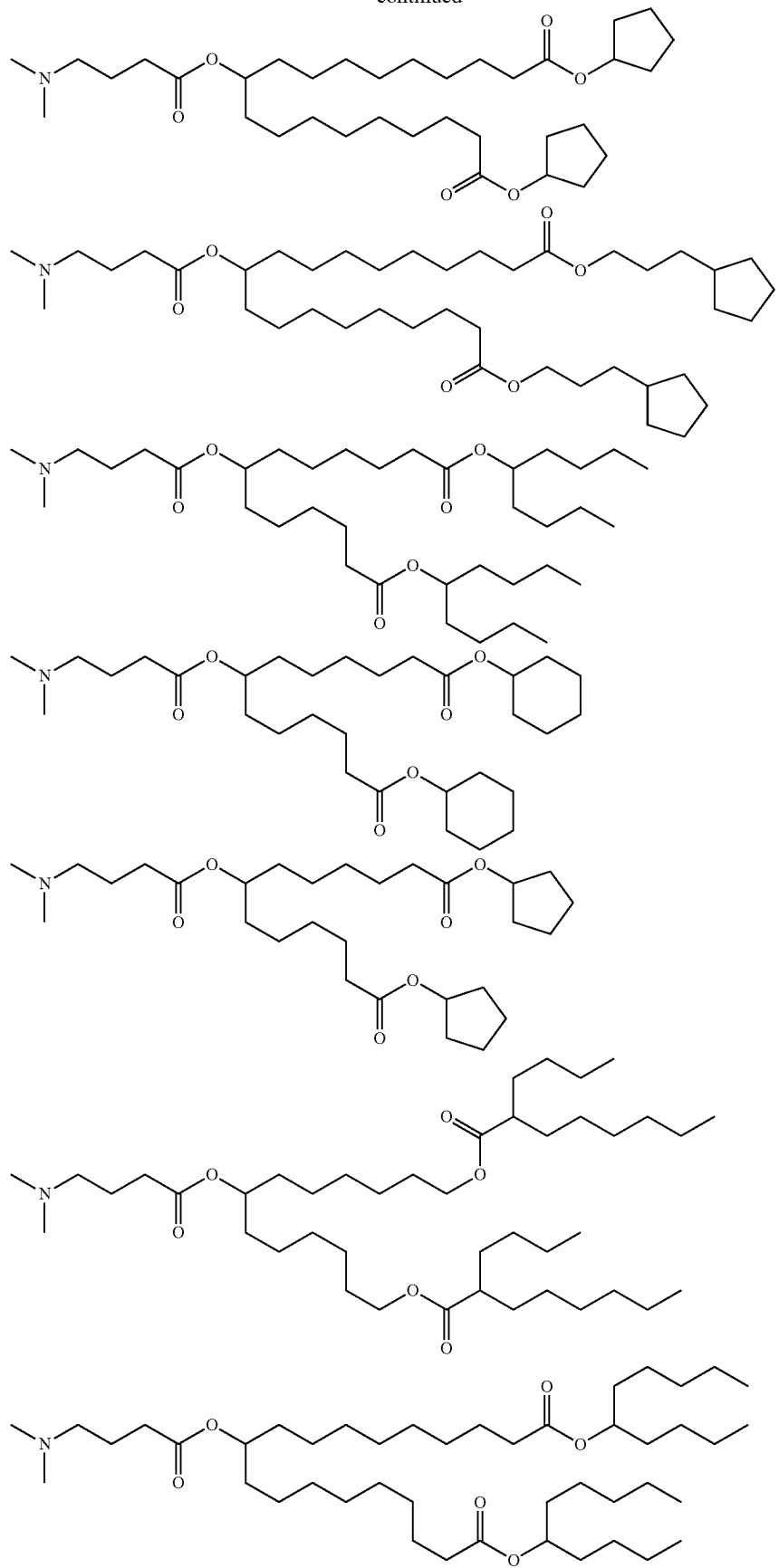

-continued
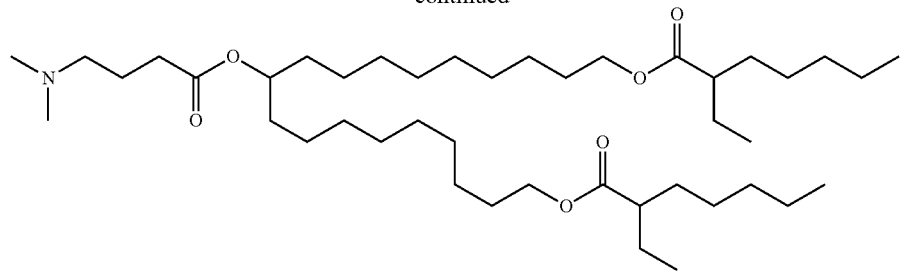
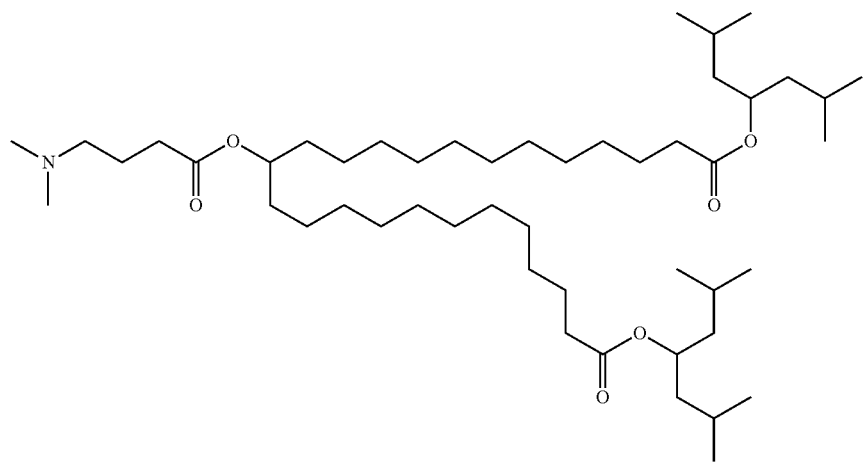
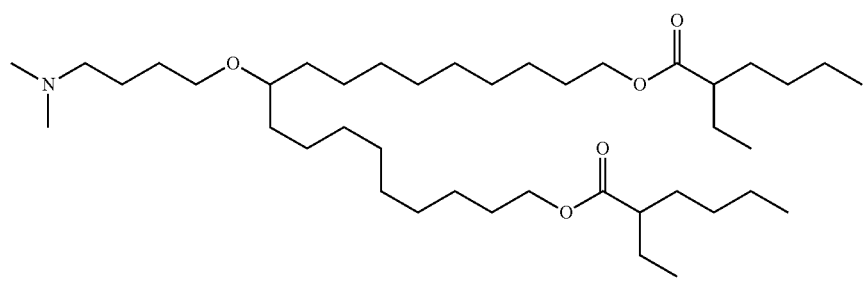
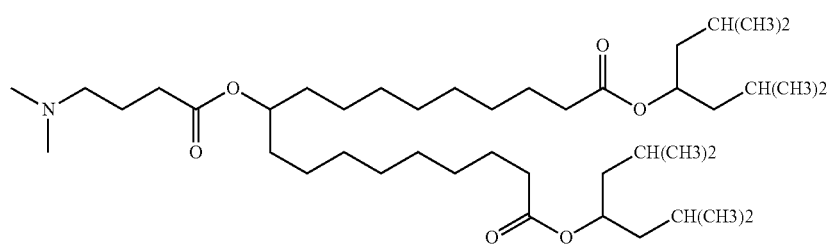
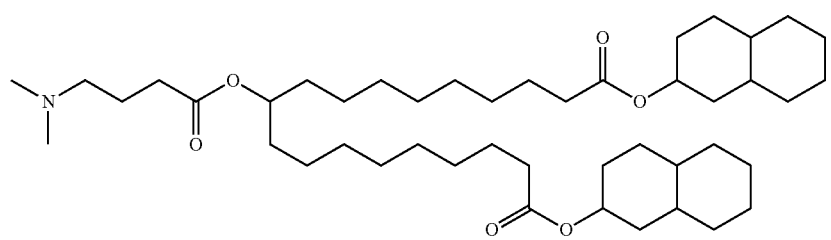
and salts thereof.

12. A compound selected from
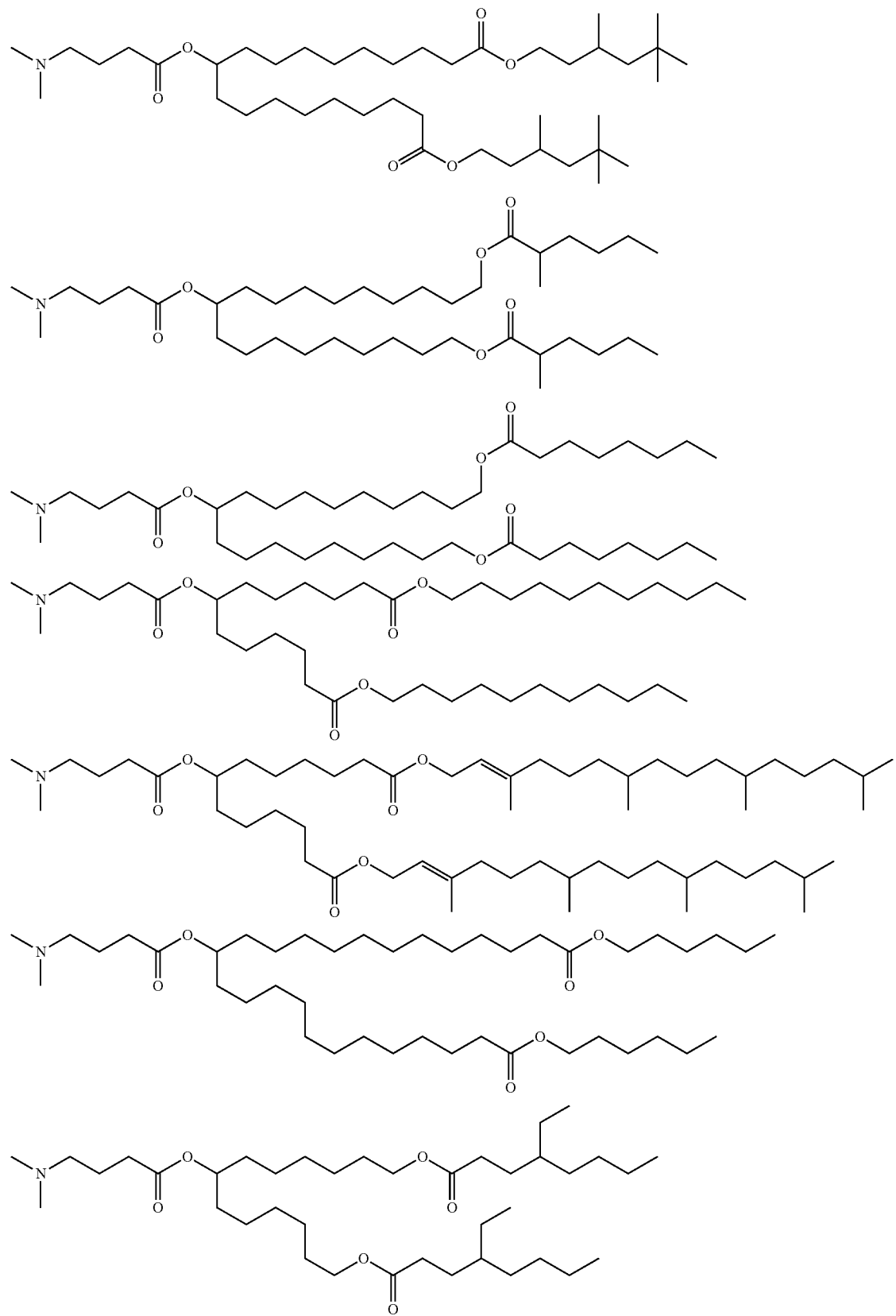

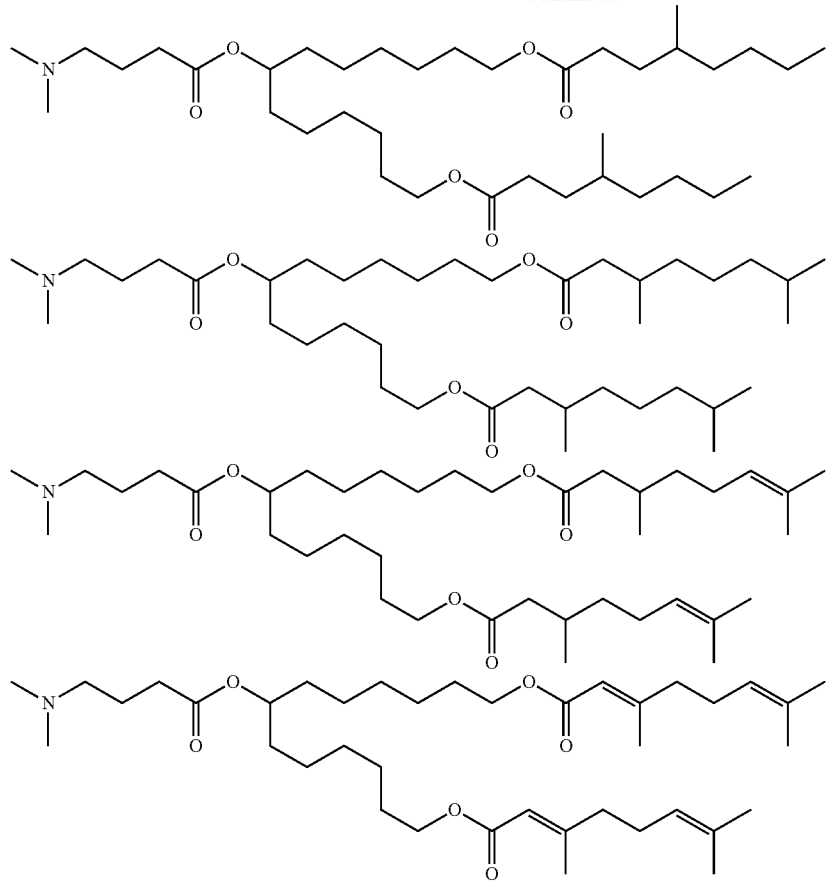

and salts thereof.

13. The compound of claim 1, wherein the compound is in the form of a pharmaceutically acceptable salt.

14. The compound of claim 1, wherein the compound is in the form of a cationic lipid containing a negatively charged counter ion.

15. A lipid particle comprising a neutral lipid, a lipid capable of reducing aggregation, and a cationic lipid of claim 14.

16. The lipid particle of claim 15, wherein the neutral lipid is selected from DSPC, DPPC, POPC, DOPE, or SM; the lipid capable of reducing aggregation is a PEG lipid; and the lipid particle further comprises a sterol.

17. The lipid particle of claim 16, wherein the cationic lipid is present in a mole percentage of about 20% and about 60%; the neutral lipid is present in a mole percentage of about 5% to about 25%; the sterol is present in a mole percentage of about 25% to about 55%; and the PEG lipid is PEG-DMA, PEG-DMG, or a combination thereof, and is present in a mole percentage of about 0.5% to about 15%.

18. The lipid particle of claim 15, further comprising an active agent.

19. The lipid particle of claim 18, wherein the active agent is a nucleic acid selected from a plasmid, an immunostimulatory oligonucleotide, an siRNA, an antisense oligonucleotide, a microRNA, an antagomir, an aptamer, and a ribozyme.

20. The lipid particle of claim 15, wherein the lipid particle has an in vivo half life ($t_{1/2}$) of less than about 3 hours.

21. The lipid particle of claim 15, wherein the lipid particle has an in vivo half life ($t_{1/2}$) of less than about 10% of that for a lipid particle containing the same cationic lipid without a biodegradable group.

22. A pharmaceutical composition comprising a lipid particle of claim 18 and a pharmaceutically acceptable carrier.

23. A method of modulating the expression of a target gene in a cell, comprising providing to the cell a lipid particle of claim 18.

24. The method of claim 23, wherein the active agent is a nucleic acid is an siRNA.

25. A method of treating a disease or disorder characterized by the overexpression of a polypeptide in a subject, comprising providing to the subject the pharmaceutical composition of claim 22, wherein the active agent is a nucleic acid selected from the group consisting of an siRNA, a microRNA, and an antisense oligonucleotide, and wherein the siRNA, microRNA, or antisense oligonucleotide includes a polynucleotide that specifically binds to a polynucleotide that encodes the polypeptide, or a complement thereof.

26. A method of treating a disease or disorder characterized by underexpression of a polypeptide in a subject, comprising providing to the subject the pharmaceutical composition of claim 22, wherein the active agent is a plasmid that encodes the polypeptide or a functional variant or fragment thereof.

27. A method of inducing an immune response in a subject, comprising providing to the subject the pharmaceutical composition of claim 22, wherein the active agent is an immunostimulatory oligonucleotide.

28. The method of claim 23, wherein the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA (p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STATS gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, tumor suppressor genes, and p53 tumor suppressor gene.

29. The method of claim 23, wherein the target gene contains one or more mutations.

\* \* \* \* \*